United States Patent [19]
Chen et al.

[11] Patent Number: 5,852,210
[45] Date of Patent: Dec. 22, 1998

[54] CINNAMIC ACID DERIVATIVES

[75] Inventors: Barbara B. Chen, Glenview, Ill.; Helen Y. Chen, Livingston, N.J.; Michael Clare, Skokie, Ill.; Stephen H. Docter, Chicago, Ill.; Ish Kumar Khanna, Vernon Hills, Ill.; Francis Jan Koszyk, Prospect Heights, Ill.; James W. Malecha, Libertyville, Ill.; Julie Marion Miyashiro, Skokie, Ill.; Thomas D. Penning, Elmhurst, Ill.; Joseph G. Rico; Peter G. Ruminski, both of Ballwin, Mo.; Mark A. Russell, Gurnee, Ill.; Richard Mathias Weier, Lake Bluff, Ill.; Xiangdong Xu, Gurnee, Ill.; Stella S. Yu, Morton Grove, Ill.; Yi Yu, Skokie, Ill.

[73] Assignee: G. D. Searle & Co., Chicago, Ill.

[21] Appl. No.: 825,080

[22] Filed: Mar. 27, 1997

Related U.S. Application Data

[60] Provisional application No. 60/014,325 Mar. 29, 1996.
[51] Int. Cl.⁶ .................. C07C 241/00; C07C 205/00; C07D 233/44; C07D 239/02
[52] U.S. Cl. .................. 562/439; 560/21; 548/331.5; 544/332
[58] Field of Search .................. 544/332; 548/331.5; 560/21; 562/439

[56] References Cited

U.S. PATENT DOCUMENTS 5,523,302  6/1996  Cain et al. .................. 514/252

FOREIGN PATENT DOCUMENTS

| | | | |
|---|---|---|---|
| 0 478 328 A1 | 4/1992 | European Pat. Off. | ...... C07C 271/22 |
| 0 478 363 A2 | 4/1992 | European Pat. Off. | ...... C07D 211/22 |
| WO 95/32710 | 12/1995 | WIPO | ............. A61K 31/18 |

OTHER PUBLICATIONS

J. Am. Chem. Soc. (1983), 105(6), pp. 1697–1698. Wasserman, 'Total synthesis of chaenorhine.'

*Primary Examiner*—Gary Geist
*Assistant Examiner*—Brian J. Davis
*Attorney, Agent, or Firm*—Cynthia S. Kovacevic

[57] ABSTRACT

The present invention relates to a class of compounds represented by the Formula I

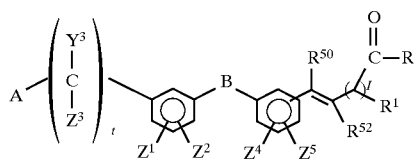

or a pharmaceutically acceptable salt thereof, pharmaceutical compositions comprising compounds of the Formula I, and methods of selectively inhibiting or antagonizing the $\alpha_v\beta_3$ integrin.

32 Claims, No Drawings

CINNAMIC ACID DERIVATIVES

FIELD OF THE INVENTION

The present invention relates to pharmaceutical agents (compounds) which are useful as $\alpha_v\beta_3$ integrin antagonists or inhibitors and as such are useful in pharmaceutical compositions and in methods for treating conditions mediated by $\alpha_v\beta_3$ by inhibiting or antagonizing $\alpha_v\beta_3$ integrins.

BACKGROUND OF THE INVENTION

Integrins are a group of cell surface glycoproteins which mediate cell adhesion and therefore are useful mediators of cell adhesion interactions which occur during various biological processes. Integrins are heterodimers composed of noncovalently linked $\alpha$ and $\beta$ polypeptide subunits. Currently eleven different $\alpha$ subunits have been identified and six different $\beta$ subunits have been identified. The various $\alpha$ subunits can combine with various $\beta$ subunits to form distinct integrins.

The integrin identified as $\alpha_v\beta_3$ (also known as the vitronectin receptor) has been identified as an integrin which plays a role in various conditions or disease states including tumor metastasis, solid tumor growth (neoplasia), osteoporosis, Paget's disease, humoral hypercalcemia of malignancy, angiogenesis, including tumor angiogenesis, retinopathy, arthritis, including rheumatoid arthritis, periodontal disease, psoriasis and smooth muscle cell migration (e.g. restenosis). Additionally, it has been found that such agents would be useful as antivirals, antifungals and antimicrobials. Thus, compounds which selectively inhibit or antagonize $\alpha_v\beta_3$ would be beneficial for treating such conditions.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (Proc. Natl. Acad. Sci. USA, Vol. 89 (1992) 1557–1561) have shown that the $\alpha_v\beta_3$ integrin has a biological function in melanoma cell invasion. Montgomery et al., (Proc. Natl. Acad. Sci. USA, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The adhesion receptor integrin $\alpha_v\beta_3$ was identified as a marker of angiogenic blood vessels in chick and man and therefore such receptor plays a critical role in angiogenesis or neovascularization. Angiogenesis is characterized by the invasion, migration and proliferation of smooth muscle and endothelial cells. Antagonists of $\alpha_v\beta_3$ inhibit this process by selectively promoting apoptosis of cells in neovasculature. The growth of new blood vessels, or angiogenesis, also contributes to pathological conditions such as diabetic retinopathy (Adonis et al., Amer. J. Ophthal., Vol. 118, (1994) 445–450) and rheumatoid arthritis (Peacock et al., J. Exp. Med., Vol. 175, (1992), 1135–1138). Therefore, $\alpha_v\beta_3$ antagonists would be useful therapeutic targets for treating such conditions associated with neovascularization (Brooks et al., Science, Vol. 264, (1994), 569–571).

It has been reported that the cell surface receptor $\alpha_v\beta_3$ is the major integrin on osteoclasts responsible for attachment to bone. Osteoclasts cause bone resorption and when such bone resorbing activity exceeds bone forming activity it results in osteoporosis (a loss of bone), which leads to an increased number of bone fractures, incapacitation and increased mortality. Antagonists of $\alpha_v\beta_3$ have been shown to be potent inhibitors of osteoclastic activity both in vitro [Sato et al., J. Cell. Biol., Vol. 111 (1990) 1713–1723] and in vivo [Fisher et al., Endocrinology, Vol. 132 (1993) 1411–1413]. Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis.

The role of the $\alpha_v\beta_3$ integrin in smooth muscle cell migration also makes it a therapeutic target for prevention or inhibition of neointimal hyperplasia which is a leading cause of restenosis after vascular procedures (Choi et al., J. Vasc. Surg. Vol. 19(1) (1994) 125–34). Prevention or inhibition of neointimal hyperplasia by pharmaceutical agents to prevent or inhibit restenosis would be beneficial.

White (Current Biology, Vol. 3(9)(1993) 596–599) has reported that adenovirus uses $\alpha_v\beta_3$ for entering host cells. The integrin appears to be required for endocytosis of the virus particle and can be required for penetration of the viral genome into the host cell cytoplasm. Thus compounds which inhibit $\alpha_v\beta_3$ would find usefulness as antiviral agents.

SUMMARY OF THE INVENTION

The present invention relates to a class of compounds represented by the Formula I

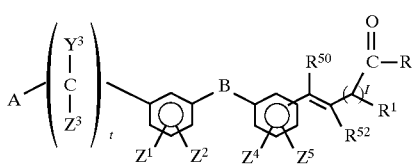

or a pharmaceutically acceptable salt thereof, wherein

A is

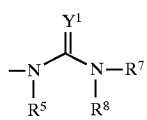

wherein $Y^1$ is selected from the group consisting of $N-R^2$, O, and S;

$R^2$ is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy, carboxy derivatives and phenyl; or $R^2$ taken together with $R^7$ forms a 5 membered heteroaromatic ring; or $R^2$ taken together with $R^7$ forms a 5 membered heteroaromatic ring fused with a phenyl group;

$R^7$ (when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; $-SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

wherein $R^{10}$ is defined above; or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, alkyl, alkenyl, alkynyl, benzyl, and phenethyl;

or

A is

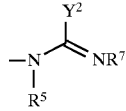

wherein $Y^2$ is selected from the group consisting of alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; $-S-R^9$ and $-O-R^9$ wherein $R^9$ is selected from the group consisting of H; alkyl; aralkyl; aryl; alkenyl; and alkynyl; or $R^9$ taken together with $R^7$ forms a 4–12 membered mononitrogen containing sulfur or oxygen containing heterocyclic ring; and $R^5$ and $R^7$ are as defined above; or $Y^2$ (when $Y^2$ is carbon) taken together with $R^7$ forms a 4–12 membered mononitrogen containing ring optionally substituted with alkyl, aryl or hydroxy;

$Z^1$, $Z^2$, $Z^4$ and $Z^5$ are independently selected from the group consisting of H; alkyl; hydroxy; alkoxy; aryloxy; arylalkoxy; halogen; haloalkyl; haloalkoxy; nitro; amino; aminoalkyl; alkylamino; dialkylamino; cyano; alkylthio; alkylsulfonyl; carboxyl derivatives; carboxyalkenyl; alkoxycarbonylalkenyl; alkoxycarbonylamino; acetamide; aryl; fused aryl; cycloalkyl; thio;

monocyclic heterocycles; fused monocyclic heterocycles; and A, wherein A is defined above;

B is selected from the group consisting of

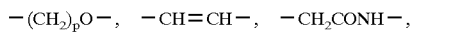

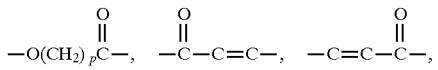

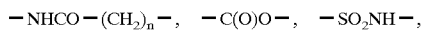

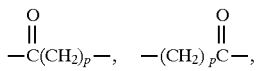

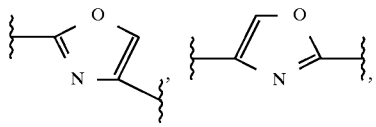

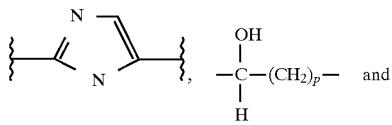

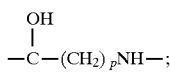

or B is —CONR" wherein R" together with $Z^4$ forms a 5 or 6-membered ring fused to the phenyl;

wherein p is an integer selected from the group consisting of 0, 1 and 2; wherein $R^{11}$ is selected from the group consisting of H, alkyl, alkenyl, alkynyl, benzyl and phenethyl; wherein n is an integer selected from the group consisting of 0, 1, 2 and 3;

l is an integer 0, 1, 2, or 3;

t is an integer 0, 1 or 2;

$R^{50}$ is selected from the group consisting of H, alkyl, aryl and aryl optionally substituted with one or more substituent selected from the group consisting of halo, haloalkyl, hydroxy, alkoxy, alkoxy, aryloxy, aryl, nitro and alkyl;

R is X—$R^3$ wherein X is selected from the group consisting of O, S and $NR^4$, wherein $R^3$ and $R^4$ are independently selected from the group consisting of hydrogen; alkyl; alkenyl; alkynyl; haloalkyl; dialkylaminocarbonyl alkoxy; aryl; arylalkyl; sugars; steroids and in the case of the free acid, all pharmaceutically acceptable salts thereof;

$Y^3$ and $Z^3$ are independently selected from the group consisting of H, alkyl, aryl, cycloalkyl and aralkyl;

$R^1$ is selected from the group consisting of hydrogen; alkyl; amino,

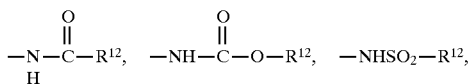

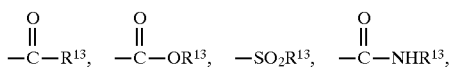

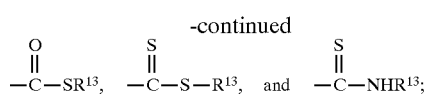

$R^{12}$ is selected from the group consisting of H, alkyl, cycloalkyl, alkylaryl and aryl;

$R^{52}$ is selected from the group consisting of

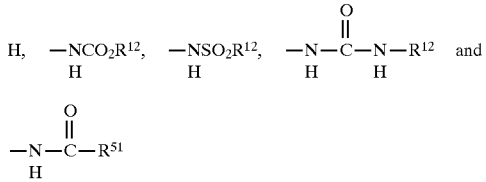

wherein $R^{12}$ is as defined above;

$R^{51}$ is selected from the group consisting of N-substituted pyrrolidinyl, piperidinyl, phenyl and morpholinyl;

$R^{13}$ is selected from the group consisting of hydrogen; alkyl; alkenyl; alkynyl; aryl; carboxyl derivatives; haloalkyl; monocyclic heterocycles; monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido;

alkyl optionally substituted with halo, haloalkyl, hydroxy, alkoxy, aryloxy, thio, alkylthio, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, haloalkyl, cyano, nitro, hydroxy, carboxyl derivatives, alkoxy, aryloxy, amino, alkylamino, dialkylamino, amido, aryl, fused aryl, monocyclic heterocycles; and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl;

aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, carboxyl derivatives, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles; and

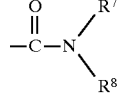

wherein $R^7$ and $R^8$ are as defined above and provided that taken together with the nitrogen, $R^7$ and $R^8$ comprise an amino acid.

It is another object of the invention to provide pharmaceutical compositions comprising compounds of the Formula I. Such compounds and compositions are useful in selectively inhibiting or antagonizing the $\alpha_v\beta_3$ integrin and therefore in another embodiment the present invention relates to a method of selectively inhibiting or antagonizing the $\alpha_v\beta_3$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials.

DETAILED DESCRIPTION

The present invention relates to a class of compounds represented by the Formula I, described above.

A preferred embodiment of the present invention is a compound of the Formula II

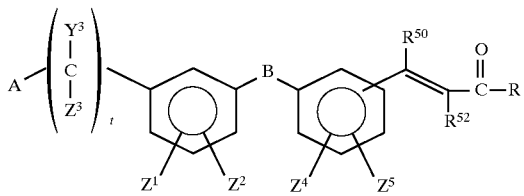

Another preferred embodiment of the present invention is a compound of the Formula III

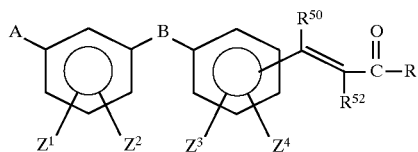

Another preferred embodiment of the present invention is a compound of the Formula IV

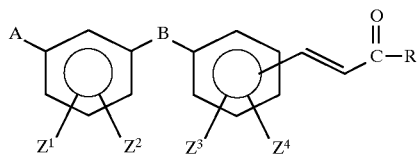

Another preferred embodiment of the present invention is a compound of the Formula V

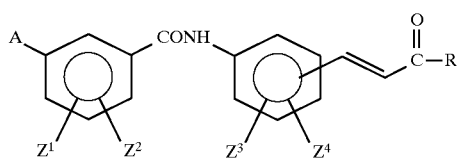

Another preferred embodiment of the present invention is a compound of the Formula VI

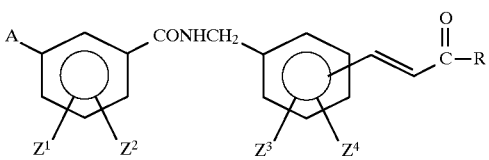

The invention further relates to pharmaceutical compositions containing therapeutically effective amounts of the compounds of Formulas I–VI.

The invention also relates to a method of selectively inhibiting or antagonizing the $\alpha_v\beta_3$ integrin and more specifically relates to a method of inhibiting bone resorption, periodontal disease, osteoporosis, humoral hypercalcemia of malignancy, Paget's disease, tumor metastasis, solid tumor growth (neoplasia), angiogenesis, including tumor angiogenesis, retinopathy including diabetic retinopathy, arthritis, including rheumatoid arthritis, smooth muscle cell migration and restenosis by administering a therapeutically effective amount of a compound of the Formula I–VI to achieve such inhibition together with a pharmaceutically acceptable carrier.

The following is a list of definitions of various terms used herein:

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon-carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The term "cycloalkyl" as used herein means saturated or partially unsaturated cyclic carbon radicals containing 3 to about 8 carbon atoms and more preferably 4 to about 6 carbon atoms. Examples of such cycloalkyl radicals include cyclopropyl, cyclopropenyl, cyclobutyl, cyclopentyl, cyclohexyl, 2-cyclohexen-1-yl, and the like.

The term "aryl" as used herein denotes aromatic ring systems composed of one or more aromatic rings. Preferred aryl groups are those consisting of one, two or three aromatic rings. The term embraces aromatic radicals such as phenyl, pyridyl, naphthyl, thiophene, furan, biphenyl and the like.

As used herein, the term "cyano" is represented by a radical of the formula

As used herein, the term "N-substituted pyrrolidinyl" refers to a radical of the formula

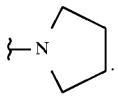

As used herein the term "N-substituted piperidinyl" refers to a radical of the formula

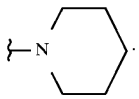

The term "morpholinyl as used herein refers to a radical of the formula

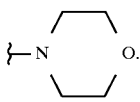

The terms "hydroxy" and "hydroxyl" as used herein are synonymous and are represented by a radical of the formula

The term "lower alkylene" or "alkylene" as used herein refers to divalent linear or branched saturated hydrocarbon radicals of 1 to about 6 carbon atoms.

As used herein the term "alkoxy" refers to straight or branched chain oxy containing radicals of the formula $-OR^{20}$, wherein $R^{20}$ is an alkyl group as defined above. Examples of alkoxy groups encompassed include methoxy, ethoxy, n-propoxy, n-butoxy, isopropoxy, isobutoxy, sec-butoxy, t-butoxy and the like.

As used herein the terms "arylalkyl" or "aralkyl" refer to a radical of the formula

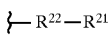

wherein $R^{21}$ is aryl as defined above and $R^{22}$ is an alkylene as defined above. Examples of aralkyl groups include benzyl, pyridylmethyl, naphthylpropyl, phenethyl and the like.

As used herein the terms "aralkyloxy" or "arylalkoxy" refer to a radical of the formula $-OR^{54}$ wherein $R^{54}$ is aralkyl as defined above.

As used herein the term "nitro" is represented by a radical of the formula

As used herein the term "halo" or "halogen" refers to bromo, chloro, fluoro or iodo.

As used herein the term "haloalkyl" refers to alkyl groups as defined above substituted with one or more of the same or different halo groups at one or more carbon atom. Examples of haloalkyl groups include trifluoromethyl, dichloroethyl, fluoropropyl and the like.

As used herein the term "carboxyl" or "carboxy" refers to a radical of the formula —COOH.

As used herein the term "carboxyl derivative" refers to a radical of the formula

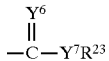

wherein $Y^6$ and $Y^7$ are independently selected from the group consisting of O, N or S and $R^{23}$ is selected from the group consisting of H, alkyl, aralkyl or aryl as defined above.

As used herein the term "amino" is represented by a radical of the formula $-NH_2$.

As used herein the term "aminoalkyl" refers to a radical of the formula

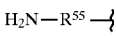

wherein $R^{55}$ is alkyl as defined above.

As used herein the term "alkylsulfonyl" or "alkylsulfone" refers to a radical of the formula

wherein $R^{24}$ is alkyl as defined above.

As used herein the term "alkylthio" refers to a radical of the formula $-SR^{24}$ wherein $R^{24}$ is alkyl as defined above.

As used herein the term "sulfonic acid" refers to a radical of the formula

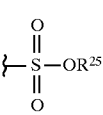

wherein $R^{25}$ is H, alkyl or aryl as defined above.

As used herein the term "sulfonamide" refers to a radical of the formula

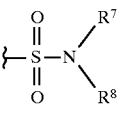

wherein $R^7$ and $R^8$ are as defined above.

As used herein the term "fused aryl" refers to an aromatic ring such as the aryl groups defined above fused to one or more phenyl rings. Embraced by the term "fused aryl" is the radical naphthyl.

As used herein the terms "monocyclic heterocycle" or "monocyclic heterocyclic" refer to a monocyclic ring containing from 4 to about 12 atoms, and more preferably from 5 to about 10 atoms, wherein 1 to 3 of the atoms are heteroatoms selected from the group consisting of oxygen, nitrogen and sulfur with the understanding that if two or more different heteroatoms are present at least one of the heteroatoms must be nitrogen. Representative of such monocyclic heterocycles are imidazole, furan, pyridine, oxazole, pyran, triazole, thiophene, pyrazole, thiazole, thiadiazole, and the like.

As used herein the term "fused monocyclic heterocycle" refers to a monocyclic heterocycle as defined above with a benzene fused thereto. Examples of such fused monocyclic heterocycles include benzofuran, benzopyran, benzodioxole, benzothiazole, benzothiophene, benzimidazole and the like.

As used herein the term "methylenedioxy" refers to the radical

and the term "ethylenedioxy" refers to the radical

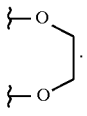

As used herein the term "4–12 membered dinitrogen containing heterocycle refers to a radical of the formula

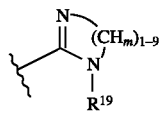

wherein m is 1 or 2 and $R^{19}$ is H, alkyl, aryl, or aralkyl and more preferably refers to 4–9 membered ring and includes rings such as imidazoline, pyrimidine, and the like.

As used herein the term "5-membered heteroaromatic ring" includes for example a radical of the formula

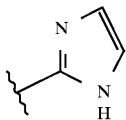

and "5-membered heteroaromatic ring fused with a phenyl" refers to such a "5-membered heteroaromatic ring" with a phenyl fused thereto. Representative of such 5-membered heteroaromatic rings fused with a phenyl is benzimidazole.

As used herein the term "bicycloalkyl" refers to a bicyclic hydrocarbon radical containing 6 to about 12 carbon atoms which is saturated or partially unsaturated.

As used herein the term "acyl" refers to a radical of the formula

wherein $R^{26}$ is alkyl, alkenyl, alkynyl, aryl or aralkyl as defined above. Encompassed by such radical are the groups acetyl, benzoyl and the like.

As used herein the term "thio" refers to a radical of the formula

As used herein the term "sulfonyl" refers to a radical of the formula

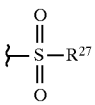

wherein $R^{27}$ is alkyl, aryl or aralkyl as defined above.

As used herein the term "haloalkylthio" refers to a radical of the formula —S—$R^{28}$ wherein $R^{28}$ is haloalkyl as defined above.

As used herein the term "aryloxy" refers to a radical of the formula

wherein $R^{29}$ is aryl as defined above.

As used herein the term "acylamino" refers to a radical of the formula

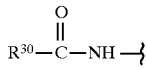

wherein $R^{30}$ is alkyl, aralkyl or aryl as defined above.

As used herein the term "amido" refers to a radical of the formula

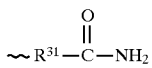

wherein $R^{31}$ is a bond or alkylene as defined above.

As used herein the term "alkylamino" refers to a radical of the formula —NH$R^{32}$ wherein $R^{32}$ is alkyl as defined above.

As used herein the term "dialkylamino" refers to a radical of the formula —N$R^{33}R^{34}$ wherein $R^{33}$ and $R^{34}$ are the same or different alkyl groups as defined above.

As used herein the term "trifluoromethyl" refers to a radical of the formula

As used herein the term "trifluoroalkoxy" refers to a radical of the formula

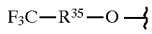

wherein $R^{35}$ is a bond or an alkylene as defined above.

As used herein the term "alkylaminosulfonyl" refers to a radical of the formula

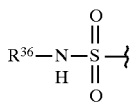

wherein $R^{36}$ is alkyl as defined above.

As used herein the term "alkylsulfonylamino" refers to a radical of the formula

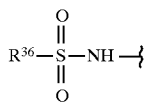

wherein $R^{36}$ is alkyl as defined above.

As used herein the term "trifluoromethylthio" refers to a radical of the formula

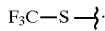

As used herein the term "trifluoromethylsulfonyl" refers to a radical of the formula

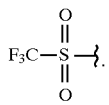

As used herein the term "4–12 membered mono-nitrogen containing monocyclic or bicyclic ring" refers to a saturated or partially unsaturated monocyclic or bicyclic ring of 4–12 atoms and more preferably a ring of 4–9 atoms wherein one atom is nitrogen. Such rings may optionally contain additional heteroatoms selected from nitrogen, oxygen or sulfur. Included within this group are morpholine, piperidine, piperazine, thiomorpholine, pyrrolidine, proline, azacycloheptene and the like.

As used herein the term "benzyl" refers to the radical

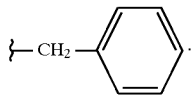

As used herein the term "phenethyl" refers to the radical

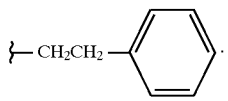

As used herein the term "4–12 membered mono-nitrogen containing sulfur or oxygen containing heterocyclic ring" refers to a ring consisting of 4 to 12 atoms and more preferably 4 to 9 atoms wherein at least one atom is a nitrogen and at least one atom is oxygen or sulfur. Encompassed within this definition are rings such as thiazoline and the like.

As used herein the term "arylsulfonyl" or "arylsulfone" refers to a radical of the formula

wherein $R^{37}$ is aryl as defined above.

As used herein the terms "alkylsulfoxide" or "arylsulfoxide" refer to radicals of the formula

wherein $R^{38}$ is, respectively, alkyl or aryl as defined above.

As used herein the term "phosphonic acid derivative" refers to a radical of the formula

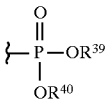

wherein $R^{39}$ and $R^{40}$ are the same or different H, alkyl, aryl or aralkyl.

As used herein the term "phosphinic acid derivatives" refers to a radical of the formula

wherein $R^{41}$ is H, alkyl, aryl or aralkyl as defined above.

As used herein the term "arylthio" refers to a radical of the formula

wherein $R^{42}$ is aryl as defined above.

As used herein the term "monocyclic heterocycle thio" refers to a radical of the formula

wherein $R^{43}$ is a monocyclic heterocycle radical as defined above.

As used herein the terms "monocyclic heterocycle sulfoxide" and "monocyclic heterocycle sulfone" refer, respectively, to radicals of the formula

and

wherein $R^{43}$ is a monocyclic heterocycle radical as defined above.

As used herein the phrase "B is CONR" wherein R" taken together with $Z^4$ forms a 5 or 6-membered ring fused to the phenyl" refers to a radical of the formula

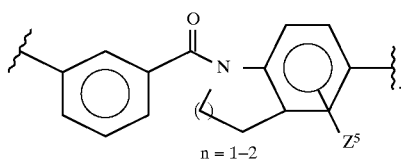

n = 1–2

The term "composition" as used herein means a product which results from the mixing or combining of more than one element or ingredient.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:

$^1$H-NMR=proton nuclear magnetic resonance
AcOH=acetic acid
$BH_3$-THF=borane-tetrahydrofuran complex
BOC=tert-butoxycarbonyl
Cat.=catalytic amount
$CH_2Cl_2$=dichloromethane
$CH_3CN$=acetonitrile
$CH_3I$=iodomethane
CHN analysis=carbon/hydrogen/nitrogen elemental analysis
CHNCl analysis=carbon/hydrogen/nitrogen/chlorine elemental analysis
CHNS analysis=carbon/hydrogen/nitrogen/sulfur elemental analysis
DCC=1,3-dicyclohexylcarbodiimide
DIEA=diisopropylethylamine
DMA=N,N-dimethylacetamide
DMAP=4-(N,N-dimethylamino)pyridine
DMF=N,N-dimethylformamide
DSC=disuccinyl carbonate
EDCI=1-(3-dimethylaminopropyl)-3-ethylcarbodiimide hydrochloride
$Et_2O$=diethyl ether
$Et_3N$=triethylamine
EtOAc=ethyl acetate
EtOH=ethanol
FAB MS=fast atom bombardment mass spectroscopy
g=gram(s)
GIHA HCl=meta-guanidino-hippuric acid hydrochloride
GIHA=meta-guanidino-hippuric acid
HPLC=high performance liquid chromatography
IBCF=isobutylchloroformate
$K_2CO_3$=potassium carbonate
KOH=potassium hydroxide
LiOH=lithium hydroxide
MCPBA=m-chloroperoxybenzoic acid or m-chloroperbenzoic acid
MeOH=methanol
MesCl=methanesulfonylchloride mg=milligram
$MgSO_4$=magnesium sulfate
ml=milliliter
mL=milliliter
MS=mass spectroscopy
$N_2$=nitrogen
$NaCNBH_3$=sodium cyanoborohydride
$Na_2PO_4$=sodium phosphate
$Na_2SO_4$=sodium sulfate
$NaHCO_3$=sodium bicarbonate
NaOH=sodium hydroxide
$NH_4HCO_3$=ammonium bicarbonate
$NH_4^+HCO_2$=ammonium formate
NMM=N-methyl morpholine
NMR=nuclear magnetic resonance
RPHPLC=reverse phase high performance liquid chromatography
RT=room temperature
KSCN=potassium thiocyanate
Pd/C=palladium on carbon
Bn=benzyl
Et=ethyl
Me=methyl
Ph=phenyl
$NEt_3$=triethylamine
t-BOC=tert-butoxycarbonyl
TFA=trifluoroacetic acid
THF=tetrahydrofuran
Δ=heating the reaction mixture As used herein HPLC-Method 1 refers to reverse phase C-18 functionalized silica gel column (50×300 mm) using a linear gradient of 95% 0.6% TFA/water:5% $CH_3CN$ to 60% 0.6% TFA/water: 40% $CH_3CN$ with a flow rate of 80 ml/minute.

The compounds as shown in Formulas I–VI can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of Formula I with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, tartrate salts and the like. All of the pharmacologically acceptable salts can be prepared by conventional means. (See Berge et al., J Pharm. Sci., 66(1), 1–19 (1977) for additional examples of pharmaceutically acceptable salts.) For the selective inhibition or antagonism of $\alpha_v\beta_3$ integrins, compounds of the present invention can be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by selectively inhibiting or antagonizing the $\alpha_v\beta_3$ cell surface receptor which method comprises administering a therapeutically effective amount of a compound selected from the class of compounds depicted in Formulas I–VI, wherein one or more compounds of the Formulas I–VI is administered in association with one or more non-toxic, pharmaceutically acceptable carriers and/or diluents and/or adjuvants (collectively referred to herein as "carrier" materials) and if desired other active ingredients. More specifically, the present invention provides a method for inhibition of the $\alpha_v\beta_3$ cell surface receptor. Most preferably the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, inhibiting arthritis, psoriasis and periodontal disease, and inhibiting smooth muscle cell migration including restenosis.

Based upon standard laboratory experimental techniques and procedures well known and appreciated by those skilled in the art, as well as comparisons with compounds of known usefulness, the compounds of Formula I can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

Treatment of a patient afflicted with one of the pathological conditions comprises administering to such a patient an amount of compound of the Formula I which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

As stated previously, the compounds of the invention can be used in a variety of biological, prophylactic or therapeutic areas. It is contemplated that these compounds are useful in prevention or treatment of any disease state or condition wherein the $\alpha_v\beta_3$ integrin plays a role.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 1000 mg per kilogram of body weight per day and more preferably 0.01 mg to about 100 mg per kilogram are useful in the treatment of the above-indicated conditions.

The active ingredient administered by injection is formulated as a composition wherein, for example, saline, dextrose or water can be used as a suitable carrier. A suitable daily dose would typically be about 0.01 to 10 mg/kg body weight injected per day in multiple doses depending on the factors listed above.

For administration to a mammal in need of such treatment, the compounds in a therapeutically effective amount are ordinarily combined with one or more adjuvants appropriate to the indicated route of administration. The compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention can be subjected to conventional pharmaceutical operations such as sterilization and/or may contain conventional pharmaceutical adjuvants such as preservatives, stabilizers, wetting agents, emulsifiers, buffers, etc.

The general synthetic sequences for preparing the compounds useful in the present invention are outlined in Schemes I–III. Both an explanation of, and the actual procedures for, the various aspects of the present invention are described where appropriate. The following Schemes and Examples are intended to be merely illustrative of the present invention, and not limiting thereof in either scope or spirit. Those of skill in the art will readily understand that known variations of the conditions and processes described in the Schemes and Examples can be used to perform the process of the present invention.

Unless otherwise indicated all starting materials and equipment employed were commercially available.

SCHEME I
(A)
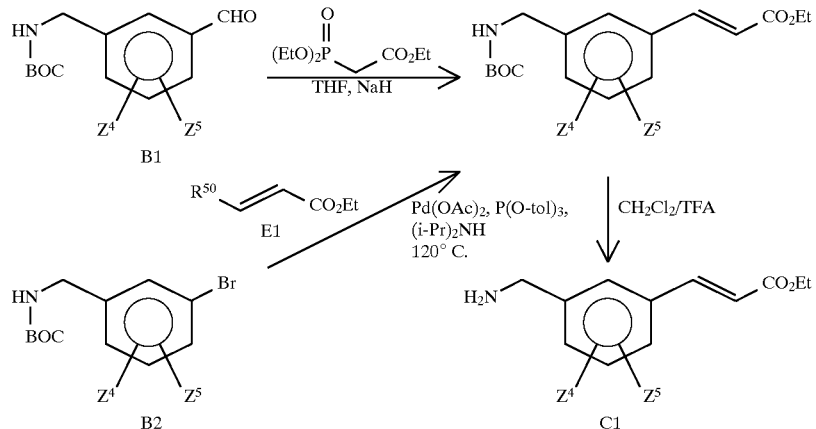
(B)
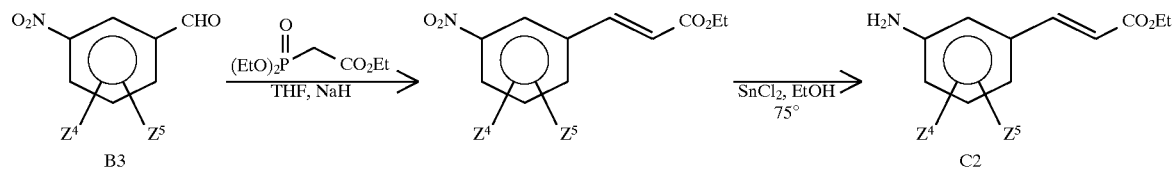
(C)
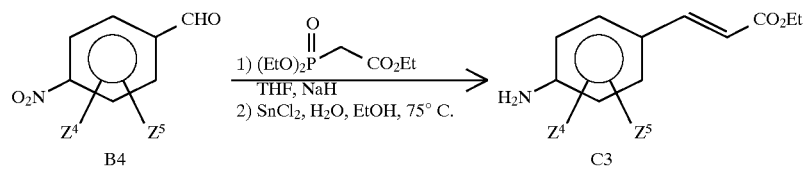
(D)
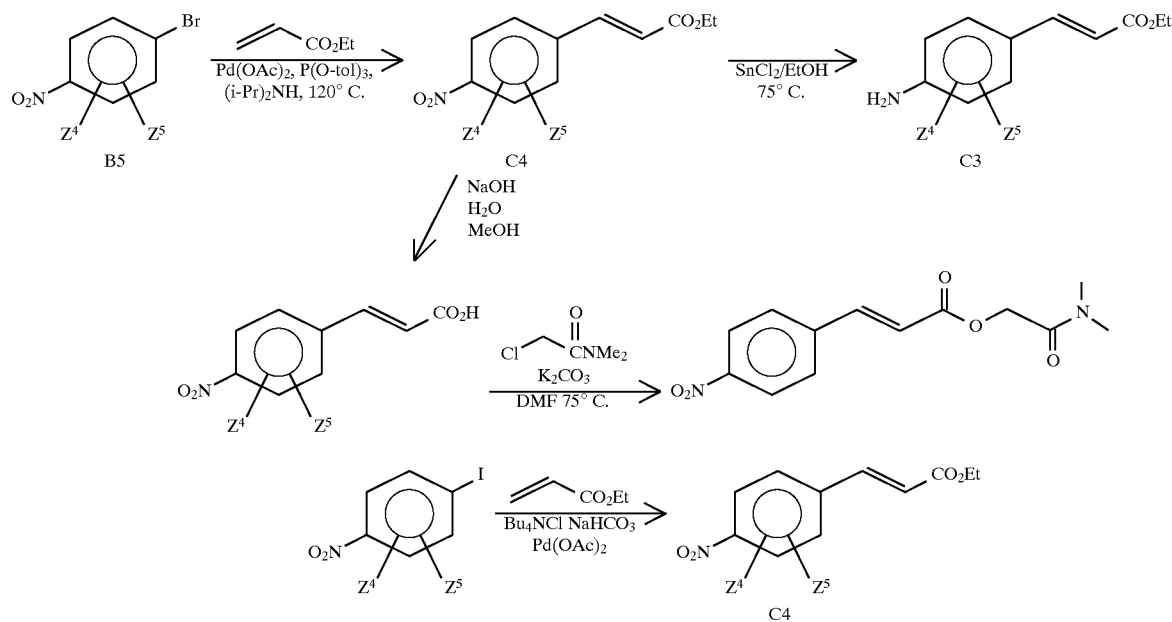

SCHEME I -continued
(E)
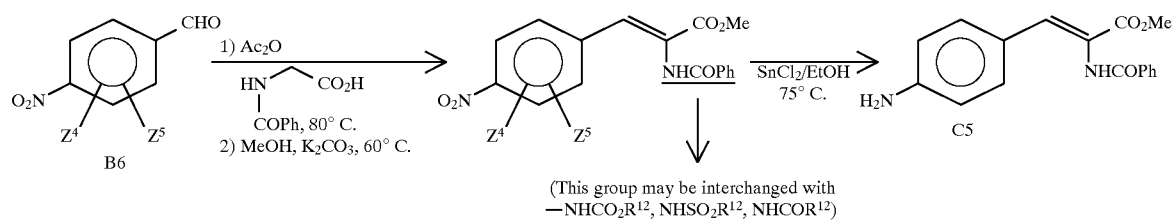
(F)
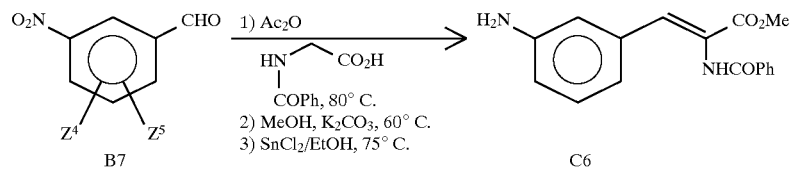
(G)
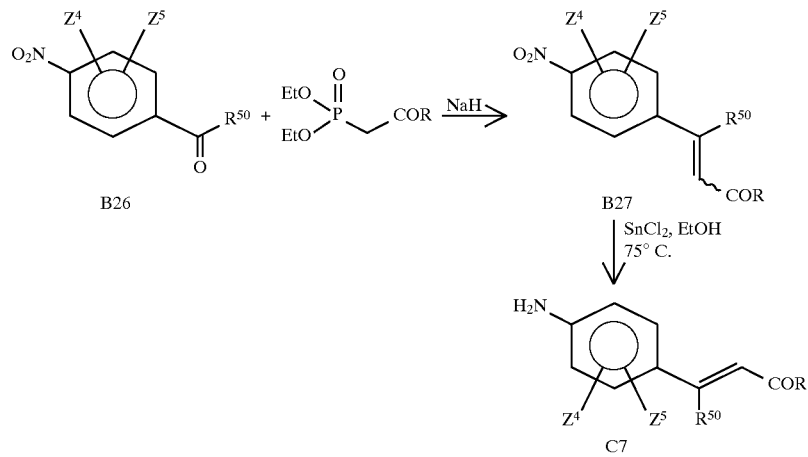
(H)
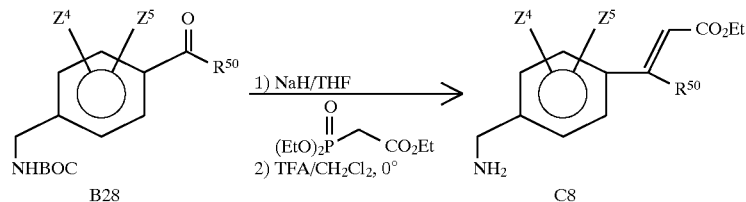

SCHEME I
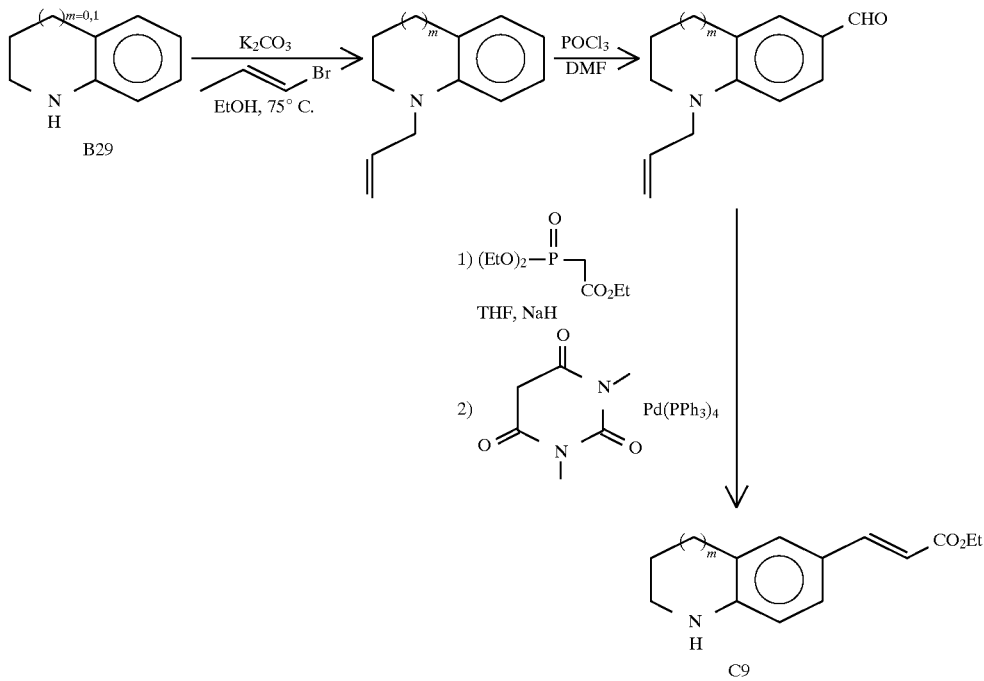
SCHEME II
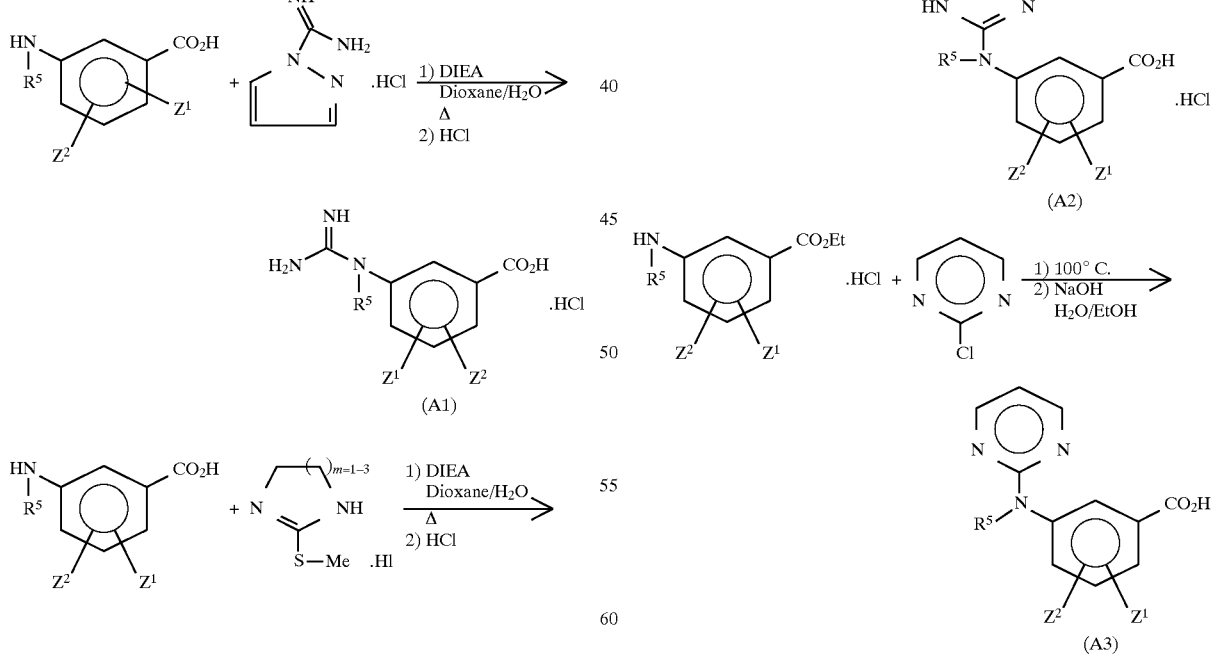

-continued
SCHEME II
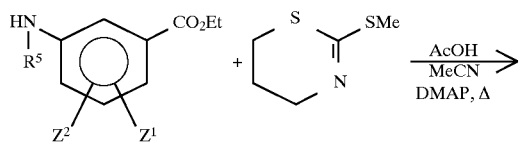
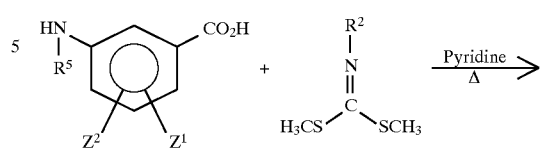
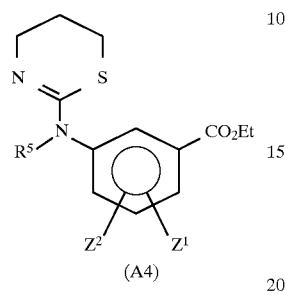
(A4)
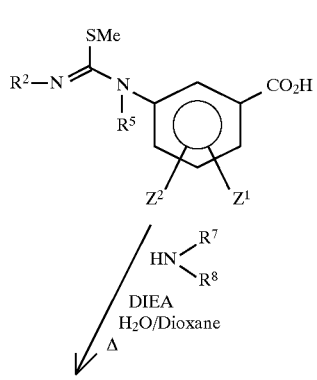
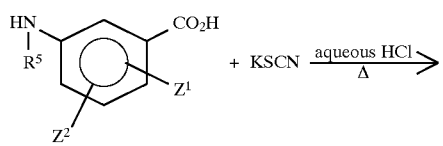
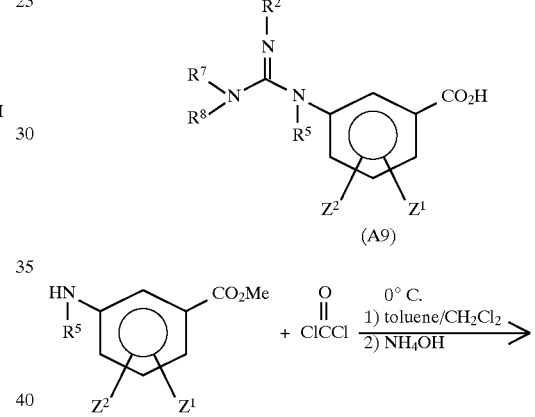
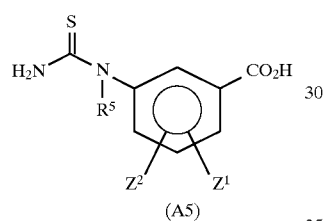
(A9)
(A5)
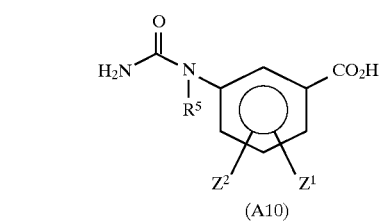
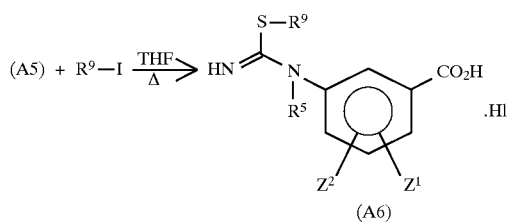
(A10)
(A6)
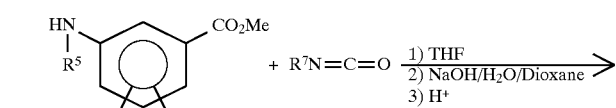
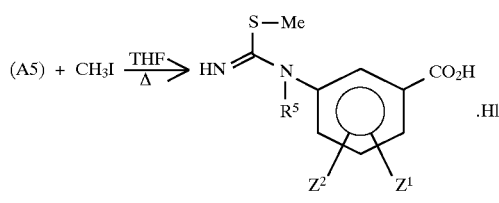
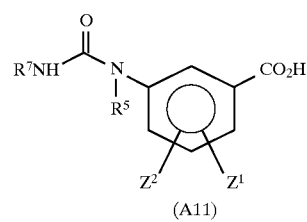
(A7)
(A11)
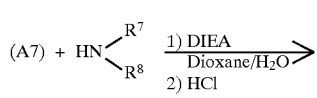
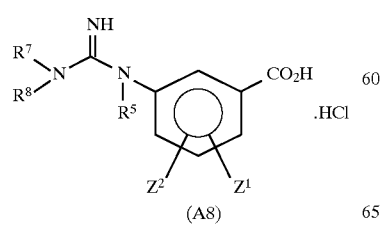
(A8)

-continued
SCHEME II
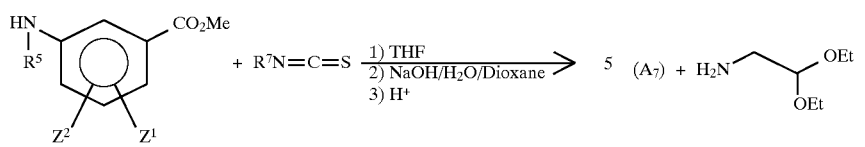
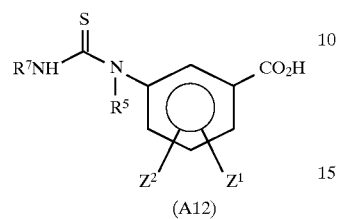
(A12)
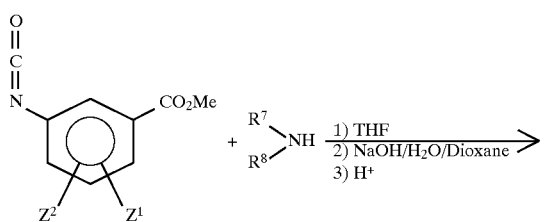
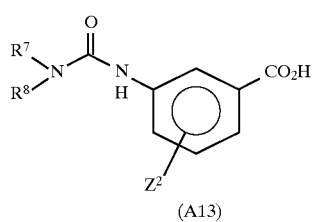
(A13)
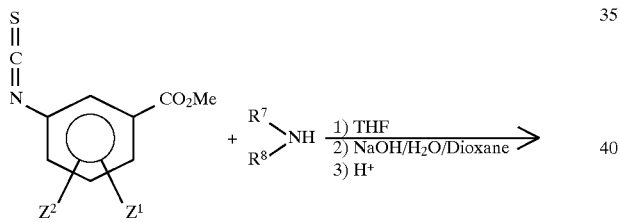
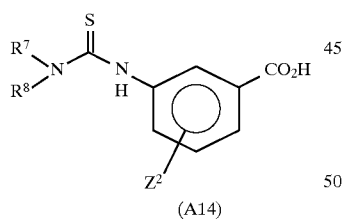
(A14)
-continued
SCHEME II
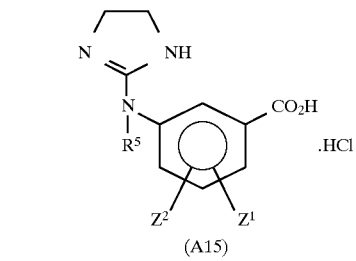
(A15)
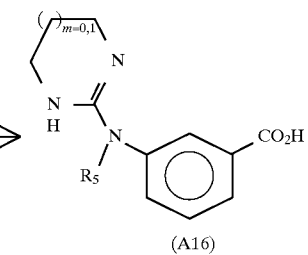
(A16)
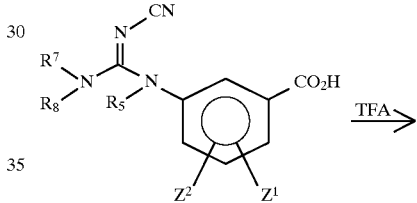
(A17)

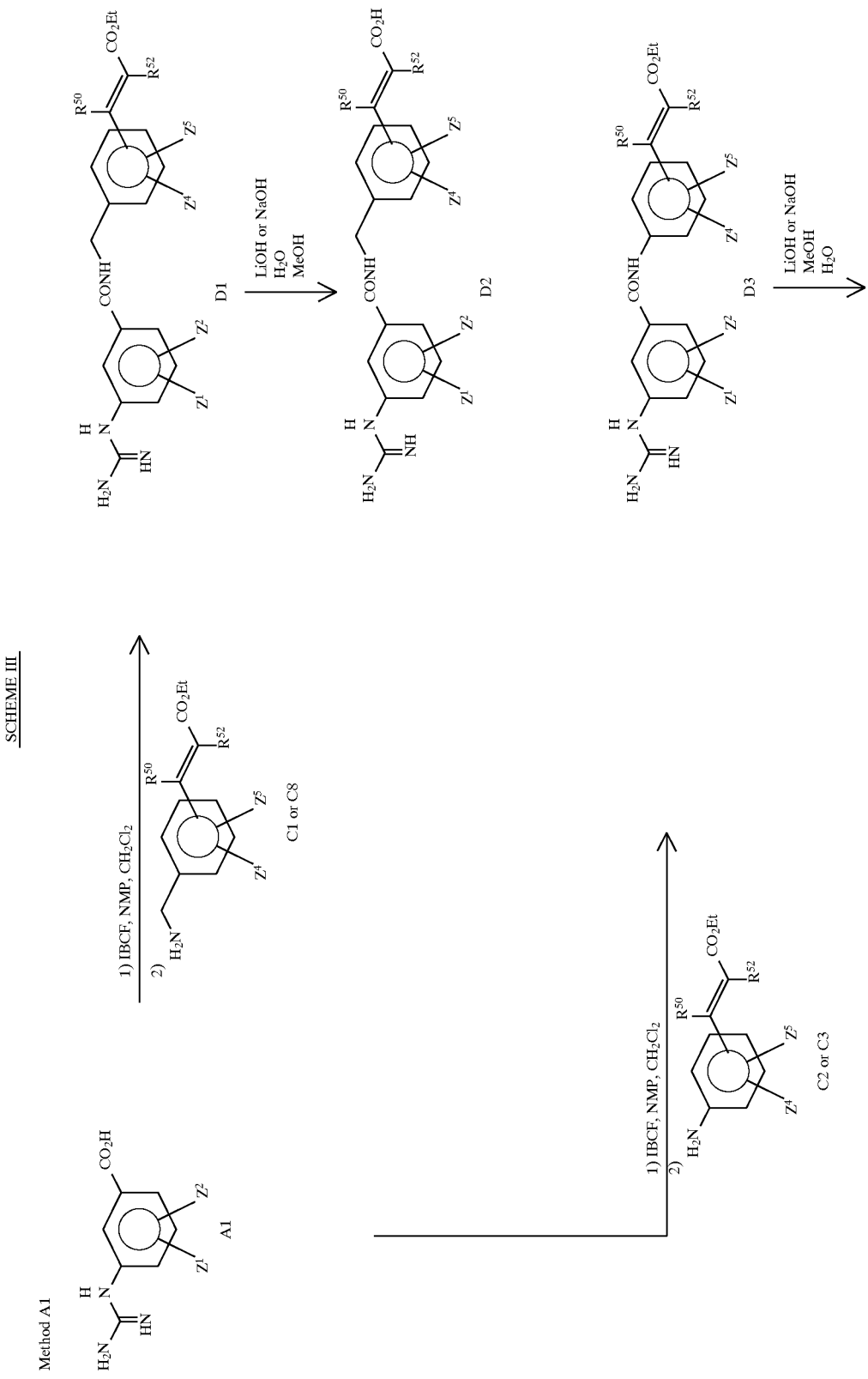

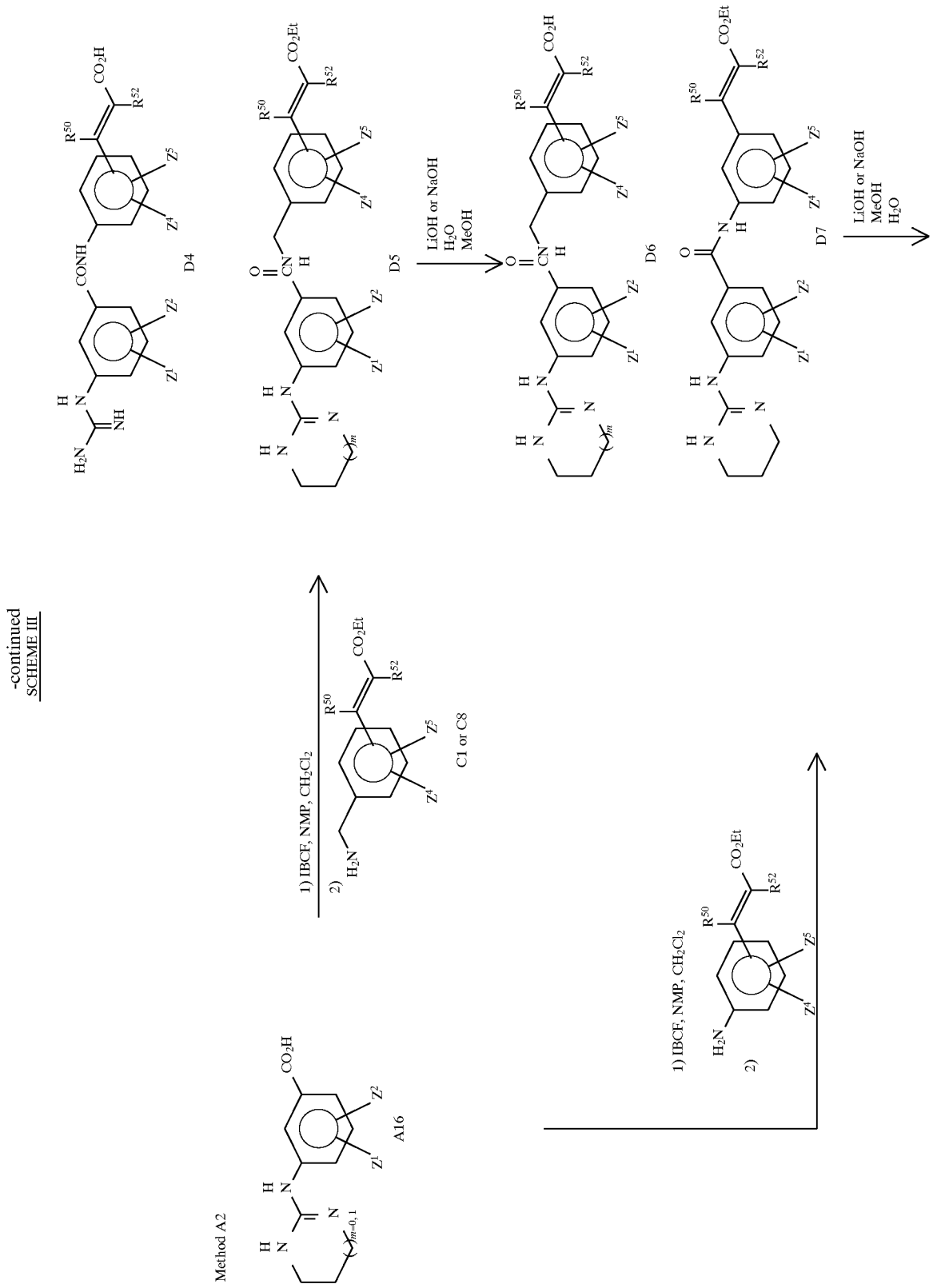

-continued
SCHEME III
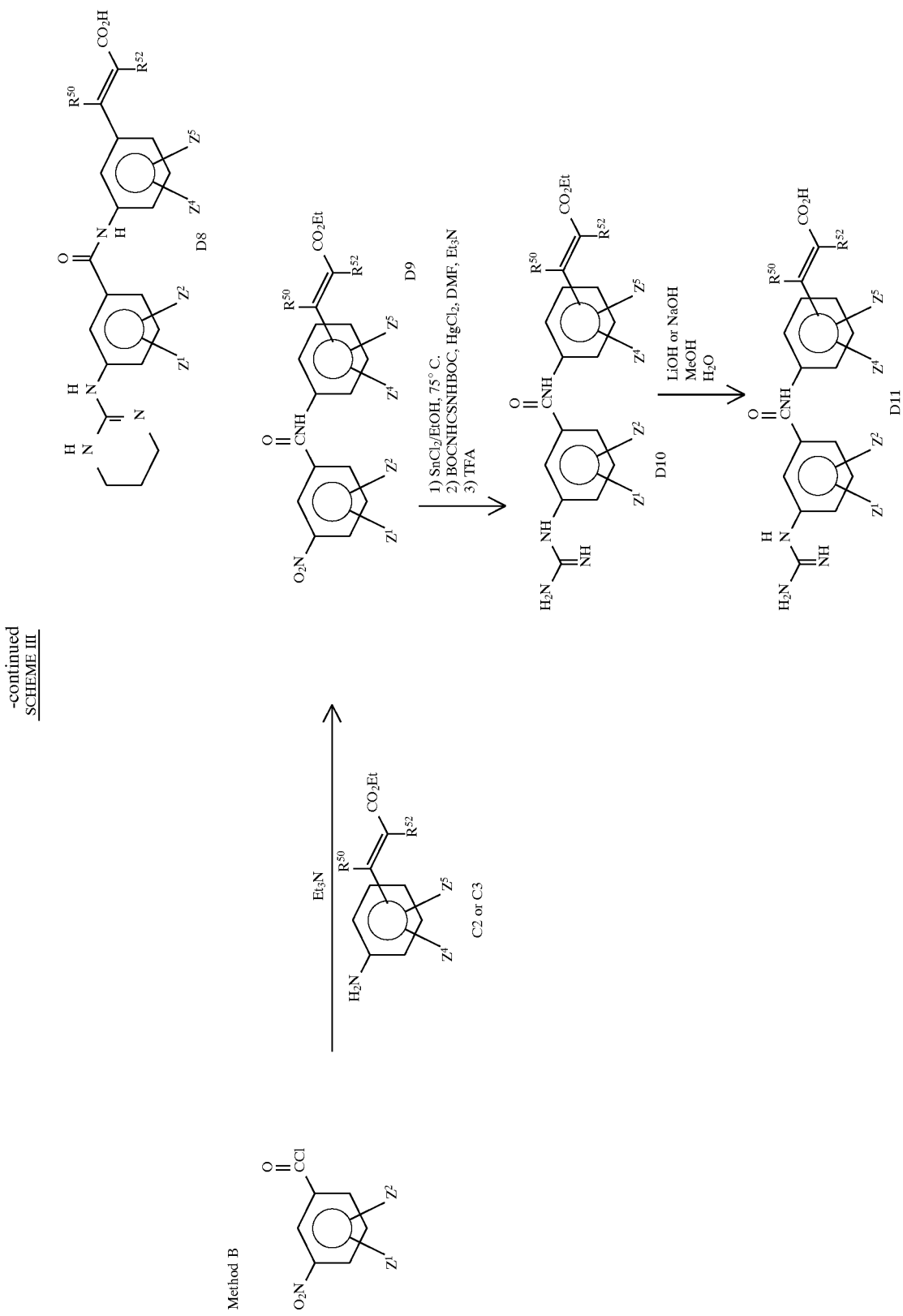

-continued
SCHEME III
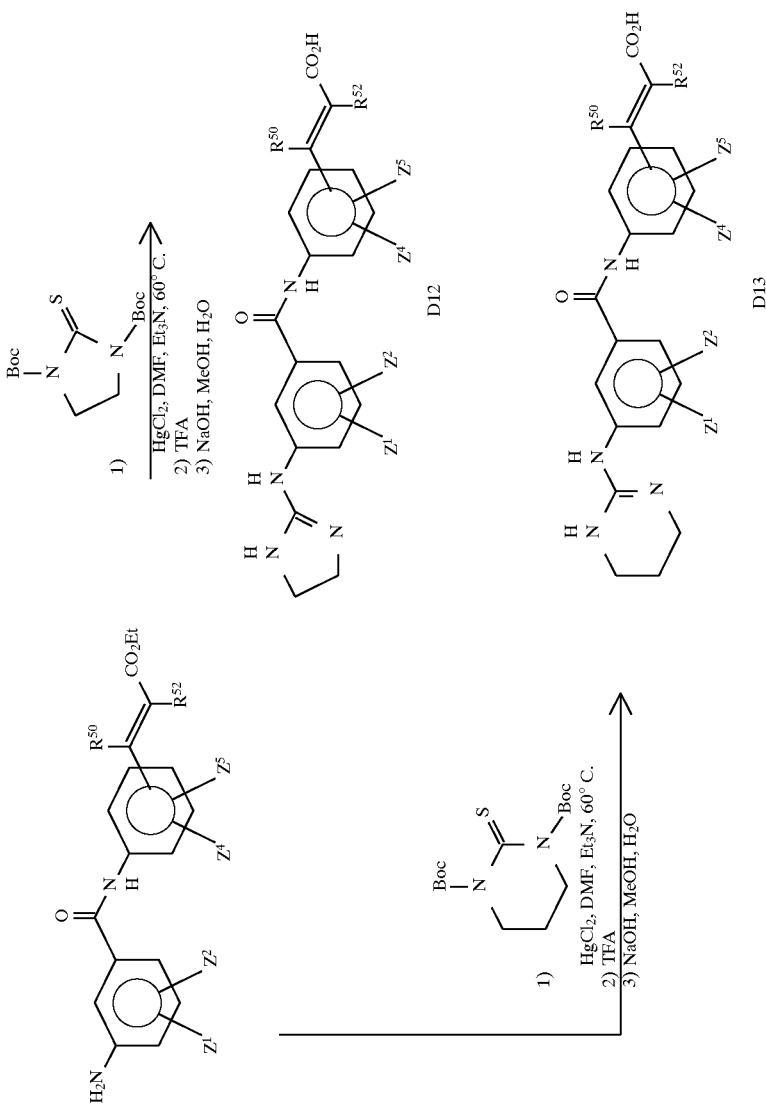
Method C

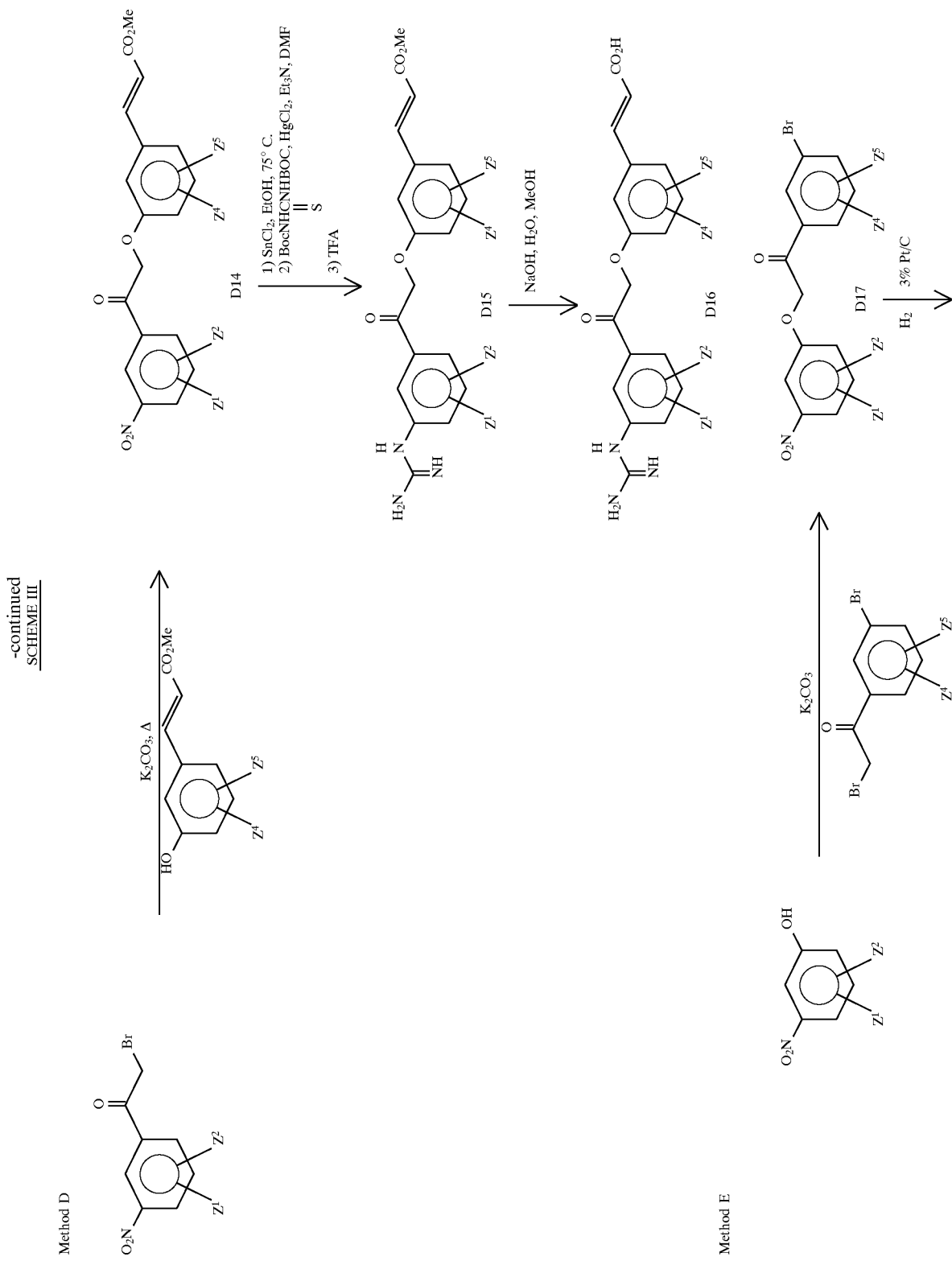

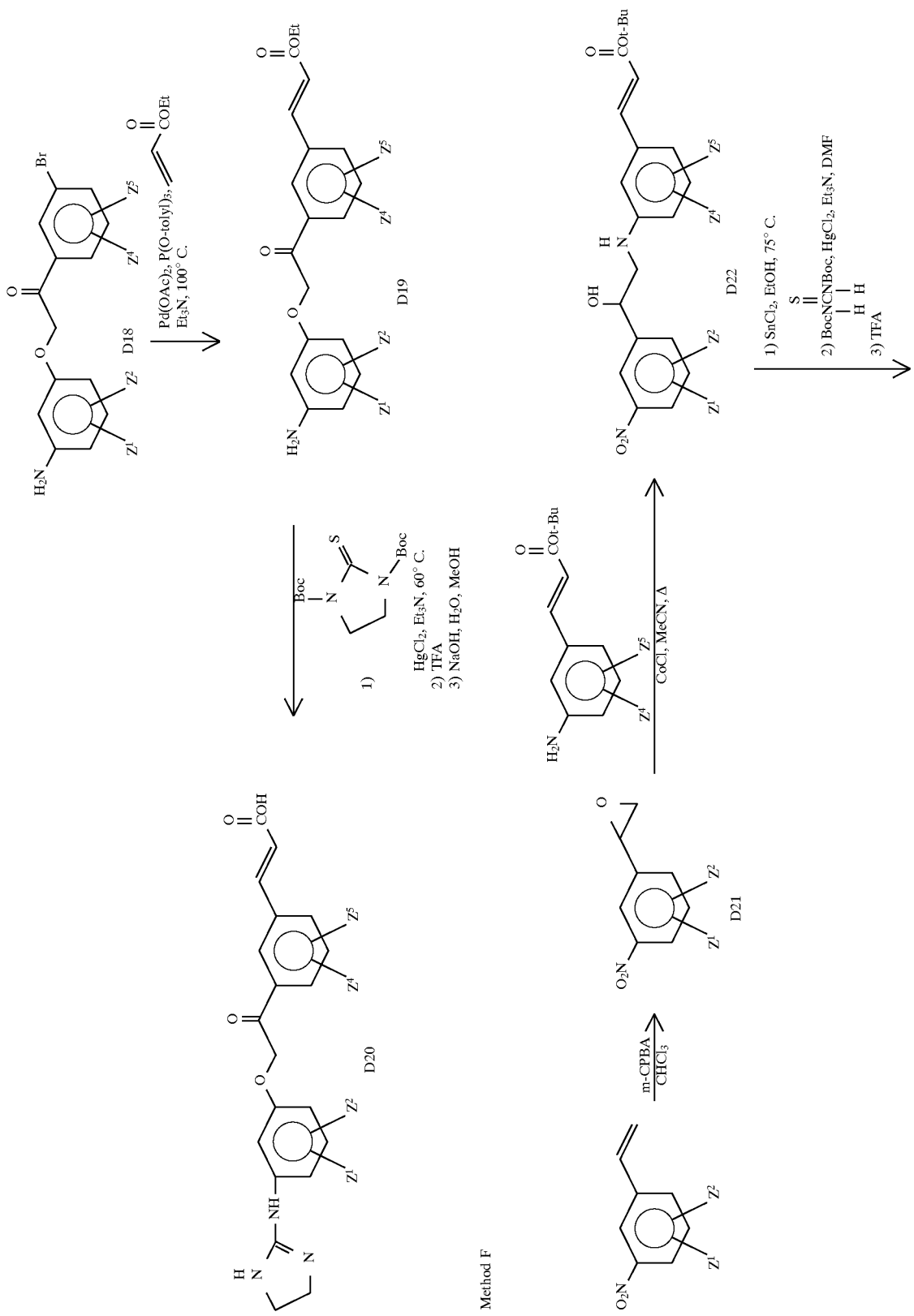

-continued
SCHEME III
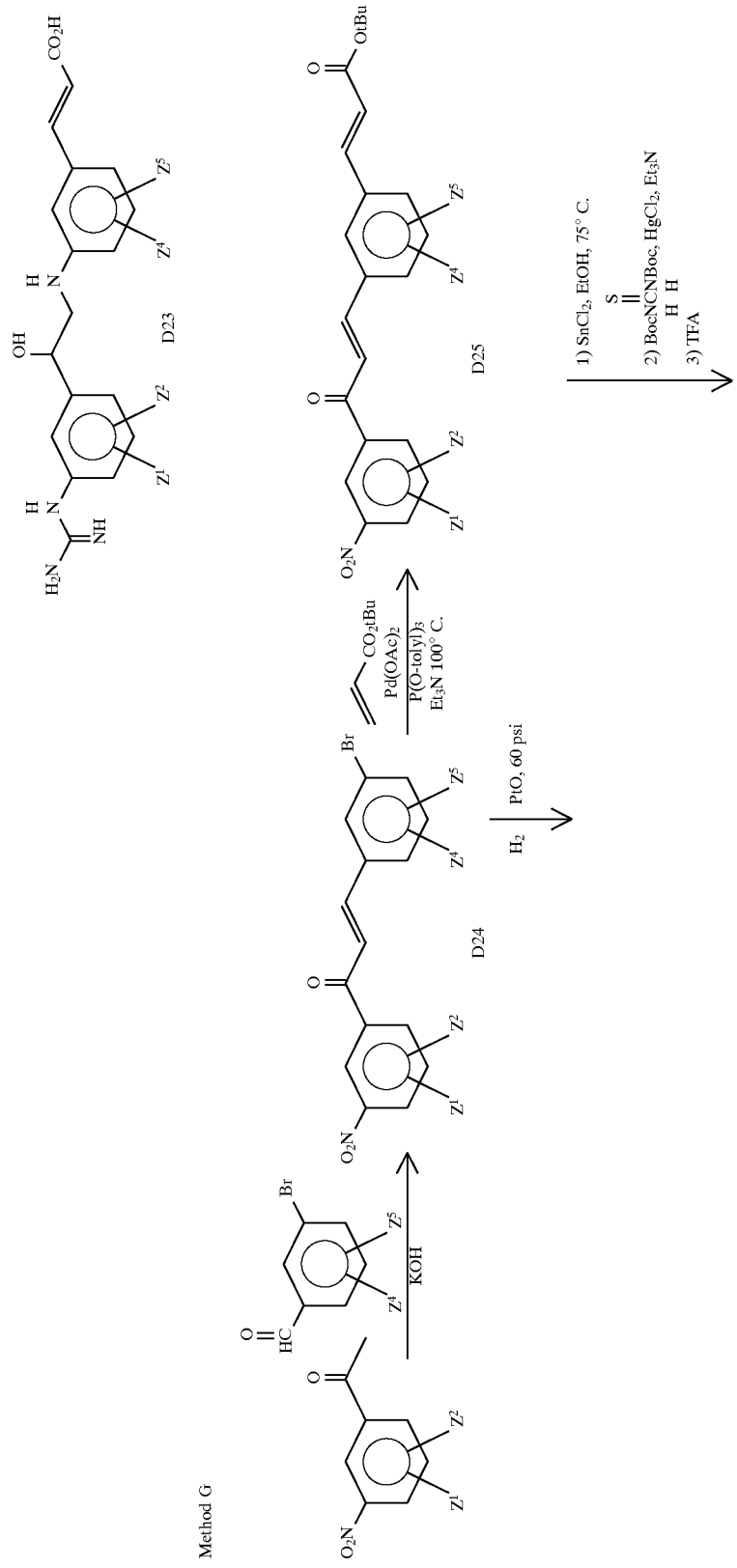
Method G

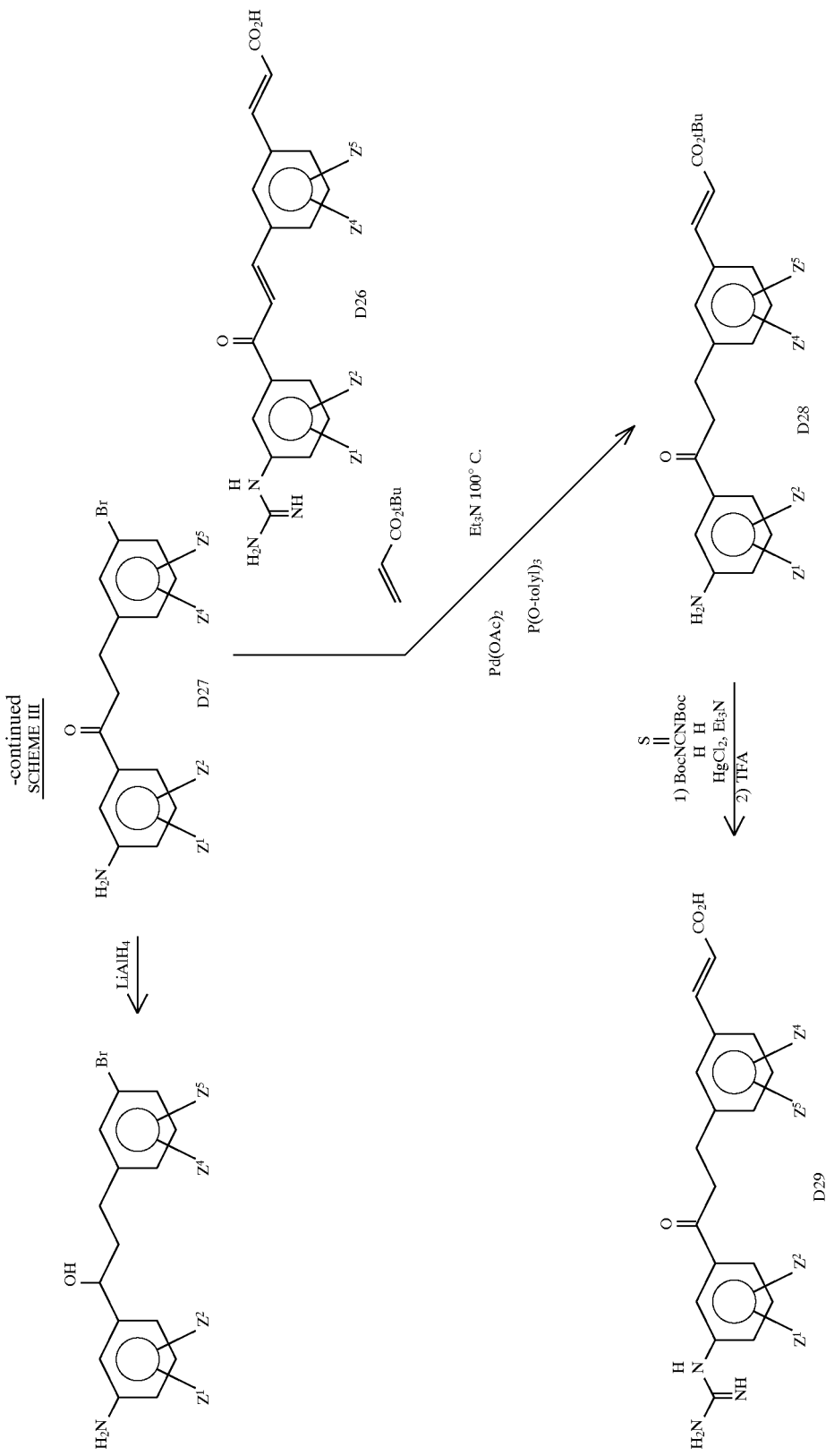

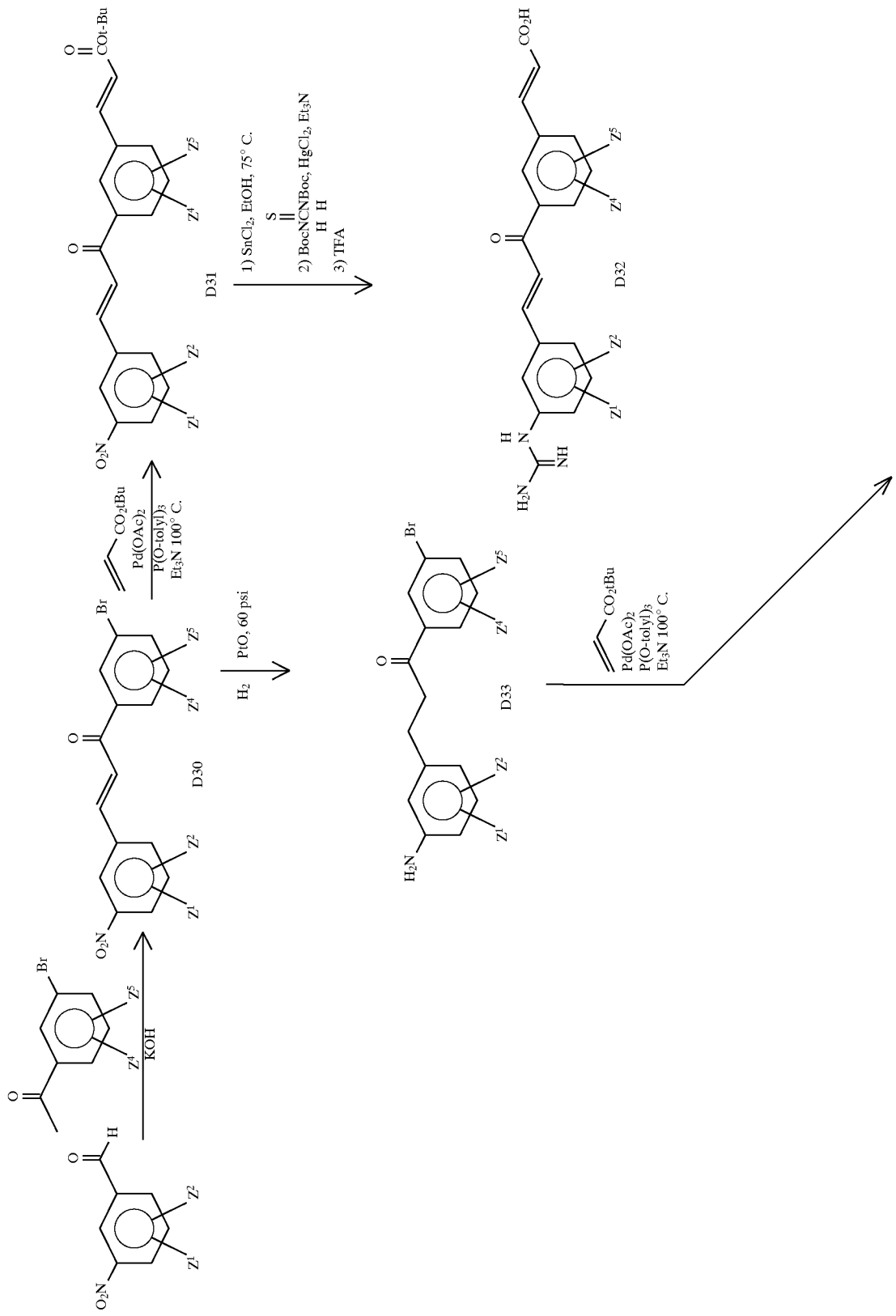

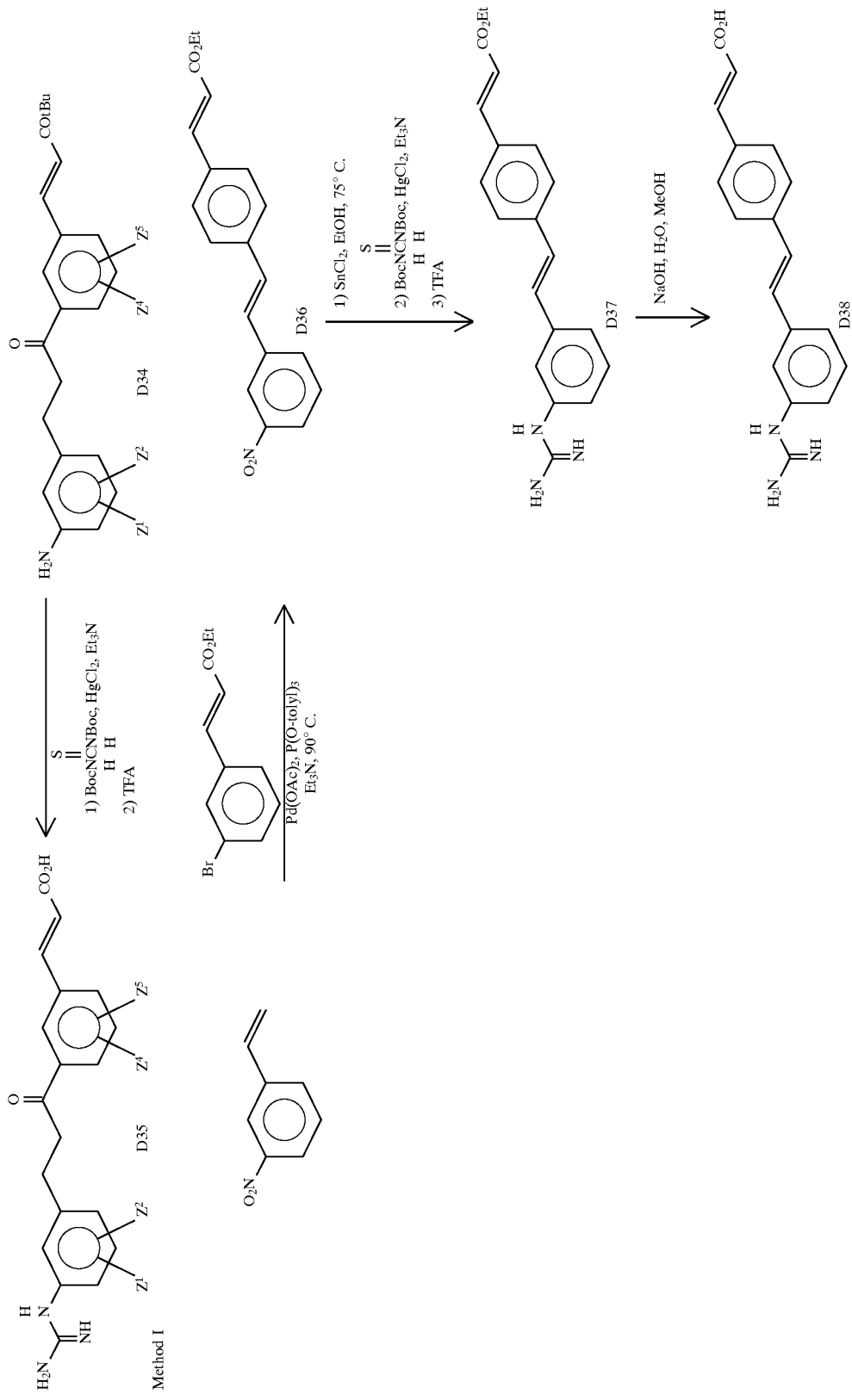

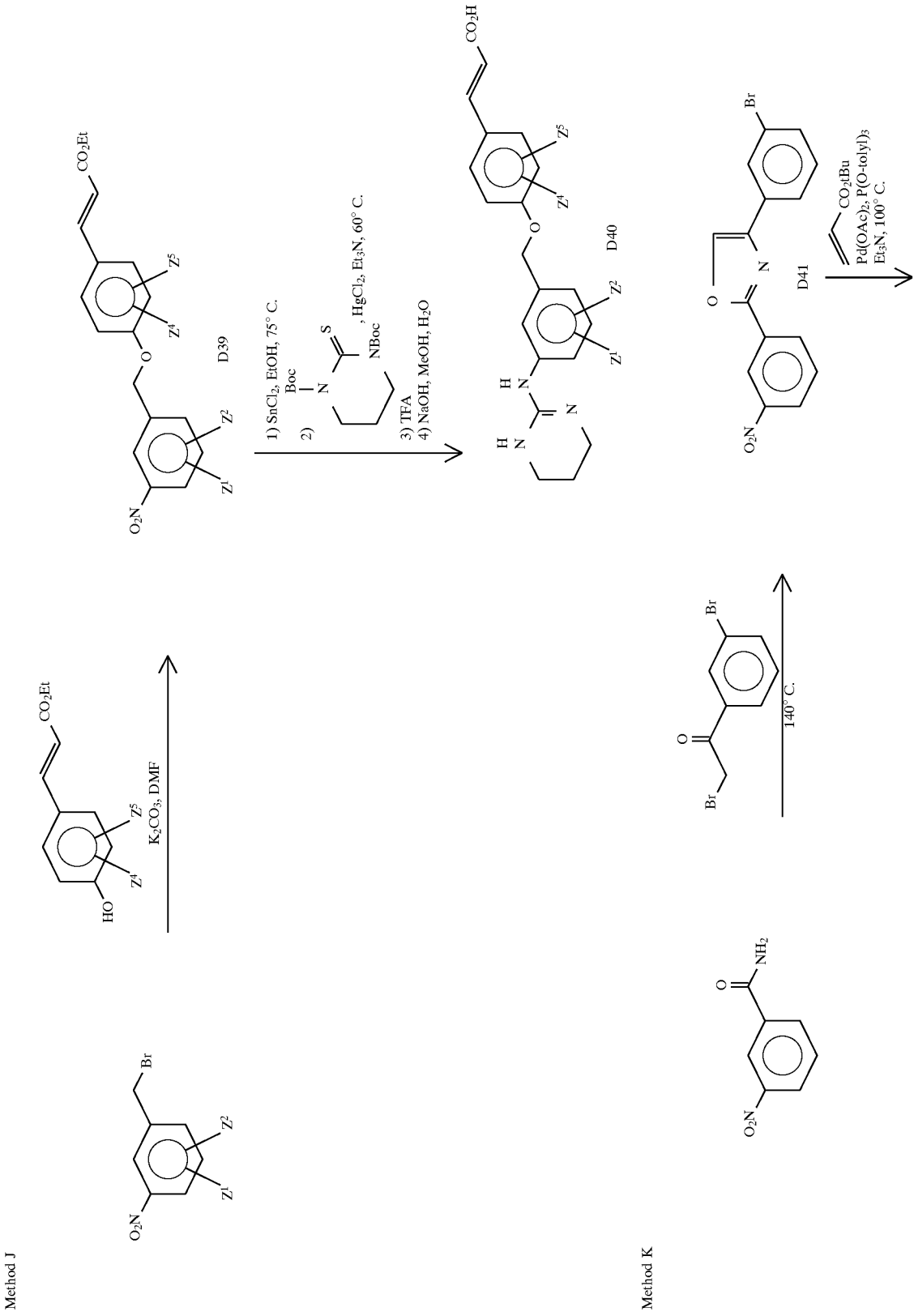

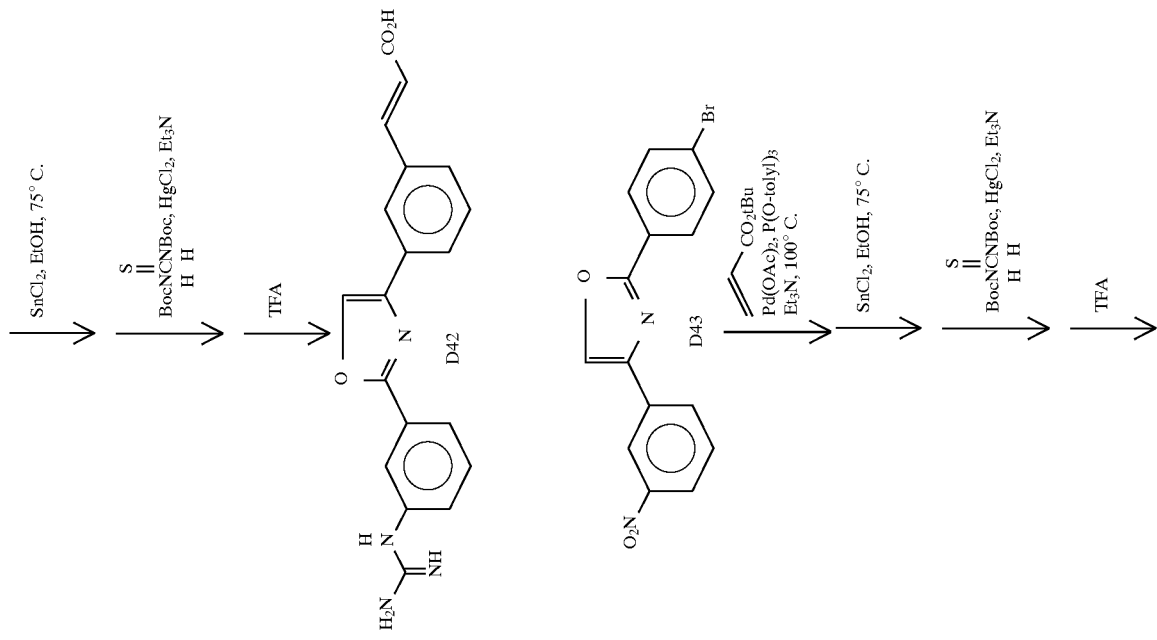
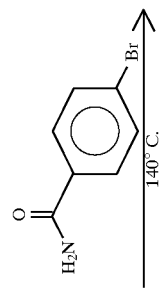
Method L

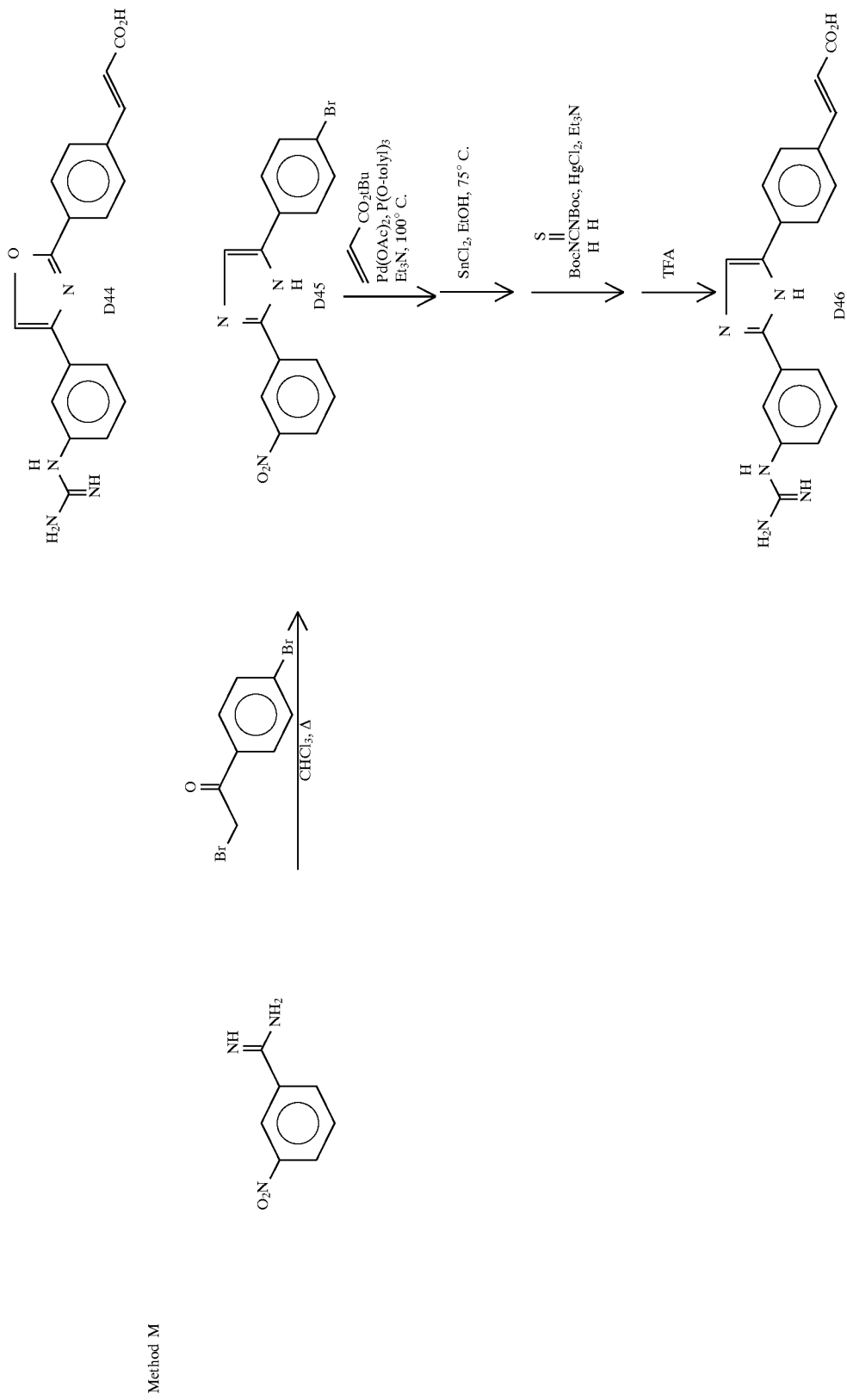
Method M

Schemes I–III are illustrative of methodology useful for preparing various compounds of the present invention. Such methodology is more specifically defined in the examples which follow. Such methodology can be modified by one skilled in the art, substituting known reagents and conditions from conventional methodology to produce the desired compounds.

In Scheme I(A) cinnamic ester C1 is readily prepared from either aldehyde B1 or bromide B2.

Aldehyde B1 is condensed with $(EtO)_2P(O)CH_2CO_2Et$ under standard conditions (NaH/THF, 0° to room temperature). The resulting alkene is readily deprotected (TFA, $CH_2Cl_2$) to afford the desired cinnamic ester C1.

In a complimentary procedure, bromide B2 can be coupled with ethyl acrylate E1 $(Pd(OAc)_2, P(O\text{-tolyl})_3, iPr_2NH, 120°\ C.)$ to afford the above mentioned cinnamic ester analog. Deprotection affords cinnamic ester C1 as described above.

In Scheme I(B) cinnamic ester C2 is readily prepared from aldehyde B3.

Aldehyde B3 is condensed with $(EtO)_2P(O)CH_2CO_2Et$ using standard conditions (NaH, THF, 0° to room temperature.) The resulting nitrophenylcinnamic ester derivative can be reduced ($SnCl_2$, $H_2O$, EtOH, 75°) to afford cinnamic ester C2.

In Scheme I(C) cinnamic ester C3 is readily prepared from aldehyde B4 using the reaction conditions described in Scheme I(B).

In Scheme I(D) cinnamic ester C3 can be prepared from bromide B5.

Bromide B5 can be coupled with alkyl acrylates using a standard Heck coupling procedure $(Pd(OAc)_2, P(O\text{-tol})_3, iPr_2NH, 120°\ C.)$ to afford a nitrocinnamic ester analog. Reduction of the resulting nitrocinnamic ester analog ($SnCl_2$, EtOH, 75° C.) leads to cinnamic ester C3.

In Scheme I(E) dehydroamino ester C5 can be prepared from aldehyde B6 as described below.

Aldehyde B6 is condensed with N-benzylglycine ($Ac_2O$, 80°) and the resulting azalactone is hydrolyzed (MeOH/$K_2CO_3$) to afford the corresponding dehydroamino ester analog. Reduction of the nitro aryl moiety (tin (II) chloride) would afford dehydroamino ester C5.

In Scheme I(F) in an analogous fashion to that described in Scheme I(E), aldehyde B7 may be converted into dehydroamino ester C6.

In Scheme I(G) in an analogous fashion to that described in Scheme I(B), aldehyde or ketone B26 may be converted into cinnamic ester C7.

In Scheme I(H) cinnamic ester C8 can be prepared from aldehyde or ketone B28 as described below.

Aldehyde or ketone B28 is condensed with $(EtO)_2P(O)CH_2CO_2Et$ under standard conditions (NaH, THF, 0° to room temperature.) The resulting BOC-protected cinnamic ester derivative can be deprotected (TFA/$CH_2Cl_2$) to afford cinnamic ester C8.

In Scheme I(I) cinnamic ester C9 can be prepared from amine B29 as described below.

Amine B29 is protected with allyl bromide ($K_2CO_3$, EtOH, 60° C.) followed by formylation under standard conditions ($POCl_3$, DMF). The resulting aldehyde is condensed with $(EtO)_2P(O)CH_2CO_2Et$ (NaH, THF, 0° to room temperature). The allyl protected cinnamic ester derivative can be deprotected ($Pd(PPh_3)_4$, N,N'-dimethyl-barbituric acid, $CH_2Cl_2$) to afford cinnamic ester C9.

Specifically, in Scheme II:

In the synthesis of intermediate benzoic acids (A1) through (A17), the starting amino benzoic acids

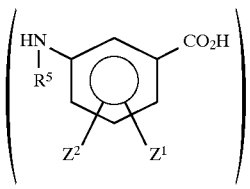

are either commercially available or can be converted to such amino benzoic acids via reduction of the corresponding nitro benzoic acid, which can be obtained commercially or synthesized by nitration of the appropriate benzoic acid, followed by reduction to the desired amino benzoic acid. These are all when $R^5$ is H. If $R^5$ is other than H, alkylation of the amino functionality can be achieved by conventional methodology.

Furthermore, synthesis of intermediate (A2) can also be accomplished as disclosed generally in U.S. Pat. No. 3,202,660, starting with the appropriate amino benzoic acid. Furthermore, intermediate (A2) and (A15) as well as further analogues of (A2) and (A15) such as substitutions on the heterocyclic ring, oxazolidines, thiazolidines, benzimidazoles and the like can also be accomplished as disclosed in 1) Chem. Pharm. Bull. 41(1) 117–125 (1993)
2) Chem. Pharm. Bull. 33(10) 4409–4421 (1985)
3) J. Med. Chem. 18 (1), 90–99 (1975).

All other reagents in Scheme II are either commercially available or readily synthesized by methodologies known by those skilled in the art.

In Scheme III(A) intermediate A1 or A16 can be coupled with cinnamic esters (C1, C2,C3 or C8) using standard methodologies known by those skilled in the art. Hydrolysis (NaOH, MeOH, $H_2O$) of the resulting cinnamic ester (D1, D3,D5 or D7) leads to the desired cinnamic acid analogs (D2,D4,D6 or D8).

In Scheme III(B) intermediate C2 or C3 can be coupled with 3-nitrobenzoyl chloride ($Et_3N$, $CH_2Cl_2$, 0° C. to room temperature). Reduction of the resulting nitrocinnamic ester derivative D9 ($SnCl_2$, EtOH, 75° C.) followed by a two step protocol [1] BOCNHCSNHBOC, $HgCl_2$, $Et_3N$, DMF; 2) TFA] affords the guanidinocinnamic ester analog D10. Hydrolysis (NaOH, MeOH, $H_2O$) gives the guanidinocinnamic acid D11.

In Scheme III(C) an analogous procedure can be used to prepare cyclic guanidine D12 or D13. Treatment of the aminocinnamic ester analog with either N,N'-bis-(t-butoxycarbonyl)-2-imidazolidinethione ($HgCl_2$, $Et_3N$, DMF, 60° C.) or N,N'-bis-(t-butoxycarbonyl)-2-(1H)-tetrahydropyrimidinethione ($HgCl_2$, $Et_3N$, DMF, 60° C.) followed by deprotection (TFA) and hydrolysis (NaOH, MeOH, $H_2O$) yields the cyclic guanidine D12 or D13.

In Scheme III(D) methyl 3-hydroxycinnamate is condensed with 2-bromo-3'-nitroacetophenone ($K_2CO_3$, acetone, heat). The resulting phenacyl ether D14 can be converted to cinnamic acid D16 using methodology described in Scheme III(B).

In Scheme III(E) 3-nitrophenol is reacted with 2- bromo-3'-bromoacetophenone ($K_2CO_3$, acetone, heat) to give the phenacyl ether D17. Reduction ($H_2$, 3% Pt/C, EtOAc) to yield D18 followed by a standard Heck coupling procedure with ethyl acrylate ($Pd(OAc)_2$, $P(O\text{-tolyl})_3$, $Et_3N$, 100° C.) afford D19. The resulting cinnamic ester D19 can be converted to cinnamic acid D20 using methodology described in Scheme III(C).

In Scheme III(F) cyclopropane D21 is prepared from 3-nitrostyrene and m-CPBA. Addition of t-butyl 3-aminocinnamate (COCl$_2$, MeCN, heat) gives the cinnamic ester derivative D22. The resulting cinnamic ester D22 can be converted to cinnamic acid D23 using methodology described in Scheme III(B).

In Scheme III(G) aldol condensation of 3-bromobenzaldehyde and 3-nitroacetophenone (KOH, EtOH) provides unsaturated ketone D24. Heck coupling with t-butyl acrylate (Pd(OAc)$_2$, P(O-tolyl)$_3$, Et$_3$N, 100° C.) affords the cinnamic ester D25. The resulting cinnamic ester D25 can be converted to cinnamic acid D26 using methodology described in Scheme III(B). Alternatively, unsaturated ketone D24 can be reduced (H$_2$, PtO, 60 psi) to give saturated ketone D27. In the same manner as previously described saturated ketone D27 can be converted to cinnamic acid D29.

In Scheme III(H) aldol condensation of 3-nitrobenzaldehyde and 3-bromoacetophenone (KOH, EtOH) yields unsaturated ketone D30. In an analogous method with Scheme III(G), unsaturated ketone D30 is converted to cinnamic acids D32 and D35.

In Scheme III(I) 3-nitrostyrene and ethyl 3-bromocinnamate are coupled using a standard Heck procedure (Pd(OAc)$_2$, P(O-tolyl)$_3$, Et$_3$N, 90° C.) The resulting alkene D36 can be converted to cinnamic acid D38 using methodology described in Scheme III(B).

In Scheme III(J) 3-nitrobenzyl bromide is alkylated with ethyl 4-hydroxycinnamate (K$_2$CO$_3$, DMF). The resulting benzyl ether D39 can be converted to cinnamic acid D40 using methodology described in Scheme III(C).

In Scheme III(K) 3-nitrobenzamide is condensed with 3-bromophenacyl bromide at 140° C. The resulting oxazole D41 is coupled with t-butyl acrylate using a standard Heck procedure (Pd(OAc)$_2$, P(O-tolyl)$_3$,Et$_3$N, 100° C.) The resulting cinnamic ester can be converted to cinnamic acid D42 using methodology described in Scheme III(B).

In Scheme III(L) 4-bromobenzamide is condensed with 3-nitrophenacyl bromide at 140° C. The resulting oxazole D43 can be converted to cinnamic acid D44 using methodology described in Scheme III(K).

In Scheme III(M) 3-nitrobenzamidine is condensed with 4-bromophenacyl bromide (CHCl$_3$,heat). The resulting imidazole D45 can be converted to cinnamic acid D46 using methodology described in Scheme III(K).

EXAMPLE A

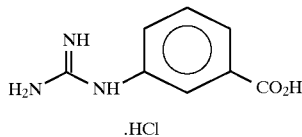

.HCl

A solution of 3-aminobenzoic acid (40.47 g, 0.29 mol), 3,5-dimethylpyrazole carboxamidine nitrate (88.24 g, 0.44 mol), and diisopropylethylamine (76 mL, 0.44 mol) in dioxane(300 mL)/water (150 mL) was heated to reflux for 1 hour, 15 minutes. A brown precipitate resulted. The reaction was stirred at room temperature for over 48 hours. The reaction mixture was filtered and the resulting lavender solid rinsed with dioxane (150 mL) followed by 1:1 dioxane/water (100 mL). The solid was dried in vacuo and then treated with a mixture of ether(400 mL)/acetonitrile(100 mL)/4N HCl/Dioxane (100 mL). To this slurry was added 20% HCl (1 mL). The mixture was stirred at room temperature over 18 hours. The undissolved solid was filtered off and washed with ether (2×). The desired product was collected as a pale purple solid (28.15 g, 45% yield). NMR was consistent with the proposed structure.

EXAMPLE B 3-guanidino-5-trifluoromethylbenzoic acid, hydrochloride

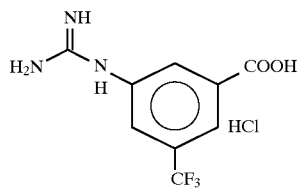

The title compound was synthesized according to the methodology of Example A, substituting an equivalent amount of 3-amino-5-trifluoromethylbenzoic acid for 3-aminobenzoic acid.

EXAMPLE C

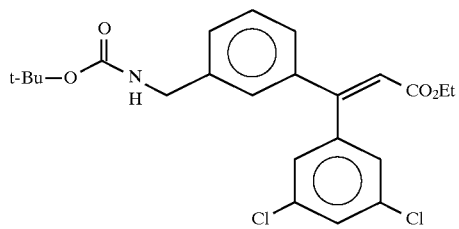

Step A

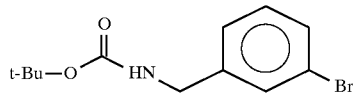

A solution of 3-bromobenzylamine hydrochloride (2.93 g, 13 mmol), di-tert-butyldicarbonate (2.874 g, 13 mmol), and triethylamine (3.7 mL, 26 mmol) in 80:20 dioxane/water (40 mL) was stirred at room temperature for 23 hours. The reaction was concentrated in vacuo and the residue dissolved in EtOAc. The solution was washed with water and brine. Concentration in vacuo gave a light yellow solid (4.59 g). NMR was consistent with proposed structure.

Step B

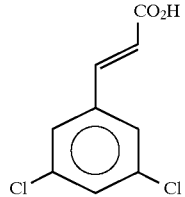

A mixture of 3,5-dichlorobenzaldehyde (2.00 g, 11.4 mmol), malonic acid (1.451 g, 12.6 mmol), and pyridine (0.16 mL, 1.9 mmol) in absolute ethanol (20 mL) was heated to 105° C. (bath) under argon. After 24 hours the reaction was allowed to cool to room temperature and then concentrated in vacuo to give a white solid slurry. The solid was redissolved in Et₂O (50 mL) and washed with 1M HCl followed by water. The organic layer was collected, dried over MgSO₄, and concentrated in vacuo to give a white sticky solid. The solid was purified by slurrying with hexane. The undissolved white solid was collected by vacuum filtration (0.65 g). NMR was consistent with proposed structure.

Step C

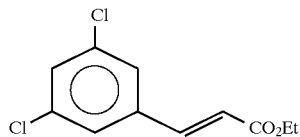

A solution of the compound of Step B (0.65 g, 3.0 mmol) in absolute EtOH (60 mL) was cooled to 0° C. and HCl (g) was bubbled in for 15 minutes. The solution was allowed to stir at room temperature for 5 hours. An aliquot was removed and concentrated in vacuo. H NMR showed the reaction to be complete. The reaction was concentrated in vacuo to give a white solid (0.74 g). NMR was consistent with proposed structure.

Step D

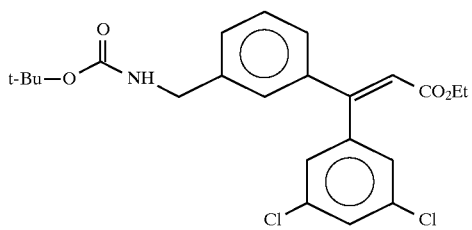

A solution of Step A (0.44 g, 1.5 mmol) and the compound of Step C (0.36 g, 1.5 mmol) in diisopropylamine (4 mL) was purged for 5 minutes with argon before adding tri-o-tolylphosphine (0.024 g, 0.05 mmol) and palladium acetate (0.010 g, 0.03 mmol). The resulting solution was purged with argon for 3 minutes and sealed. The reaction vessel was heated to 135°–140° C. (bath) for 5 hours. The reaction was diluted with water (50 mL) and extracted with EtOAc (50 mL). The organic layer was collected and washed a second time with water. The organic layer was dried over MgSO₄ and filtered through celite. Concentration in vacuo gave the crude product as a yellow solid (0.69 g). The solid was purified by column chromatography [100 g silica gel, 20% EtOAc/hexane (500 mL)] to give a white solid (0.31 g). NMR was consistent with the proposed structure.

EXAMPLE 1

Synthesis of methyl 3-[3-[[[[3-[(aminoiminomethyl)-amino]phenyl]carbonyl]amino]methyl]phenyl]-2-propenoate, trifluoroacetate salt

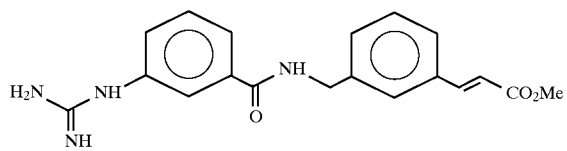

Step A

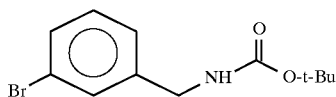

A solution of 3-bromobenzylamine hydrochloride (2.93 g, 13 mmol), di-tert-butyldicarbonate (2,874 g, 13 mmol), and triethylamine (3.7 mL, 26 mmol) in 80:20 dioxane/water (40 mL) was stirred at room temperature for 23 hours. The reaction was concentrated in vacuo and the residue dissolved in EtOAc. The solution was washed with water and brine. Concentration in vacuo gave a light yellow solid (4.59 g, quantitative yield). NMR was consistent with the proposed structure.

Step B

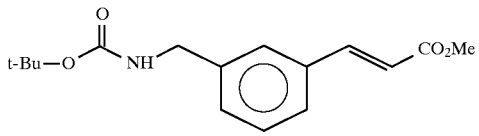

A solution of compound of Step A (1.949 g, 7.2 mmol) and methyl acrylate (2 mL, 27.2 mmol) in diisopropylamine (15 mL) was purged for 2 minutes with argon before adding tri-o-tolylphosphine (0.095 g, 0.29 mmol) and palladium acetate (0.043 g, 0.14 mmol). The resulting orange solution was purged with argon for 2 minutes and sealed. The reaction was then allowed to stir at room temperature over 16 hours. The reaction was diluted with water (50 mL) and extracted with EtOAc (50 mL). The organic layer was collected and washed a second time with water. The organic layer was dried over MgSO₄ and filtered through celite. Concentration in vacuo gave the crude product as a yellow oil (2.52 g). The oil was purified by column chromatography [100 g silica gel, 20% EtOAc/hexane (700 mL)]. The yellow oil collected was then dissolved in EtOAc and washed with 1N HCl to remove the side product formed from diisopropylamine reacting with the methyl acrylate. The organic layer was dried over MgSO₄ and concentrated in vacuo to give a yellow solid (1.473 g, 68% yield). NMR was consistent with the proposed structure.

Step C

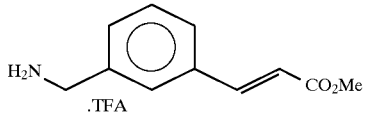

To a solution of the compound of Step B (1.437 g, 4.9 mmol) in CH₂Cl₂ (15 mL) was added trifluoroacetic acid (5 mL) at 0° C. The reaction was allowed to warm to room temperature and stirred for 2 hours. The reaction was concentrated in vacuo to give a yellow/orange oil (2.234 g, quantitative yield). NMR was consistent with the proposed structure.

Step D

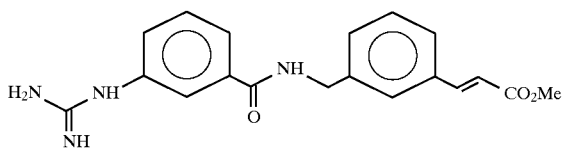

A solution of the compound of Example A (0.709 g, 3.3 mmol) and 1-methyl piperidine (0.40 mL, 3.3 mmol) in DMF (8 mL) was cooled to 0° C. and isobutyl chloroformate (0.42 mL, 3.3 mmol) was added under argon. The reaction was allowed to stir for 5 minutes before adding a mixture of the product of Step C (1.042 g, 3.3 mmol) and 1-methylpiperidine (0.40 mL, 3.3 mmol) in DMF (5 ML). The flask containing the product of Step C was rinsed with DMF (5 mL) and the rinse added to the reaction. The ice bath was removed after addition and the reaction was allowed to stir at room temperature over 24 hours. The reaction was concentrated in vacuo and the crude material purified by HPLC to give the desired product as a yellow oil (0.565 g).

Analysis Calculated for $C_{19}H_{20}N_4O_3$. 1.3 TFA+0.5 $H_2O$: C, 50.91; H, 4.41; N, 10.99. Found: C, 50.74; H, 4.10; N, 11.16. MH+=353.

EXAMPLE 2

Synthesis of 3-[3-[[[[3-[(aminoiminomethyl)amino] phenyl]carbonyl]amino]methyl]phenyl]-2-propenoic acid, trifluoroacetate salt

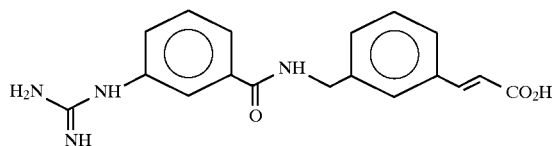

The compound from Example 1 (0.336 g, 0.95 mmol) was dissolved in MeOH (5 mL) and 1M LiOH (1 mL) was added. The reaction was stirred at room temperature over 16 hours. The reaction was concentrated in vacuo to give a white solid. The solid was dissolved in a small amount of $H_2O$ and acidified with 1 drop of TFA. The mixture was concentrated in vacuo and the residue was purified by HPLC to give the desired product (0.277 g).

Analysis Calculated for $C_{18}H_{18}N_4O_3$. 1.3 TFA+0.4 $H_2O$: C, 50.11; H, 4.10; N, 11.35. Found: C, 49.83; H, 3.86; N, 11.56. MH+=339.

EXAMPLE 3

Synthesis of ethyl 3-[4-[[[3-[(aminoiminomethyl) amino] phenyl]carbonyl]amino]phenyl]-2-propenoate, monohydrate trifluoroacetate salt

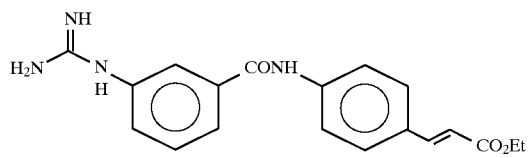

To a stirred solution of the compound of Example A (500 mg, 2.3 mmol) in dimethyl formamide (10 mL) at 0° C. was added 1-methylpiperidine (228 mg, 2.3 mmol) followed by the addition of isobutyl chloroformate (314 mg, 2.3 mmol). After 5 minutes ethyl 4-aminocinnamate hydrochloric acid (522 mg, 2.3 mmol) in dimethyl formamide (1 mL) was introduced. The reaction mixture was warmed to room temperature and stirred overnight. The solvent was removed under reduced pressure, and the residue was purified by reverse phase HPLC-Method 1 to give 600 mg yellow solid.

Analysis Calculated for $C_{19}H_{20}N_4O_3$. 1.2 TFA.1 $H_2O$: C, 50.67; H, 4.61; N, 11.05. Found: C, 50.40; H, 4.31; N, 11.19.

EXAMPLE 4

Synthesis of 3-[4-[[[3-[(aminoiminomethyl)amino] phenyl] carbonyl]amino]phenyl]-2-propenoic acid, trifluoroacetate salt

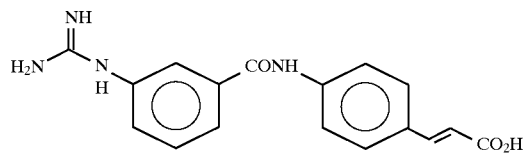

The compound of Example 3 (185 mg, 0.52 mmol) was dissolved in methanol (3 mL) at room temperature. Lithium hydroxide (3 mL) was added and the reaction mixture was stirred overnight. The solution was concentrated and purified by reverse phase HPLC-Method 1 to give 70 mg of the title compound.

Analysis Calculated for $C_{17}H_{16}N_4O_3$. 1.4 TFA 0.9 $H_2O$: C, 47.55; H, 3.87; N, 11.20. Found: C, 47.67; H, 3.53; N, 11.14.

EXAMPLE 5

3-[4-[[[3-[(arainoiminomethyl)amino]phenyl] carbonyl]amino]-3-methylphenyl]propenoic acid, trifluoroacetate salt

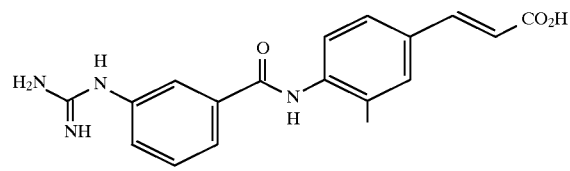

Step A

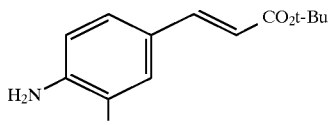

In a pressure tube was added 4-bromo-2-methylaniline (1.86 g, 10.0 mmol), palladium acetate (22 mg, 0.1 mmol), tri-O-tolylphosphine (243 mg, 0.8 mmol), t-butyl acrylate (1.8 mL, 12.5 mmol) and triethylamine (5.0 mL, 35.9 mmol). The tube was purged with nitrogen and sealed. The reaction mixture was heated at 100° C. for 3 hours. The reaction mixture was cooled and partitioned between water and ether. The organic solution was washed with water, dried and concentrated in vacuo. The residue was purified by chromatography on silica (2:1 hexane:ethyl acetate) to give the desired compound (2.1 g). $^1$H NMR was consistent with the proposed structure.

Step B

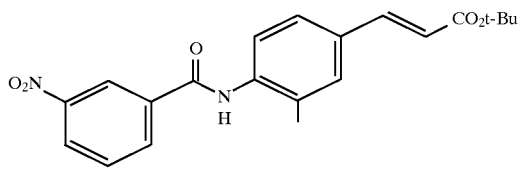

To a solution of the compound from Step A (1.0 g, 4.3 mmol) in $CH_2Cl_2$ (15 mL) at 0° C. was added 3-nitrobenzoyl chloride (835 mg, 4.5 mmol) and triethylamine (0.62 mL, 4.5 mmol). The reaction solution was kept at 0° C. for 1 hour and then warmed to room temperature over 2 hours. The reaction mixture was concentrated in vacuo and the residue partitioned between ethyl acetate and water. The organic solution was washed with water, brine, dried, and concentrated. The residue was purified by chromatography on silica (3:1 hexane:ethyl acetate) to yield the above compound (1.6 g). $^1H$ NMR was consistent with the proposed structure.

Step C

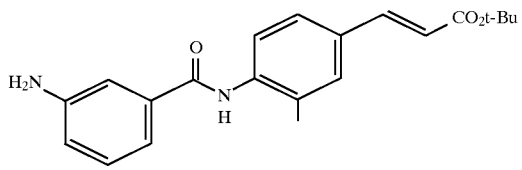

To a mixture of the compound from Step B (1.6 g, 4.2 mmol) in ethanol (40 mL) was added tin (II) chloride dihydrate (3.9 g, 16.8 mmol). The reaction mixture was heated at 75° C. for 3 hours. The reaction solution was cooled and partioned between ether and water. The organic solution was washed with water, dried and concentrated. The residue was purified by chromatography on silica (1:1 hexane:ethyl acetate) to yield the above compound (1.2 g). $^1H$ NMR was consistent with the proposed structure.

Step D

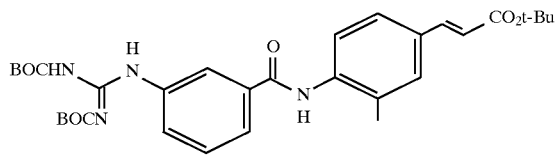

To a solution of the compound from Step C (300 mg, 0.8 mmol) in DMF (2 mL) was added N,N'-bisbocthiourea (327 mg, 0.8 mmol) and mercuric choride (280 mg, 1.0 mmol). The mixture was stirred at room temperature for 1.5 hours. The mixture was filtered through a pad of Celite and the filter pad washed repeatedly with ethyl acetate. The organic solution was dried and concentrated. The residue was purified by chromatography on silica (3:1 hexane:ethyl acetate) to yield the above compound (225 mg). $^1H$ NMR was consistent with the proposed structure.

Step E

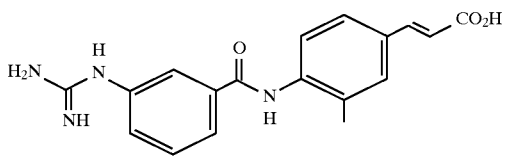

A solution of the compound from Step D (225 mg) in a 1:1 $CH_2Cl_2$:TFA (5 mL) solution was kept at room temperature for 2 hours. The solution was concentrated under a stream of nitrogen. The residue was purified by reverse phase HPLC (water/TFA:acetonitrile) to afford the above compound (76 mg).

Anal. calcd for $C_{18}H_{18}N_4O_3$+1.4 TFA: C, 50.17; H, 3.93; N, 11.24. Found: C, 50.29; H, 3.85; N, 11.23.

EXAMPLE 6 ethyl 3-[4-[[[3-[(aminoiminomethyl)amino]phenyl]-carbonyl]amino]-3-methylphenyl]-2E-propenoate, trifluoroacetate salt

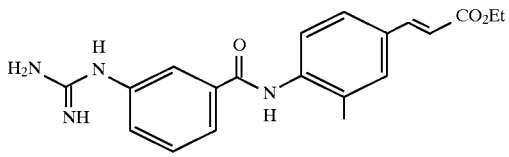

The above compound was prepared as in Example 5, Steps A–E, starting with 4-bromo-2-methylaniline and ethyl acrylate.

Anal. calcd for $C_{20}H_{22}N_4O_3$+1.5 TFA: C, 51.40; H, 4.41; N, 10.42. Found: C, 51.11; H, 4.35; N, 10.51.

EXAMPLE 7

3-[4-[[[3-[(aminoiminomethyl)amino]phenyl]carbonyl]amino]-3-ethylphenyl]propenoic acid, trifluoroacetate salt

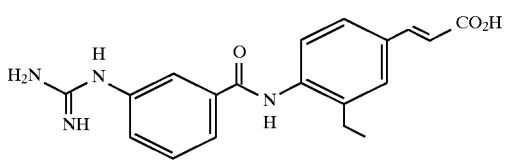

The above compound was prepared as in Example 5, Steps A–E, starting with 4-bromo-2-ethylaniline.

Anal. calcd for $C_{19}H_{20}N_4O_3$+1.4 TFA: C, 51.14; H, 4.21; N, 10.94. Found: C, 51.36; H, 4.02; N, 11.27.

EXAMPLE 8 ethyl 3-[4-[[[3-[(aminoiminomethyl)amino]phenyl]carbonyl]-amino]-3-ethylphenyl]propenoate, trifluoroacetate salt

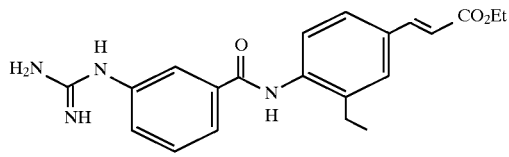

The above compound was prepared as in Example 5, Steps A–E, starting with 4-bromo-2-ethylaniline and ethyl acrylate.

Anal. calcd for $C_{21}H_{24}N_4O_3$+1.2 TFA: C, 54.34; H, 4.91; N, 10.83. Found: C, 54.17; H, 4.93; N, 10.83.

EXAMPLE 9

3-[4-[[[3-[(aminoiminomethyl)amino]phenyl]-carbonyl]amino]3-chlorophenyl]propenoic acid, trifluoroacetate salt

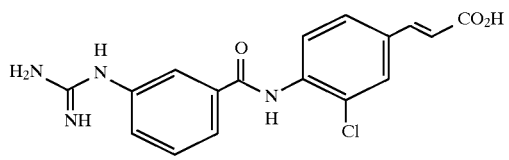

The above compound was prepared as in Example 5, Steps A–E, starting with 4-bromo-2-chloroaniline.

Anal. calcd for $C_{17}H_{15}N_4O_3Cl$+1.7 TFA+0.4 $H_2O$: C, 43.77; H, 3.15; N, 10.03. Found: C, 43.62; H, 2.92; N, 10.36.

EXAMPLE 10 ethyl 3-[4-[[[3-[(aminoiminomethyl)amino]phenyl]-carbonyl]amino]-3-chlorophenyl]-2E-propenoate, trifluoroacetate salt

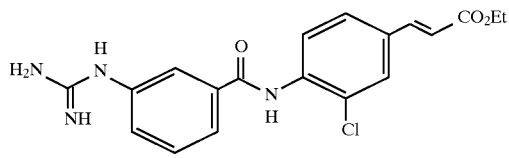

The above compound was prepared as in Example 5, Steps A–E, starting with 4-bromo-2-chloroaniline and ethyl acrylate.

Anal. calcd for $C_{19}H_{19}N_4O_3Cl$+1.1 TFA: C, 49.71; H, 3.95; N, 10.94. Found: C, 49.63; H, 3.70; N, 10.89.

EXAMPLE 11

3-[4-[[[3-[(aminoiminomethyl)aminol]phenyl]carbonyl]-amino]-3-fluorophenyl]-2E-propenoic acid, trifluoroacetate salt

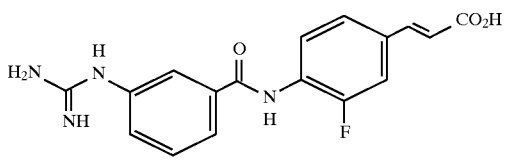

The above compound was prepared as in Example 5, Steps A–E, starting with 4-bromo-2-fluoroaniline.

Anal. calcd for $C_{19}H_{19}N_4O_3F$+1.05 TFA: C, 49.65; H, 3.50; N, 12.13. Found: C, 49.46; H, 3.52; N, 12.14.

EXAMPLE 12

3-[4-[[[3-[(aminoiminomethyl)amino]phenyl]carbonyl]amino]-3-(trifluoromethyl)phenyl]-2E-propenoic acid, trifluoroacetate salt

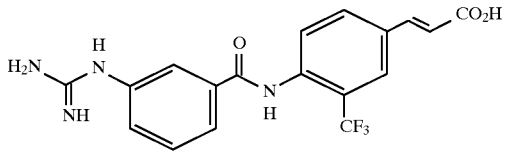

The above compound was prepared as in Example 5, Steps A–E, starting with 4-bromo-2-trifluoromethylaniline.

Anal. calcd for $C_{18}H_{15}N_4O_3F_3$+1.4 TFA: C, 45.26; H, 2.99; N, 10.15. Found: C, 45.12; H, 3.01; N, 10.38.

EXAMPLE 13

3-[4-[[[3-[(aminoiminomethyl)amino]phenyl]carbonyl]-amino]-3,5-dimethylphenyl]-2E-propenoic acid, trifluoroacetate salt

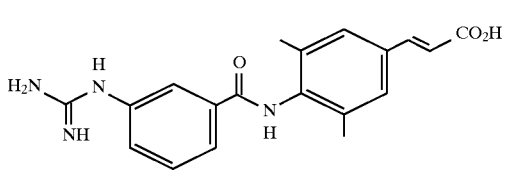

The above compound was prepared as in Example 5, Steps A–E, starting with 4-bromo-2,6-dimethylaniline.

Anal. calcd for $C_{19}H_{20}N_4O_3$+1.2 TFA: C, 52.76; H, 4.39; N, 11.53. Found: C, 52.79; H, 4.15; N, 11.60.

EXAMPLE 14 ethyl 3-[4-[[[3-[(aminoiminomethyl)amino]phenyl]-carbonyl]amino]-3,5-dimethylphenyl]-2E-propenoate, trifluoroacetate salt

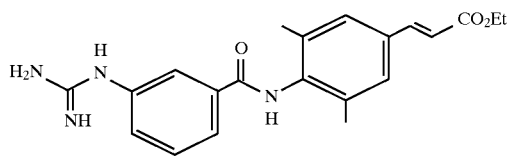

The above compound was prepared as in Example 5, Steps A–E, starting with 4-bromo-2,6-dimethylaniline and ethyl acrylate.

Anal. calcd for $C_{21}H_{24}N_4O_3$+1.35 TFA: C, 53.27; H, 4.78; N, 10.48. Found: C, 53.18; H, 4.77; N, 10.37.

EXAMPLE 15

3-[4-[[[3-[(aminoiminomethyl)amino]phenyl]carbonyl]-amino]-3-chloro-5-methylphenyl]-2E-propenoic acid, trifluoroacetate salt

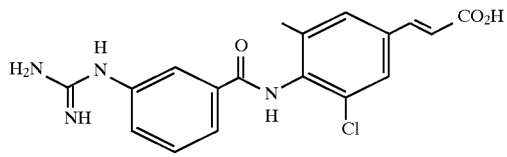

The above compound was prepared as in Example 5, Steps A–E, starting with 4-bromo-2-chloro-6-methylaniline.

Anal. calcd for $C_{18}H_{17}N_4O_3Cl$+1.5 TFA: C, 46.38; H, 3.43; N, 10.30. Found: C, 45.97; H, 3.47; N, 10.65.

EXAMPLE 16

3-[4-[[[3-[(aminoiminomethyl)amino]phenyl]carbonyl]-amino]naphthalen-1-yl]-2E-propenoic acid, trifluoroacetate salt

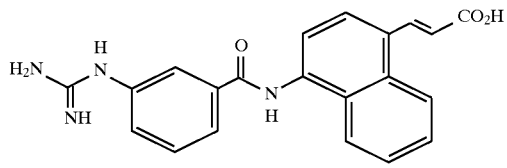

The above compound was prepared as in Example 5, Steps A–E, starting with 1-amino-4-bromonapthalene.

Anal. calcd for $C_{21}H_{18}N_4O_3$+1.45 TFA: C, 53.19; H, 3.65; N, 10.38. Found: C, 52.91; H, 3.99; N, 10.75.

EXAMPLE 17

3-[4-[[[3-[(aminoiminomethyl)amino]phenyl]carbonyl]-amino]-3-methoxyphenyl]propenoic acid, trifluoroacetate salt

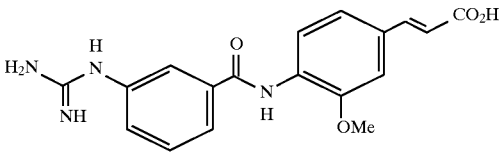

Step A

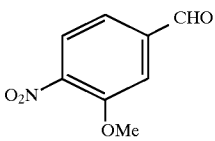

To a solution of 3-methoxy-4-nitrobenzyl alcohol (2.0 g, 10.9 mmol) in $CH_2Cl_2$ (20 mL) was added 4° molecular sieves (5 g) and N-methylmorpholine N-oxide (1.9 g, 16.4 mmol). To the stirred mixture was added tetrapropylammonium perruthenate [TPAP] (192 mg, 0.5 mmol). The mixture was stirred at room temperature for 1 hour and filtered through a pad of silica gel. The filtrate was concentrated and the residue purified by chromatography on silica (3:1 hexane:ethyl acetate) to yield the above compound (970 mg). $^1H$ NMR was consistent with the proposed structure.

Step B

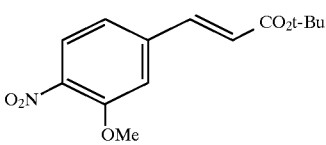

To a solution of t-butyl P,P-dimethylphosphonoacetate (1.0 mL, 5.77 mmol) in THF (10 mL) was added sodium hydride (230 mg of a 60% dispersion in mineral oil). The mixture was stirred at room temperature for 1 hour and then added via canula to a solution of the product of Step A (950 mg, 5.25 mmol) in THF (5 mL). The reaction solution was kept at room temperature for 18 hours. The mixture was partitioned between water and ethyl acetate. The aqueous solution was extracted with ethyl acetate. The combined organic solution was dried and concentrated. The residue was purified by chromatography on silica (3:1 hexane:ethyl acetate) to yield the above compound (910 mg). $^1H$ NMR was consistent with the proposed structure.

Step C

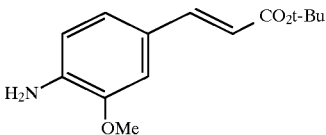

The above compound was prepared as in Example 5, Step C, starting from the product of Step B. $^1H$ NMR was consistent with the proposed structure.

Step D

The above compound was prepared as in Example 5, Step B, starting from the product of Step C. ¹H NMR was consistent with the proposed structure.

Step E

The above compound was prepared as in Example 5, Step C, starting from the product of Step D. ¹H NMR was consistent with the proposed structure.

Step F

The above compound was prepared as in Example 5, Step D, starting from the product of Step E. ¹H NMR was consistent with the proposed structure.

Step G

The above compound was prepared as in Example 5, Step E, starting from the product of Step F.

Anal. calcd for $C_{11}H_{15}N_4O_3Cl+1.3$ TFA: C, 49.23; H, 3.80; N, 11.14. Found: C, 48.61; H, 3.72; N, 11.34.

EXAMPLE 18

3-[3-methyl-4-[[[3-[(1,4,5,6-tetrahydropyrimidin-2-yl)amino]phenyl]carbonyl]amino]phenyl]propenoic acid, trifluoroacetate salt Step A To a solution of the product from Example 5, Step C (335 mg, 0.95 mmol) in DMF (3 mL) was added N,N'-bis-(t-butoxycarbonyl)-2-(1 H)-tetrahydropyrimidinethione (315 mg, 1.0 mmol), triethylamine (0.4 mL, 2.9 mmol) and mercuric chloride (320 mg, 1.2 mmol). The mixture was heated at 65° C. for 19 hours. The mixture was cooled, diluted with ethyl acetate and filtered through Celite. The Celite pad was washed with ethyl acetate and the organic solution was concentrated. The residue was purified by chromatography on silica (2:1 hexane:ethyl acetate) to give the above compound (310 mg). ¹H NMR was consistent with the proposed structure.

Step B

The above compound was prepared as in Example 5, Step E starting from the product of Example 18, Step A.

Anal. calcd for $C_{21}H_{22}N_4O_3+1.6$ TFA: C, 51.83; H, 4.24; N, 9.99. Found: C, 51.81; H, 4.54; N, 10.09.

EXAMPLE 19

3-[3-ethyl-4-[[[3-[(1,4,5,6-tetrahydropyrimidin-2-yl)amino]phenyl]carbonyl]amino]phenyl]propenoic acid, trifluoroacetate salt The above compound was prepared as in Example 18, Steps A–B, starting from the product of Example 7, Step C.

Anal. calcd for $C_{22}H_{24}N_4O_3+1.1$ TFA: C, 56.12; H, 4.88; N, 10.81. Found: C, 56.41; H, 4.77; N, 10.96.

EXAMPLE 20 ethyl 3-[3-ethyl-4-[[[3-[(1,4,5,6-tetrahydropyrimidin-2-yl)amino]phenyl]carbonyl]amino]phenyl]propenoate, trifluoroacetate salt

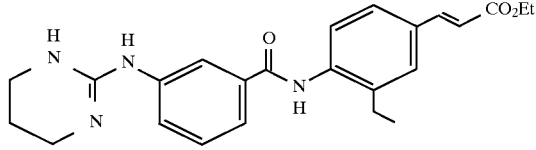

The above compound was prepared as in Example 18, Steps A–B, starting from the product of Example 8, Step C.

Anal. calcd for $C_{24}H_{28}N_4O_3$+1.2 TFA: C, 56.89; H, 5.28; N, 10.04. Found: C, 57.04; H, 5.41; N, 10.39.

EXAMPLE 21

3-[4-[[[3-[(4,5-dihydro-1H-imidazol-2-yl) amino]-phenyl]carbonyl]amino]-3-ethylphenyl]propenoic acid, trifluoroacetate salt

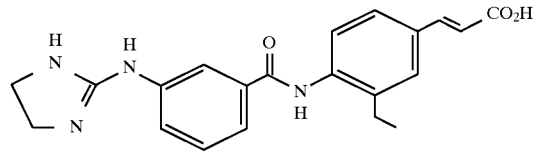

Step A

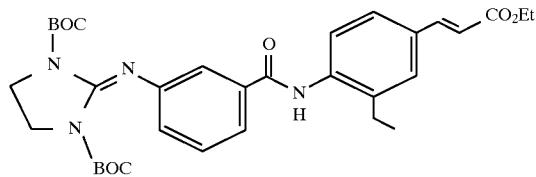

To a solution of the product from Example 8, Step C (400 mg, 1.1 mmol) in DMF (3.5 mL) was added N,N'-bis-(t-butoxycarbonyl)-2-imidazolidinethione (404 mg, 1.3 mmol), triethylamine (0.46 mL, 3.2 mmol) and mercuric chloride (370 mg, 1.36 mmol). The mixture was heated at 65° C. for 18 hours. The mixture was cooled, diluted with ethyl acetate and filtered through Celite. The Celite pad was washed with ethyl acetate and the organic solution was concentrated in vacuo. The residue was purified by chromatography on silica (2:1 hexane:ethyl acetate) to give the desired compound (525 mg). $^1$H NMR was consistent with the proposed structure.

Step B

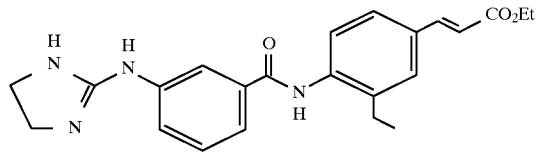

The above compound was prepared as in Example 5, Step E starting from the product of Example 21, Step A. $^1$H NMR was consistent with the proposed structure.

Step C

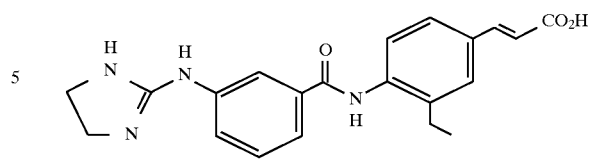

To a solution of the product from Example 21, Step B (95 mg, 0.24 mmol) in methanol (2 mL) and THF (2 mL) was added sodium hydroxide (100 mg, 2.5 mmol). The reaction solution was kept at room temperature for 18 hours. The solution was concentrated and purified by reverse phase HPLC (water/TFA:acetonitrile) to give the desired compound (49 mg). Anal. calcd for $C_{21}H_{22}N_4O_3$+1.1 TFA: C, 55.30; H, 4.62; N, 11.12. Found: C, 54.99; H, 4.48; N, 10.86.

EXAMPLE 22

3-[3-chloro-4-[[[3-[(1,4,5,6-tetrahydropyrimidin-2-yl)amino]phenyl]carbonyl]amino]phenyl]propenoic acid, trifluoroacetate salt

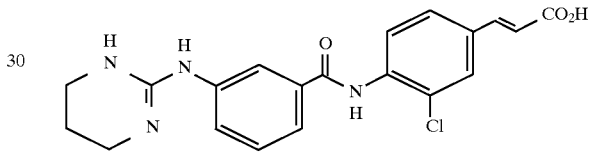

The above compound was prepared as in Example 18, Steps A–B, starting from the product of Example 9, Step C.

Anal. calcd for $C_{20}H_{19}N_4O_3Cl$+1.0 TFA: C, 51.52; H, 3.93; N, 10.92. Found: C, 51.26; H, 3.77; N, 10.72.

EXAMPLE 23

3-[3-chloro-4-[[[3-[(4,5-dihydro-1H-imidazol-2-yl)amino]-phenyl]carbonyl]amino]phenyl]-2E-propenoic acid, trifluoroacetate salt

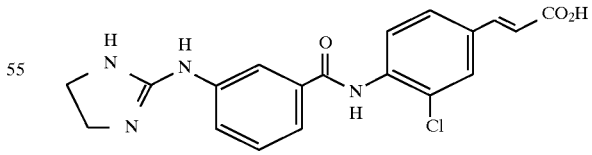

The above compound was prepared as in Example 21, Steps A–C, starting from the product of Example 10, Step C.

Anal. calcd for $C_{19}H_{17}N_4O_3Cl$+1.1 TFA: C, 49.90; H, 3.58; N, 10.98. Found: C, 49.92; H, 3.35; N, 10.97.

EXAMPLE 24

3-[3,5-dimethyl-4-[[[3-[(1,4,5,6-tetrahydropyrimidin-2-yl)amino]phenyl]carbonyl]amino]phenyl]-2E-propenoic acid, bis (trifluoroacetate salt)

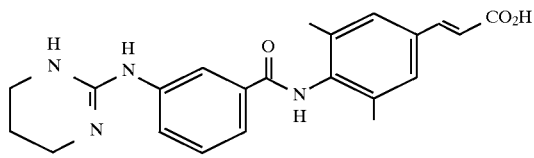

The above compound was prepared as in Example 18, Steps A–B, starting from the product of Example 13, Step C. Anal. calcd for $C_{22}H_{24}N_4O_3$+2.1 TFA: C, 49.80; H, 4.16; N, 8.87. Found: C, 50.20; H, 4.03; N, 8.61.

EXAMPLE 25

3-[4-[[[3-[(4,5-dihydroimidazol-2-yl) amino]-phenyl]carbonyl]amino]-3,5-dimethylphenyl]-2E-propenoic acid, trifluoroacetate salt

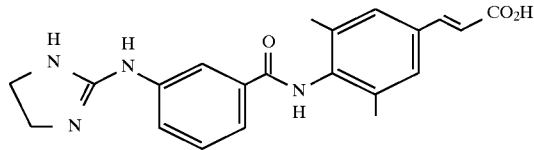

The above compound was prepared as in Example 21, Steps A–B, starting from the product of Example 13, Step C. Anal. calcd for $C_{21}H_{22}N_4O_3$+1.6 TFA: C, 51.82; H, 4.24; N, 9.99. Found: C, 52.13; H, 4.42; N, 9.75.

EXAMPLE 26 ethyl 4-[[[3-[3-[(4,5-dihydroimidazol-2-yl)amino]phenyl]carbonyl]amino]-3,5-dimethylphenyl]propenoate, trifluoroacetate salt

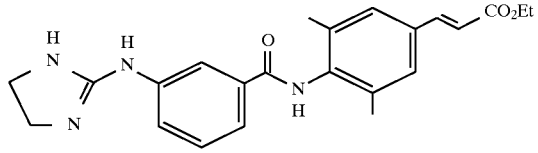

The above compound was prepared as in Example 21, Steps A–B, starting from the product of Example 14, Step C. Anal. calcd for $C_{23}H_{26}N_4O_3$+1.15 TFA: C, 56.52; H, 5.05; N, 10.42. Found: C, 56.52; H, 5.45; N, 10.80.

EXAMPLE 27

3-[4-[[[3-[(aminocarbonyl)amino]phenyl]carbonyl]-amino]-3,5-dimethylphenyl]propenoic acid, trifluoroacetate salt

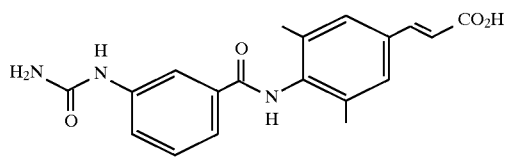

Step A

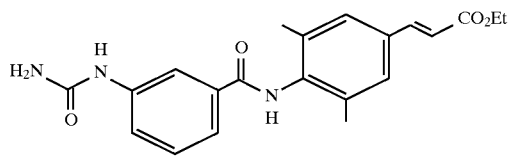

A 1.93M phosgene solution in toluene (0.2 mL) was dissolved in 1 mL methylene chloride and cooled to 0° C. To this solution was added the product from Example 14, Step C (126 mg, 0.37 mmol) and triethylamine (0.1 mL) in methylene chloride (3 mL). After stirring at 0° C. for 0.5 hour the reaction was concentrated and concentrated ammonium hydroxide (5 mL) was added. The reaction was stirred for 45 minutes and a white precipitate formed. The solid was collected and dried to give the desired product. $^1$H NMR was consistent with the proposed structure.

Exact mass calcd for $C_{21}H_{23}N_3O_4(M^+)$: 381.1689. Found: 381.1700.

Step B

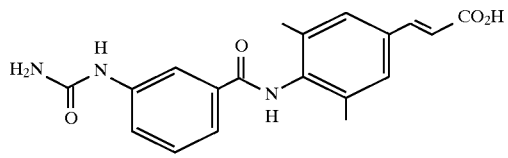

The product from Step A (65 mg, 0.17 mmol) was dissolved in THF (1 mL) and methanol (1 mL). 1N NaOH (1 mL) was added and the reaction was stirred overnight. After concentrating, the residue was acidified with 10% HCl. The resultant white precipitate was collected and dried to afford the desired product. $^1$H NMR was consistent with the proposed structure. Exact mass calcd for $C_{19}H_{19}N_3O_4$ $(M^+)$: 353.1375. Found: 353.1399.

EXAMPLE 28

3-[4-[[[3-[(aminoiminomethyl)amino]phenyl]carbonyl]-amino]-2-chlorophenyl]propenoic acid, trifluoroacetate salt

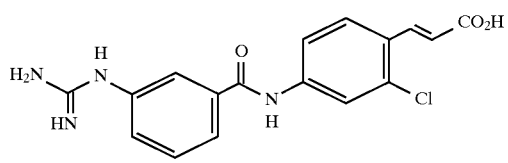

Step A

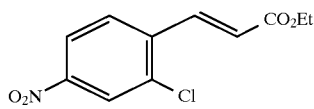

To dimethyl formamide (15 mL) was added 3-chloro-4-iodonitrobenzene (5.0 g, 17.6 mmol), ethyl acrylate (2.5 g, 24.7 mmoles), tetrabutylammonium chloride (4.9 g, 17.6 mmol), sodium bicarbonate (3.7 g, 44.1 mmol) and palladium (II) acetate (158 mg, 0.04 mmol). The slurry was degassed with argon and sealed and heated at 85° C. overnight. The reaction mixture was diluted with water and extracted with methylene chloride. The combined extracts was washed with water, dried ($MgSO_4$) and concentrated in vacuo. The residue was purified by chromatography on silica gel (9:1 hexane:ethyl acetate) to give the desired product (3.9 g). $^1H$ NMR was consistent with the proposed structure.

Step B

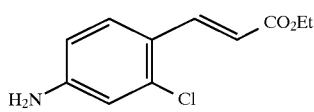

The compound of Step A (3.8 g,14.9 mmol) was dissolved in ethanol (100 mL) and tin (II) chloride dihydrate (10.0 g, 44.6 mmol) was added. The reaction mixture was stirred and refluxed for 1.5 hours. The reaction mixture was cooled, neutralized with 10% aqueous NaOH solution and extracted with ethyl acetate. The extract was dried ($MgSO_4$) and concentrated in vacuo. The residue was purified by chromatography on silica gel (9:1 hexane:ethyl acetate) to provide the desired compound (568 mg). $^1H$ NMR was consistent with the proposed structure.

Step C

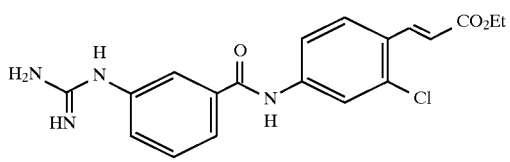

To dimethyl formamide (10 mL) was added the product from Example A (543 mg, 0.25 mmol) and N-methylpiperidine (250 mg, 0.25 mmol). The reaction mixture was cooled to 0° C. and isobutyl chlorofomate (345 mg, 0.25 mmol) was added. After 15 minutes, the compound of Step B (560 mg, 0.25 mmol) was added and the reaction mixture was stirred at room temperature for overnight. The reaction mixture was then concentrated in vacuo and the residue purified by reverse phase HPLC (water/TFA:acetonitrile) to give the desired product (380 mg).

Anal. calcd for $C_{21}H_{20}ClF_3N_4O_5 + 1.0 H_2O$: C, 48.61; H, 4.21; N, 10.80. Found: C, 48.74; H, 3.93; N, 10.80.

Step D

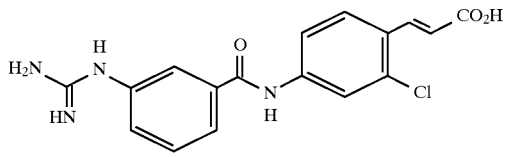

The compound of Step C (310 mg, 0.60 mmol) was dissolved in methanol (2 mL) and 1M aqueous LiOH (2.1 mL, 2.1 mmol) was added. The reaction mixture was stirred at room temperature overnight. The reaction mixture was acidified with trifluoroacetic acid and purified by reverse phase HPLC (water/TFA:acetonitrile) to give the desired product (150 mg).

Anal. calcd for $C_{17}H_{16}Cl_2N_4O_5 + 1.3$ TFA+0.6 $H_2O$: C, 45.46; H, 3.41; N, 10.82. Found: C, 45.49; H, 3.11; N, 10.99.

EXAMPLE 29

3-[4-[[[3-[(aminoiminomethyl)amino]phenyl]carbonyl]-amino]-2,6-dichlorophenyl]propenoic acid, dihydrochloride dihydrate

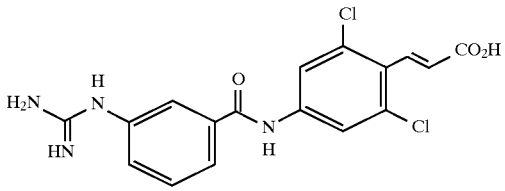

The above compound was prepared as in Example 28, Steps A–D, starting from 3,5-dichloro-4-iodonitrobenzene.

Anal. calcd for $C_{17}H_{14}Cl_2N_4O_3 + 3.0$ HCl+2.0 $H_2O$: C, 37.91; H, 3.93; N, 10.40; Found: C, 37.83; H, 3.55; N, 10.15.

EXAMPLE 30 ethyl 3-[4-[[[3-(aminoiminomethyl)amino]phenyl]-carbonyl]amino]-2-methoxyphenyl]propenoate, trifluoroacetate salt

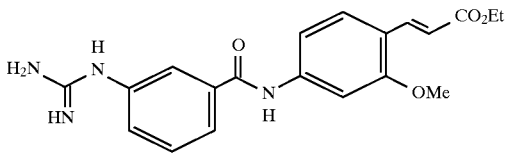

The above compound was prepared as in Example 28, Steps A–C starting from 2-bromo-5-nitroanisole to give the desired product.

Anal. calcd for $C_{20}H_{22}N_4O_4 + 1.1$ TFA+1.0 $H_2O$: C, 50.59; H, 4.82; N, 10.68. Found: C, 50.44; H, 4.46; N, 10.54.

EXAMPLE 31

3-[4-[[[3-(aminoiminomethyl)amino]phenyl]carbonyl]-amino]-2-methoxyphenyl]propenoic acid, trifluoroacetate salt

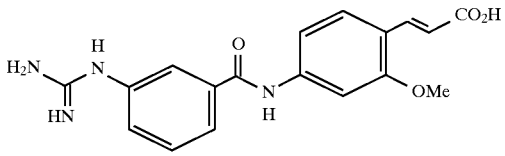

The above compound was prepared as in Example 28, Step D, starting from the product of Example 30 to give the desired product.

Anal. calcd for $C_{18}H_{18}N_4O_4 + 1.2$ TFA+0.8 $H_2O$: C, 48.46; H, 4.15; N, 11.08. Found: C, 48.12; H, 3.90; N, 10.92.

EXAMPLE 32 ethyl 3-[4-[[[3-(aminoiminomethyl)amino]phenyl]
carbonyl]-amino]-2-methylphenyl]propenoate,
trifluoroacetate salt

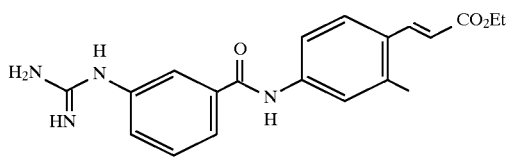

The above compound was prepared as in Example 28, Steps A–C, starting from 2-bromo-5-nitrotoluene to give the desired product.

Anal. calcd for $C_{20}H_{22}N_4O_3$+1.6 TFA+0.9 $H_2O$: C, 49.39; H, 4.56; N, 10.03. Found: C, 49.10; H, 4.65; N, 10.43.

EXAMPLE 33

3-[4-[[[3-[(aminoiminomethyl)amino]phenyl]
carbonyl]-amino]-2-methylphenyl]propenoic acid,
trifluoroacetate salt

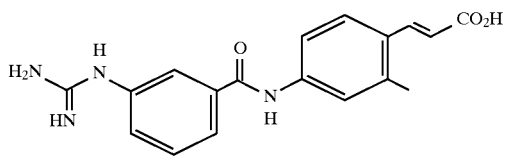

The above compound was prepared as in Example 28, Step D, starting from the product of Example 32.

Anal. calcd for $C_{18}H_{18}N_4O_3$+1.0 TFA+0.9 $H_2O$: C, 51.26, H, 4.47, N, 11.96. Found: C, 51.64, H, 4.29, N, 12.02.

EXAMPLE 34 ethyl 3-[4-[[[3-[(aminoiminomethyl)amino]phenyl]
carbonyl]amino]-2-(trifluoromethyl)phenyl]
propanoate, trifluoroacetate salt

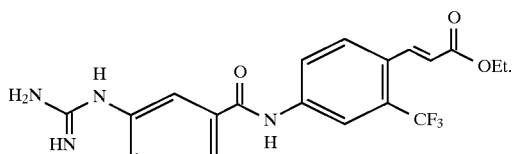

The above compound was prepared as in Example 28, Steps A–C, starting from 2-bromo-5-nitrobenzotrifluoride.

Anal. calcd for $C_{20}H_{19}N_4O_3F_3$+1.0 TFA: C, 49.45; H, 3.77; N, 10.48. Found: C, 49.29; H, 3.64; N, 10.49.

EXAMPLE 35

3-[4-[[[3-[(aminoiminomethyl)amino]phenyl]
carbonyl]amino]-2-(trifluoromethyl) phenyl]
propanoic acid, trifluoroacetate salt

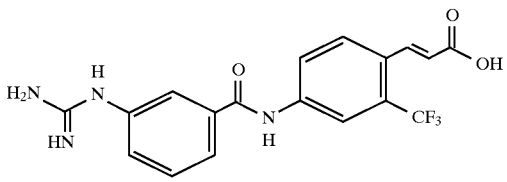

The above compound was prepared as in Example 28, Step D, starting from the product of Example 34.

Anal. calcd for $C_{18}H_{15}N_4O_3F_3$+1.3 TFA: C, 45.77; H, 3.04; N, 10.36. Found: C, 45.31; H, 3.04; N, 10.34.

EXAMPLE 36

5-[[[3-[(aminoiminomethyl)amino]phenyl]carbonyl]
amino]-2-(2-carboxyethenyl)benzoic acid,
trifluoroacetate salt

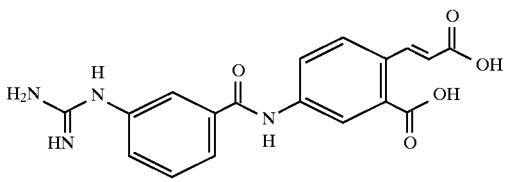

The above compound was prepared as in Example 28, Steps A–D, starting from methyl 2-bromo-5-nitrobenzoate and methyl acrylate.

Anal. calcd for $C_{18}H_{16}N_4O_5$+1.6 TFA: C, 46.23; H, 3.22; N, 10.17. Found: C, 46.24; H, 3.47; N, 9.05.

EXAMPLE 37 methyl 5-[[[3-[(aminoiminomethyl)amino]phenyl]
carbonyl]amino]-2-(2-carboxyethenyl)benzoate,
trifluoroacetate salt

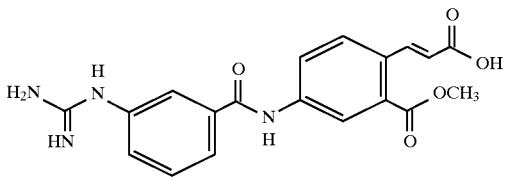

Steps A–B

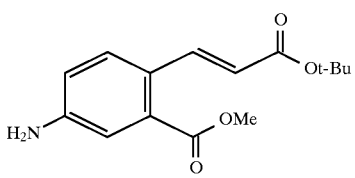

The above compound was prepared as in Example 28, Steps A–B, from methyl 2-bromo-5-nitrobenzoate and t-butyl acrylate. $^1$H NMR was consistent with the proposed structure.

Step C

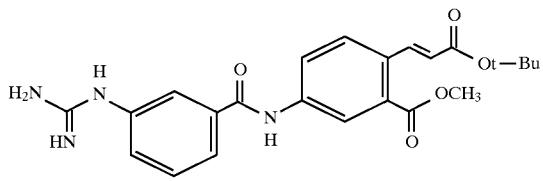

To the product of Example A (370 mg, 1.7 mmol) in DMF (5 mL) at 0° C. was added 1-hydroxybenzotriazole hydrate (HOBT, 200 mg, 1.5 mmol) and 1-(3-dimethylaminopropyl)-3-ethylcarbodiimide hydrochloride (EDCI, 300 mg, 1.6 mmol) and the mixture stirred at 0° C. for 40 minutes. The compound produced in Steps A–B (277 mg, 1.0 mmol) was added and the mixture was stirred at room temperature overnight. Purification by reverse phase HPLC (water/TFA:acetonitrile) provided the desired compound.

Anal. calcd for $C_{23}H_{26}N_4O_5$+1.4 TFA: C, 51.95; H, 4.63; N, 9.39. Found: C, 51.83; H, 4.90; N, 9.16.

Step D

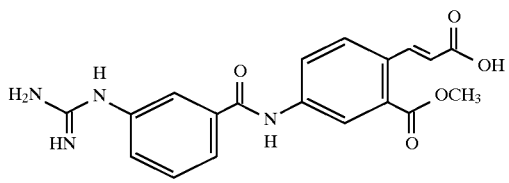

To the compound produced in Step C (50 mg, 0.11 mmol) in $CH_2Cl_2$ (2 mL) at 0° C. was added TFA (0.5 mL) and the mixture stirred at 0° C. for 30 minutes and for 90 minutes at room temperature. The solvent was removed and the crude product purified by reverse phase HPLC (water/TFA:acetonitrile) to provide the desired compound (45 mg).

Anal. calcd for $C_{19}H_{18}N_4O_5$+1.3 TFA: C, 48.89; H, 3.67; N, 10.56. Found: C, 48.64; H, 3.93; N, 10.49.

EXAMPLE 38

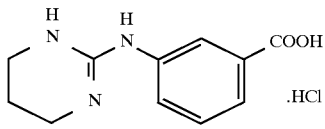

Step A

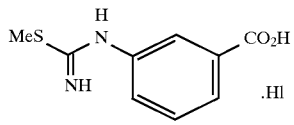

1-(3-Carboxyphenyl)-2-thiourea (5 g, 0.025 mole) in THF (75 mL) and iodomethane (3.62 g, 0.025 mole) were stirred at reflux for 2 hours. The solvent was removed under vacuum and the residue was washed with ether to yield N-(3-carboxyphenyl)-S-methylisothiouronium hydriodide (7.8 g). $^1$H NMR was consistent with the proposed structure.

Step B

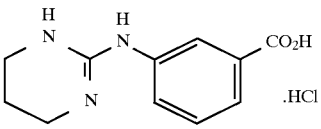

To the product of Step A (10.1 g, 0.03 mole) in DMF (15 mL) was added 1,3-diaminopropane (2.22 g, 0.03 mole), triethylamine (3.9 g, 0.03 mole), and DMAP (420 mg). The reaction mixture was heated at 140°–150° C. for 4.5 hours. After cooling to room temperature, $H_2O$ (30 mL) was added and, after stirring for 15 minutes, the precipitate was collected and washed with $H_2O$. The precipitate was slurried in $H_2O$ and made acidic with concentrated HCl. After removing the solvent, the residue was washed with isopropyl ether to afford the desired compound (4.0 g). $^1$H NMR was consistent with the proposed structure.

EXAMPLE 39 methyl 5-[[[3-[(1,4,5,6-tetrahydropyrimidine-2-yl]amino]phenyl]carbonyl]amino]-2-(2-carboxyethenyl)benzoate, trifluoroacetate salt

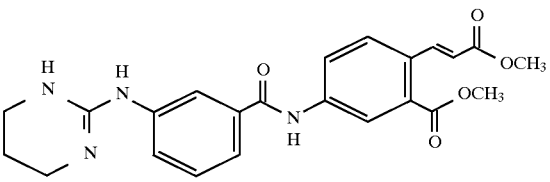

The title compound was prepared from the product of Example 36 and the product from Example 38 using the conditions described in Example 37, Step C.

Anal. calcd for $C_{23}H_{24}N_4O_5$+1.2 TFA: C, 53.22; H, 4.43; N, 9.77. Found: C, 53.02; H, 4.20; N, 9.69.

EXAMPLE 40

A 2-(2-carboxyethenyl)-5-[[[3-[(1,4,5,6-tetrahydropyrimidin-2-yl)amino]phenyl]carbonyl]amino]benzoic acid, trifluoroacetate salt

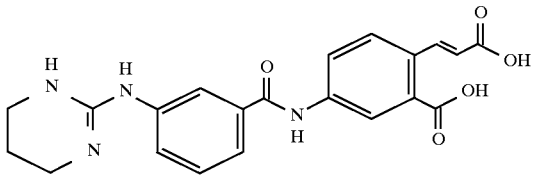

B methyl 2-(2-carboxyethenyl)-5-[[[3-[(1,4,5,6-tetrahydropyrimidin-2-yl)amino]phenyl]carbonyl]amino]benzoate, trifluoroacetate salt

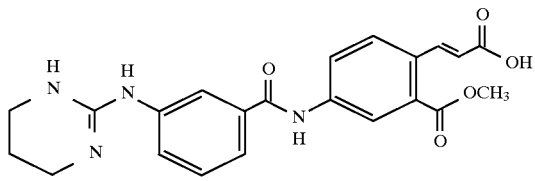

C 2-[2-(methoxycarbonyl)ethenyl]-5-[[[3-[(1,4,5,6-tetrahydropyrimidin-2-yl)amino]phenyl]carbonyl]amino]benzoic acid, trifluoroacetate salt

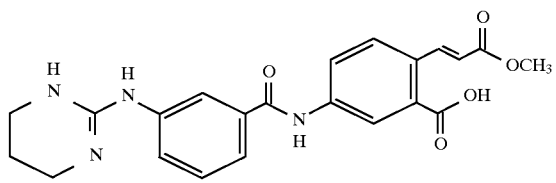

The above compounds were prepared from the product of Example 39 (100 mg) using the conditions described in Example 28, Step D to provide after reverse phase HPLC (water/TFA:acetonitrile), A, 60 mg; B, 12 mg; and C, 19 mg. $^1$H NMR and MS were consistent with the proposed structures.

EXAMPLE 41 methyl 3-[4-[[[3-[(aminoiminomethyl)amino]phenyl]carbonyl]amino]-2-(2-methoxycarbonylethenyl)phenyl]propenoate, trifluoroacetate salt

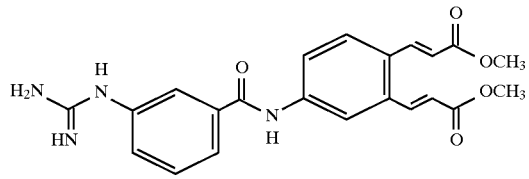

Step A

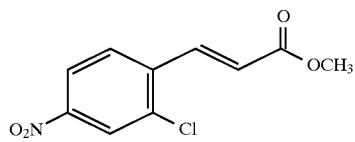

To 2-chloro-5-nitrocinnamic acid (912 mg, 4 mmol) in DMF (4 ml) was added NaHCO$_3$ (1.2 g) and MeI (1.1 g, 8 mmol) and the mixture stirred at room temperature overnight. The solvent was removed and the residue dissolved in CHCl$_3$. The solution was washed with water, dried and concentrated to provide the desired product (800 mg). $^1$H NMR was consistent with the proposed structure.

Steps B–C

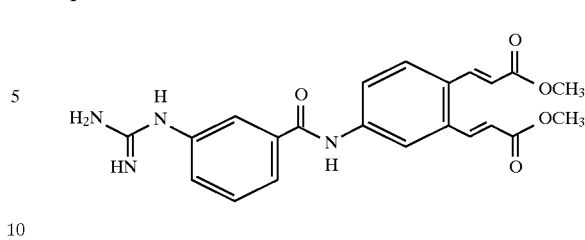

The above compound was prepared as in Example 28, Steps A–B, and Example 37, Step C starting from the product of Step A and methyl acrylate to provide, after reverse phase HPLC (CH$_3$CN/H$_2$O/TFA), the desired compound.

Anal. calcd for C$_{22}$H$_{22}$N$_4$O$_5$+1.5 TFA: C, 50.60; H, 3.99; N, 9.44. Found: C, 50.50; H, 4.18; N, 9.35.

EXAMPLE 42

3-[4-[[[3-[(aminoiminomethyl)amino]phenyl]carbonyl]amino]-2-(2-carboxyethenyl)phenyl]propenoic acid, trifluoroacetate salt

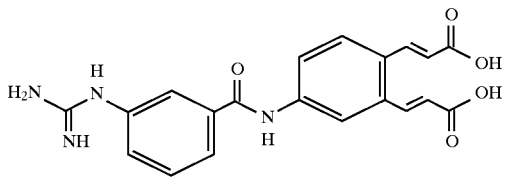

The above compound was prepared as in Example 28, Step D, starting from the product of Example 41. $^1$H NMR and MS were consistent with the proposed structure.

EXAMPLE 43 ethyl 3-[4-[[[3-[(aminoiminomethyl)amino]phenyl]carbonyl]amino]-2-cyanophenyl]propenoic acid, trifluoroacetate salt

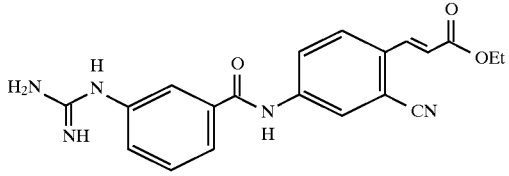

Steps A–B

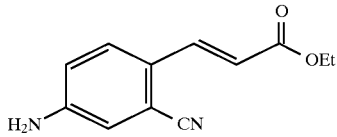

The above compound was prepared as in Example 28, Steps A–B, starting from 2-chloro-5-nitrobenzonitrile. $^1$H NMR and MS were consistent with the proposed structure.

Step C

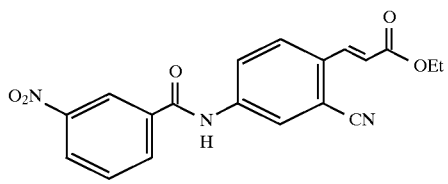

The product of Steps A–B (320 mg) and 3-nitrobenzoyl chloride (200 mg) in DMF (5 mL) were subjected to 140,000 psi pressure at room temperature for 19 hours. Concentration and purification by chromatography on silica gel (EtOAc/toluene) furnished the desired compound (120 gel (EtOAc/toluene) furnished the desired compound (120 mg). $^1$H NMR and MS were consistent with the proposed structure.

Step D

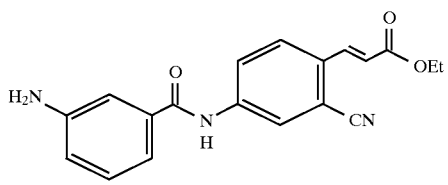

The product of Step C (120 mg) was subjected to the conditions described in Example 28, Step B to afford the desired compound (25 mg). $^1$H NMR was consistent with the proposed structure. Steps E–F

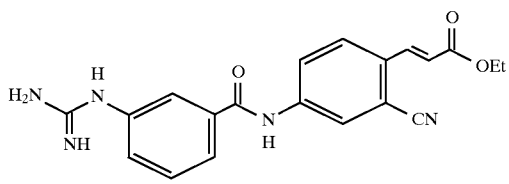

The above compound was prepared as in Example 5, Steps D–E, starting from the product of Step D. $^1$H NMR was consistent with the proposed structure.

Anal. calcd for $C_{20}H_{20}N_4O_3 + 2.0$ TFA: C, 47.53; H, 3.66; N, 11.55. Found: C, 47.53; H, 3.45; N, 12.16.

EXAMPLE 44

3-[4-[[[3-[(aminoiminomethyl)amino]phenyl] carbonyl]amino]-2-cyanophenyl]propenoic acid, trifluoroacetate salt

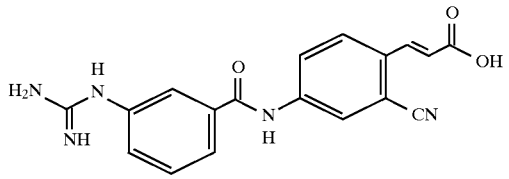

The above compound was prepared as in Example 28, Step D, starting from the product of Example 43.

Anal. calcd for $C_{18}H_{15}N_5O_3 + 1.3$ TFA: C, 49.73; H, 3.30; N, 14.07. Found: C, 49.45; H, 3.19; N, 14.09.

EXAMPLE 45

3-[2-[(methylamino)carbonyl]-4-[[[3-[(1,4,5,6-tetrahydropyrimidin-2-yl)amino]phenyl]carbonyl] amino]phenyl]propenoic acid, bis(trifluoroacetate) salt

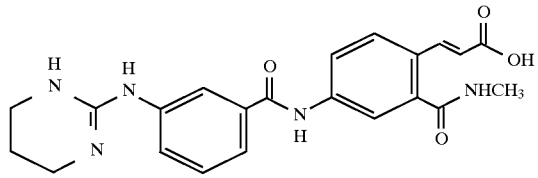

Step A

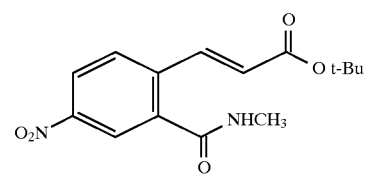

The product of Example 37, Step A (1.0 g, 3.3 mmol) was saponified as described in Example 28, Step D to provide the crude carboxylic acid. This compound was stirred in toluene (60 mL) with $SOCl_2$ (0.5 mL) at 65° C. overnight. The mixture was concentrated to about half the volume and cooled to 0° C. Triethylamine (0.42 mL, 3 mmol) and 2.0M methylamine in THF (1.5 mL, 3 mmol) were added to the crude acid chloride and the mixture stirred at 0° C. for 30 minutes and at room temperature overnight. Concentration and purification by chromatography on silica gel (EtOAc/toluene) provided the desired amide (300 mg). $^1$H NMR was consistent with the proposed structure.

Step B

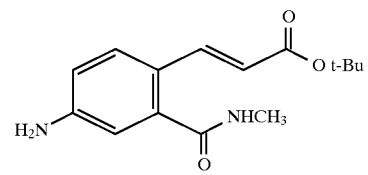

The product of Step A (300 mg) was subjected to the conditions described in Example 28, Step B to afford, after purification by chromatography on silica gel (EtOAc/TEA) the desired compound (250 mg). $^1$H NMR was consistent with the proposed structure.

Step C

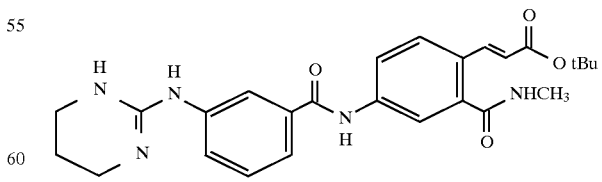

The product of Step B (100 mg) was subjected to the conditions described in Example 39, to afford the desired compound.

Anal. calcd for $C_{26}H_{31}N_5O_4 + 1.5$ TFA: C, 53.70; H, 5.05; N, 10.80. Found: C, 53.96; H, 5.34; N, 11.14.

Step D

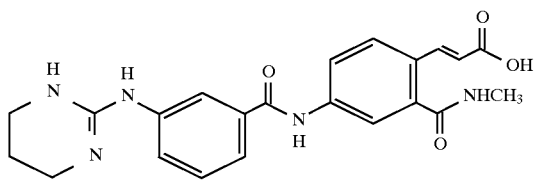

The above compound was prepared as in Example 37, Step D, starting from the product of Step C.

Anal. calcd for $C_{22}H_{23}N_5O_4+2.7$ TFA: C, 45.12; H, 3.55; N, 9.60. Found: C, 44.86; H, 3.82; N, 10.22.

EXAMPLE 46

3-[2-[(ethoxycarbonyl)amino]-4-[[[3-[(1,4,5,6-tetrahydropyrimidin-2-yl)amino]phenyl]carbonyl]amino]phenyl]propenoic acid, trifluoroacetate salt

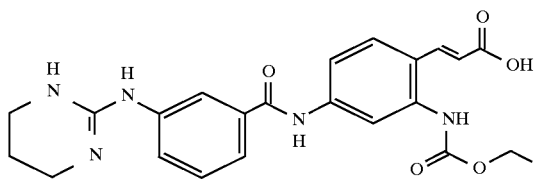

Step A

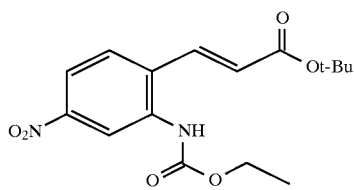

To a solution of the crude acid chloride intermediate from Example 45, Step A (1.2 g, 3.8 mmol) and tetra-n-butylammonium bromide (3 mg) in $CH_2Cl_2$ (5 mL) at 0° C. was added a solution of $NaN_3$ (300 mg) in water (2 mL) and the mixture stirred at 0° C. for 2 hours. The organic layer was separated, washed with water, dried over $MGSO_4$, filtered and concentrated to provide the crude acyl azide. The compound was stirred in refluxing toluene (20 mL) for 2 hours and the mixture cooled and concentrated. EtOH (10 mL) was added, followed by NaOEt (200 mg, 3 mmol), and the mixture stirred at room temperature for 4 hours. The solvent was removed and the residue dissolved in toluene and filtered. The filtrate was concentrated and purified by flash chromatography (EtOAC/toluene) to provide the desired product (1.0 g). $^1H$ NMR was consistent with the proposed structure.

Step B

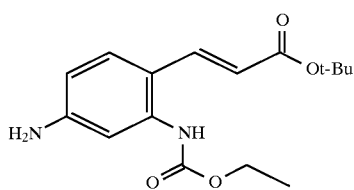

The above compound was prepared as in Example 28, Step B, starting from the product of Step A. $^1H$ NMR was consistent with the proposed structure.

Step C

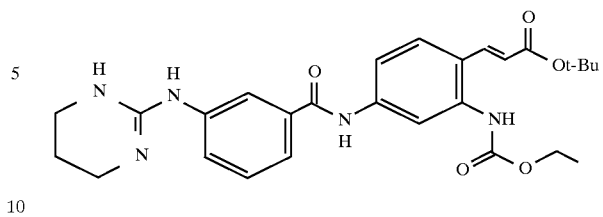

The above compound was prepared as in Example 39 starting from the product of Step B.

Anal. calcd for $C_{27}H_{33}N_5O_5+1.6$ TFA: C, 52.57; H, 5.05; N, 10.15. Found: C, 52.26; H, 5.68; N, 10.05.

Step D

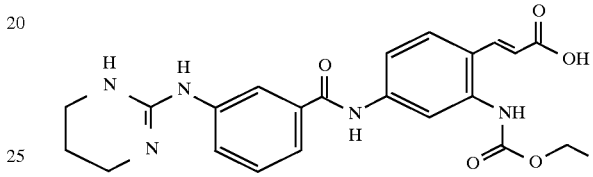

The above compound was prepared as in Example 37, Step D, starting from the product of Step C.

Anal. calcd for $C_{23}H_{25}N_5O_5+1.8$ TFA: C, 48.65; H, 4.11; N. 10.66. Found: C, 48.34; H, 4.33; N, 11.22.

EXAMPLE 47

2-(dimethylamino)-2-oxoethyl 3-[4-[[[3-[(aminoiminomethyl)amino]phenyl]carbonyl]amino]phenyl]propenoate, trifluoroacetate salt

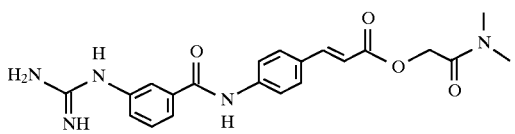

Step A

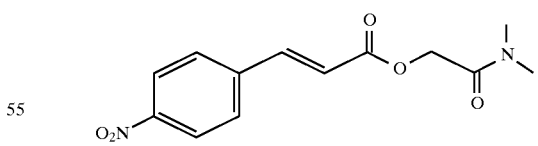

To a stirred solution of 4-nitrocinnamic acid (360 mg, 1.83 mmol), DMF (5 ml) and $K_2CO_3$ (360 mg) was added 2-chloro-N,N-dimethylacetamide (226 mg, 1.86 mmole). The mixture was stirred at 70°–75° C. for 2 hours. The mixture was cooled to room temperature, diluted with ice water, and extracted with ethyl acetate. The organic solution was dried over sodium sulfate and concentrated in vacuo to afford the desired product (406 mg). $^1H$ NMR was consistent with the proposed structure.

Step B

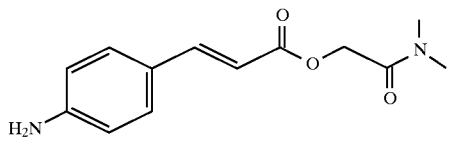

The above compound was prepared as in Example 28, Step B starting from the product of Step A. $^1$H NMR was consistent with the proposed structure.

Step C

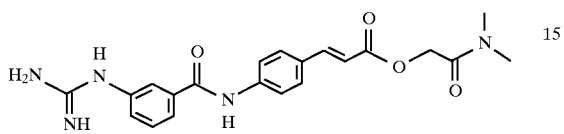

The above compound was prepared as in Example 28, Step C, starting from the product of Step B.

Anal. calcd for $C_{21}H_{23}N_5O_4+1.0$ TFA, 0.5 $H_2O$: C, 51.88; H, 4.73; N, 13.15. Found: C, 51.61; H, 4.37; N, 13.07.

EXAMPLE 48

2-(dimethylamino)-2-oxoethyl 3-[4-[[[3-[(1,4,5,6-tetrahydropyrimidin-2-yl)amino]phenyl]carbonyl]amino]phenyl]propenoate, trifluoroacetate salt

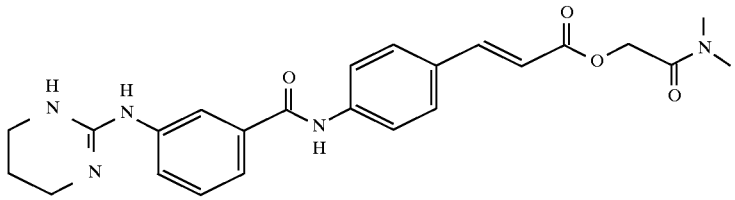

The above compound was prepared as in Example 39, starting from the product of Example 47, Step B.

Anal. calcd for $C_{24}H_{27}N_5O_4+1.0$ TFA+0.25 $H_2O$: C, 54.98; H, 5.06; N, 12.33. Found: C, 54.77; H, 4.98; N, 12.19.

EXAMPLE 49

3-[4-[[[3-[(1,4,5,6-tetrahydropyrimidin-2-yl)amino] phenyl]carbonyl]amino]phenyl]propenoic acid, trifluoroacetate salt

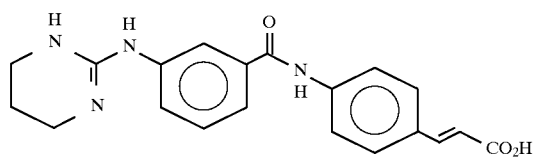

Steps A–C

The above compound was prepared as in Example 18, Steps A–B, followed by the procedure of Example 21, Step C, starting with ethyl 4-aminocinnamate. $^1$H NMR was consistent with the proposed structure.

Anal. calcd for $C_{20}H_{20}N_4O_3+1.7$ TFA+0.7 $H_2O$: C, 49.23; H, 4.08; N, 9.81. Found: C, 49.09; H, 3.70; N, 10.00.

EXAMPLE 50

3-[2-methoxy-4-[[[3-[(1,4,5,6-tetrahydropyrimidin-2-yl)amino]phenyl]carbonyl]amino]phenyl] propenoic acid, trifluoroacetate salt

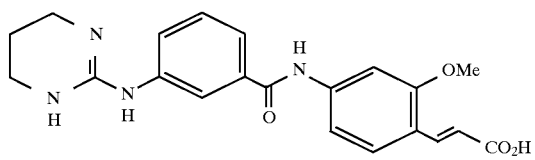

The above compound was prepared as in Example 28, Step C, starting from the product of Example 30, Step B and the product of Example 38.

Anal. calcd for $C_{21}H_{22}N_4O_4+1.2$ TFA: C, 52.90; H, 4.40; N, 10.55. Found: C, 52.76; H, 4.69; N, 10.61.

EXAMPLE 51

3-[2-chloro-4-[[[3-[(1,4,5,6-tetrahydropyrimidin-2-yl)amino]phenyl]carbonyl]amino]phenyl]propenoic acid, trifluoroacetate salt

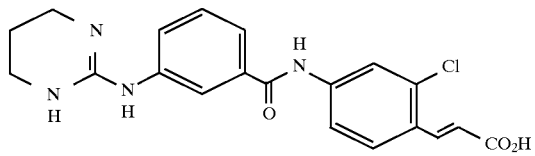

The above compound was prepared as in Example 28, Step C, starting from the product of Example 28, Step B and the product of Example 38.

Anal. calcd for $C_{20}H_{19}N_4O_3+1.0$ TFA+0.6 $H_2O$: C, 50.46; H, 4.08; N, 10.70. Found: C, 50.36; H, 3.99; N, 10.81.

EXAMPLE 52

3-[4-[[[3-[[amino[(aminocarbonyl)imino)methyl]amino]phenyl]carbonyl]amino]phenyl]propenoic acid, trifluoroacetate salt

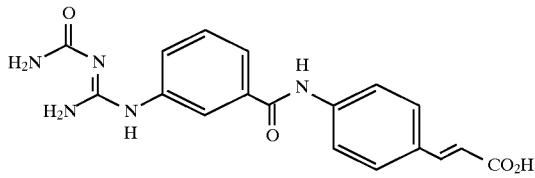

Step A

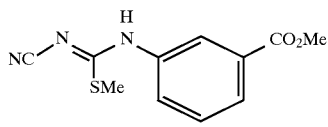

A stirred mixture of methyl 3-aminobenzoate (6.04 g, 40 mmol) and dimethyl N-cyanodithioiminocarbonate (11.96 g, 80 mmol) in pyridine (70 mL) was heated at reflux under a nitrogen atmosphere for 2.5 hours. The reaction mixture was cooled to room temperature. On standing overnight at room temperature the above compound crystallized from the reaction mixture to yield 6.2 g (two crops). The above compound was used without further purification in the proceeding examples. $^1$H NMR was consistent with the proposed structure.

Step B

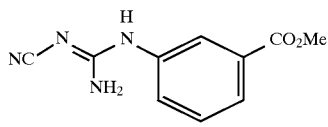

A mixture of the product from Step A (1.0 g) and ammonium hydroxide (2 mL) in ethanol (20 mL) was heated at 70° C. in a sealed tube for 3.5 hours. The reaction mixture was cooled to room temperature and reduced to half its volume. After standing overnight at room temperature a white solid was obtained, which was isolated by filtration and washed with methanol to give the desired compound (389 mg). $^1$H NMR was consistent with the proposed structure.

Step C

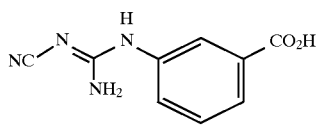

To a stirred solution of the product from Step B (2.9 g, 13.3 mmol) in THF (15 mL) and methanol (15 mL), was added 1N NaOH (14 mL). The reaction mixture was stirred at room temperature for 2 hours and concentrated in vacuo to afford a white solid. The residue was acidified by suspension in water followed by addition of 1N HCl. The resultant solid was filtered, washed with diethyl ether, and dried to afford the above compound (2.4 g). $^1$H NMR was consistent with the proposed structure.

Step D

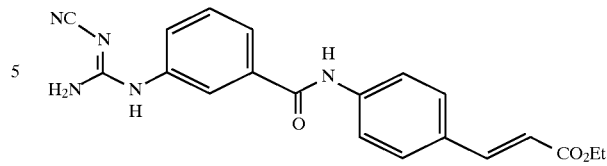

The above compound was prepared as in Example 28, Step C, starting from the product of Step C and ethyl 4-aminocinnamate. $^1$H NMR was consistent with the proposed structure.

Step E

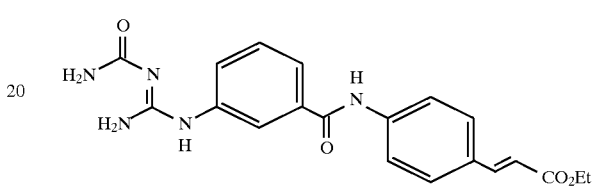

To a stirred solution of the product of Step D (0.23 g, 0.58 mmol) in $CH_2Cl_2$ (4 mL) was added TFA (4 mL). The reaction mixture was stirred at 25° C. for 2 hours. The reaction mixture was concentrated in vacuo to afford a brown oil. $^1$H NMR was consistent with the proposed structure.

Step F

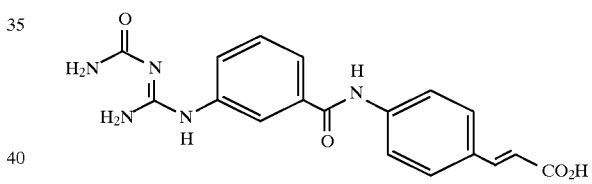

The above compound was prepared as in Example 21, Step C starting from the product of Step E. $^1$H NMR and elemental analysis were consistent with the proposed structure.

Anal. calcd for $C_{18}H_{17}N_5O_4$+0.6 TFA: C, 52.92; H, 4.07; N, 16.07. Found: C, 52.90; H, 4.39; N, 15.91.

EXAMPLE 53

3-[4-[[[3-[(aminoiminomethyl)amino]-5-(trifluoromethyl)-phenyl]carbonyl]amino]phenyl]propenoic acid, trifluoroacetate salt

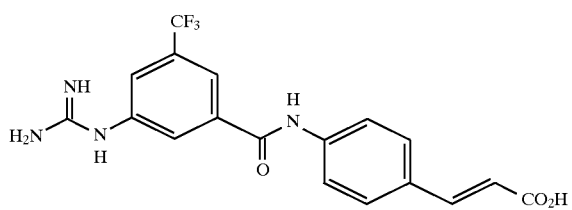

Step A

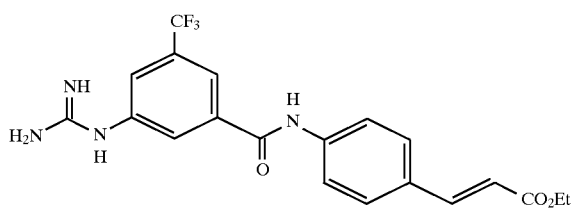

The above compound was prepared as in Example 28, Step C, starting from the product of Example B and ethyl 4-aminocinnamate. $^1$H NMR was consistent with the proposed structure.

Step B

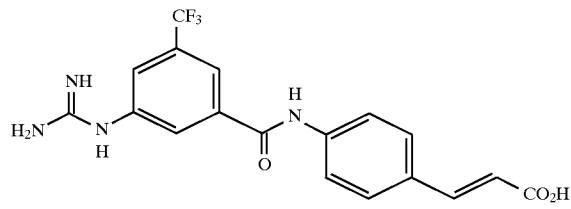

The above compound was prepared as in Example 21, Step C starting from the product of Step A.

Anal. calcd for $C_{18}H_{15}N_4O_3F_3$+1.2 TFA: C, 46.30; H, 3.09; N, 10.59. Found: C, 45.99; H, 3.20; N, 10.72.

EXAMPLE 54

3-[4-[[[3-[(aminoiminomethyl)amino]-5-(trifluoromethyl) phenyl]carbonyl]amino]-2-chlorophenyl]propenoic acid, trifluoroacetate salt

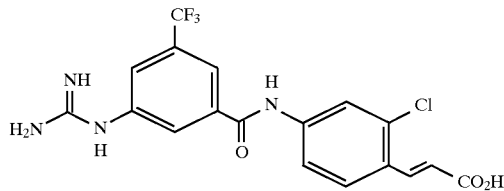

The above compound was prepared as in Example 53, Steps A–B starting from the product of Example B and Example 28, Step B.

Anal. calcd for $C_{18}H_{14}N_4O_3ClF_3$+1.0 TFA+0.8 $H_2O$: C, 43.27; H, 3.01; N, 10.09. Found: C, 43.09; H, 2.72; N, 10.23.

EXAMPLE 55

3-[4-[[[3-[(aminoiminomethyl)amino]-5-(trifluoromethyl)phenyl]carbonyl]amino]-2-methoxyphenyl]propenoic acid, trifluoroacetate salt

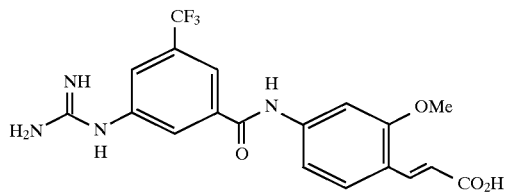

The above compound was prepared as in Example 53, Steps A–B starting from the product of Example B and Example 30, Step B.

Anal. calcd for $C_{19}H_{17}N_4O_3F_3$+1.5 TFA+0.5 $H_2O$: C, 43.86; H, 3.26; N, 9.30. Found: C, 43.82; H, 3.00; N, 9.59.

EXAMPLE 56

3-[4-[[[3-[(5,6-dihydro-4H-1,3-thiazin-2-yl)amino] phenyl]carbonyl]amino]phenyl]propenoic acid, trifluoroacetate salt

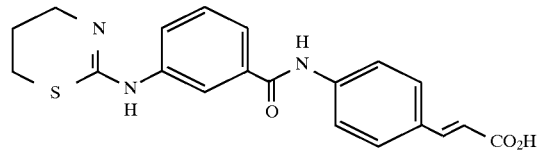

The above compound was prepared as in Example 100 starting with 2-methylthio-5,6-dihydro-4H-1,3-thiazine and ethyl 4-aminocinnamate.

Anal. calcd for $C_{20}H_{19}N_3O_3S$+1.2 TFA: C, 51.91; H, 3.93; N, 8.11. Found: C, 52.29; H, 3.76; N, 8.36.

EXAMPLE 57

3-[4-[[[3-[(5,6-dihydro-4H-1,3-thiazin-2-yl)amino] phenyl]carbonyl]amino]3,5-dimethylphenyl] propenoic acid, trifluoroacetate salt

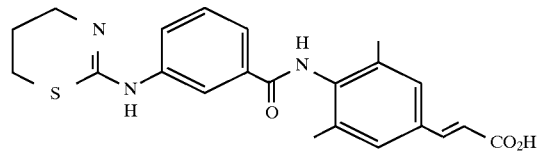

The above compound was prepared as in Example 100 starting with 2-methylthio-5,6-dihydro-4H-1,3-thiazine and the product from Example 14, Step A.

Anal. calcd for $C_{22}H_{23}N_3O_3S$+1.3 TFA: C, 52.98; H, 4.39; N, 7.53. Found: C, 52.63; H, 4.47; N, 7.55.

EXAMPLE 58

3-[4-[[[3-[(aminoiminomethyl)amino]phenyl]-carbonyl]amino]phenyl]-3-phenylpropenoic acid, trifluoroacetate salt

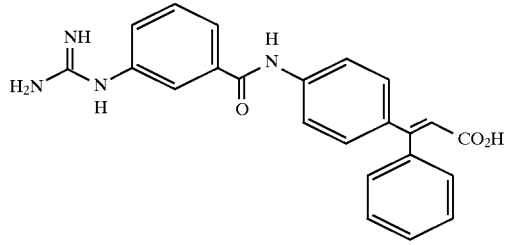

Step A

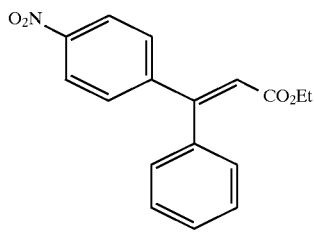

A suspension of 60% NaH in mineral oil (washed with hexane before use, 1.5 g, 37.5 mmol) in THF (50 mL) was cooled to 0° C. and ethyl dimethylphosphonoacetate (3.95 mL, 24 mmol) was added very slowly under argon. Vigorous bubbling was observed and the reaction eventually became a white slurry. The reaction was allowed to stir at 0° C. for 1.5 hours before adding a solution of 4-nitrobenzophenone (5 g, 22 mmol) in THF (10 mL). The reaction was allowed to warm to room temperature. After 4 hours, the reaction was quenched with water (50 mL) and extracted with EtOAc (2×60 mL). The organic layers were collected, dried, and concentrated in vacuo. The crude product was purified by chromatography on silica (20:80 EtOAc/Hexane) to give two isomers. The major isomer was used for the following reaction. $^1$H NMR spectrum was consistent with proposed structure.

Step B

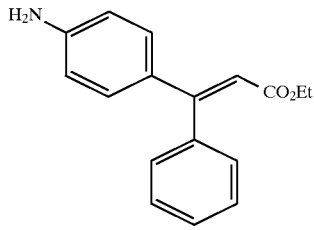

The above compound was prepared as in Example 5, Step C starting from the product of Step A. $^1$H NMR spectrum was consistent with proposed structure.

Step C

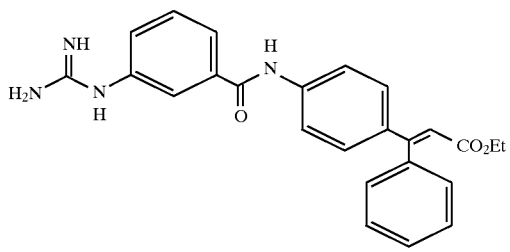

The above compound was prepared as in Example 28, Step C starting from the product of Step B. $^1$H NMR spectrum was consistent with proposed structure.

Step D

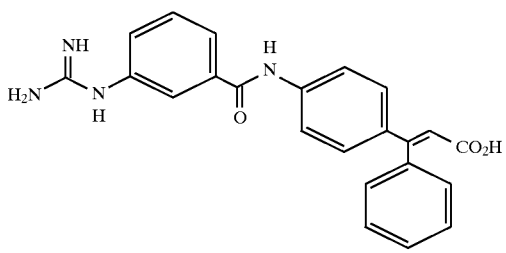

The above compound was prepared as in Example 21, Step C starting from the product of Step C.

Anal. calc'd for $C_{23}H_{20}N_4O_3$+1.3 TFA: C, 56.04; H, 3.91; N, 10.21. Found: C, 55.89; H, 4.00; N, 10.31.

EXAMPLE 59

3-[4-[[[3-[(aminoiminomethyl)amino]phenyl] carbonyl]amino]phenyl]-2-butenoic acid, trifluoroacetate salt

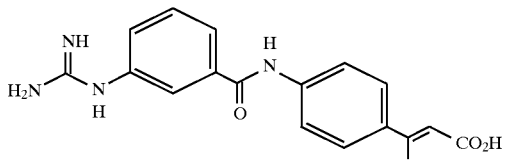

The above compound was prepared as in Example 58, Steps A–D, starting from 4-nitroacetophenone. $^1$H NMR spectrum was consistent with proposed structure.

Anal. calcd for $C_{18}H_{18}N_4O_3$+1.2 TFA: C, 51.56; H, 4.07; N, 11.79. Found: C, 51.39; H, 3.96; N, 11.84.

EXAMPLE 60

3-[4-[[[3-[(aminoiminomethyl)amino]phenyl] carbonyl]amino]phenyl]-2-[(phenylcarbonyl)amino] propenoic acid, trifluoroacetate salt

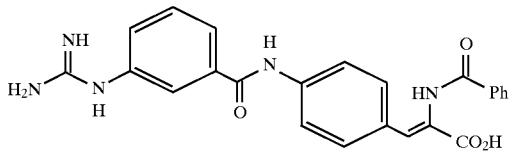

Step A

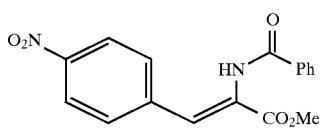

A mixture of 4-nitrobenzaldehyde (3.2 g, 20 mmol) and hippuric acid (3.58 g, 20 mmol) in acetic anhydride (25 mL) was heated to 80° C. for 4 hours. Upon heating, the mixture became a yellow solid. The reaction mixture was allowed to cool to room temperature. The yellow precipitate was collected by vacuum filtration and washed with water. The yellow solid (3.5 g, 6.8 mmol) was dissolved in MeOH (20 mL) and potassium carbonate (0.94 g, 6.8 mmol) was added. The reaction mixture was heated to 60° C. for 2 hours. The reaction mixture was allowed to cool to room temperature and concentrated under reduced pressure. Water was added to the residue and resulting in a yellow solid which was collected by vacuum filtration to afford the desired product (1.5 g). $^1$H NMR spectrum was consistent with proposed structure.

Step B

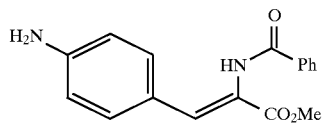

The above compound was prepared as in Example 5, Step C starting from the product of Step A. $^1$H NMR was consistent with proposed structure.

Step C

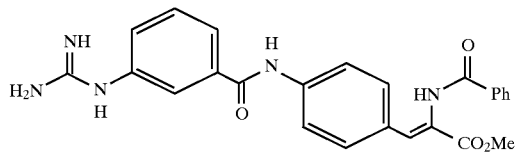

The above compound was prepared as in Example 28, Step C. $^1$H NMR was consistent with proposed structure.

Step D

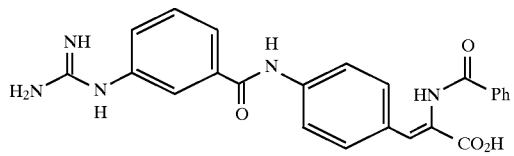

The above compound was prepared as in Example 21, Step C starting from the product of Step C.

Anal. calcd for $C_{24}H_{21}N_5O_4$+1.4 TFA: C, 53.37; H, 3.74; N, 11.61. Found: C, 53.35; H, 3.71; N, 11.91.

EXAMPLE 61 ethyl 3-[3-[[[[3-[(1,4,5,6-tetrahydropyrimidin-2-yl)-amino]phenyl]carbonyl]amino]methyl]phenyl] propenoate, trifluoroacetate salt

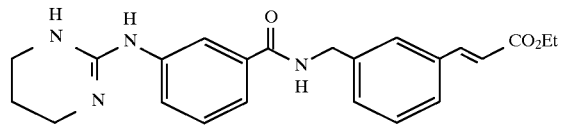

The above compound was prepared as in Example 28, Step C starting from the product of Example 38 and the product of Example 1, Step C.

Anal. calcd for $C_{23}H_{26}N_4O_3$: C, 67.96; H, 6.45; N, 13.78. Found: C, 67.81; H, 6.55; N, 13.59.

EXAMPLE 62

3-[3-[[[[3-[(1,4,5,6-tetrahydropyrimidin-2-yl)amino] phenyl]carbonyl]amino]methyl]phenyl]propenoic acid, monohydrochloride

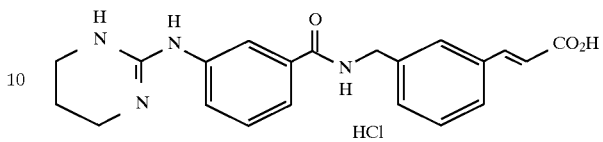

The above compound was prepared as in Example 28, Step D starting from the product of Example 61.

Anal. calcd for $C_{21}H_{22}$; $N_4O_3$+1.0 HCl:

C, 60.79; H, 5.59; N, 13.50; Cl, 8.55. Found: C, 60.39; H, 5.75; N, 13.21; Cl, 8.69.

EXAMPLE 63 ethyl 3-[3-[[[[3-[[[(phenylmethyl)amino]carbonyl] amino]phenyl]carbonyl]amino]methyl]phenyl] propenoate, trifluoroacetate salt

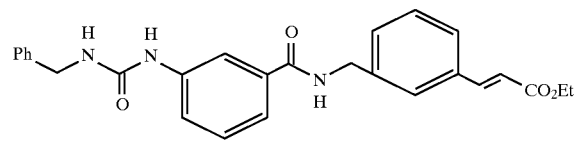

Step A

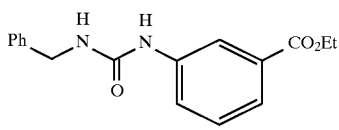

A solution of benzylisocyanate (5 g, 37 mmoles) and ethyl 3-aminobenzoate (6.2 g, 37 mmoles) in benzene (75 mL) was heated at reflux for 1 hour. After cooling, the precipitate was filtered and air dried to give the desired product (9.68 g). $^1$H NMR was consistent with the proposed structure.

Step B

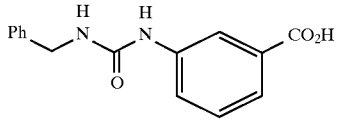

A solution of the compound from Example 63, Step A (9.67 g, 32 mmoles) and LiOH (32 ml of a 2M solution) in EtOH (150 mls) was refluxed 1 hour, cooled and the solvent evaporated. The residue was dissolved in water and HCl (0.5N) was added and the precipitate filtered and air dried to give the desired product (8.4 g). $^1$H NMR was consistent with the proposed structure.

Step C

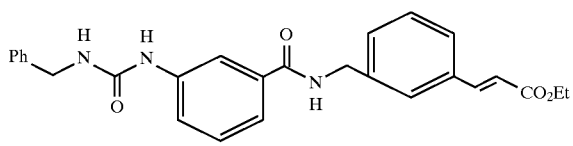

The above compound was prepared as in Example 28, Step C starting from the product of Step B and ethyl 3-aminocinnamate.

Anal. calcd for $C_{27}H_{27}N_3O_4$: C, 70.88; H, 5.95; N, 9.18. Found: C, 70.61; H, 6.16; N, 8.89.

EXAMPLE 64

3-[3-[[[[3-[[[(phenylmethyl)amino]carbonyl]amino] phenyl]carbonyl]amino]methyl]phenyl]propenoic acid, trifluoroacetate salt

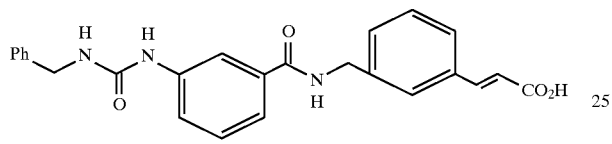

The above compound was prepared as in Example 28, Step D starting from the product of Example 63, Step C.

Anal. calcd for $C_{25}H_{23}N_3O_4+0.5\ H_2O$: C, 68.48; H, 5.52; N, 9.58. Found: C, 68.24; H, 5.29; N, 9.58.

EXAMPLE 65

3-[3-[[[[3-[[4,5-dihydro-1-[(2-methylpropoxy) carbonyl]-1H-imidazol-2-yl]amino]phenyl]carbonyl] amino]methyl]phenyl]propenoic acid, monohydrochloride hydrate

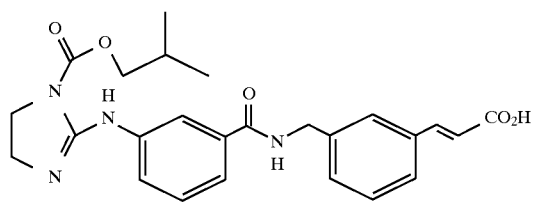

Step A

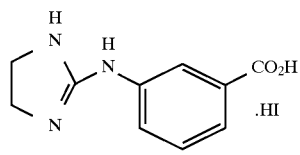

The product from Example 38, Step A (8.0 g, 24 mmol) was treated dropwise with ethylene diamine (1.75 g, 1.1 equivalent) and warmed to 100° C. slowly. After cooling, HCl (2.4N, 40 mL) was added to effect solution. The solution was cooled to 5° C. and NaOH added to pH=7. The precipitate was filtered and air dried to give the desired product (7.9 g). $^1$H NMR was consistent with the proposed structure.

Step B

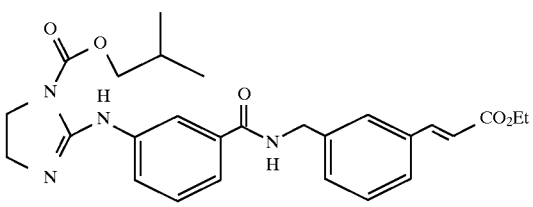

The above compound was prepared as in Example 28, Step C starting from the product of Step A and the product of Example 1, Step C. $^1$H NMR was consistent with the proposed structure.

Step C

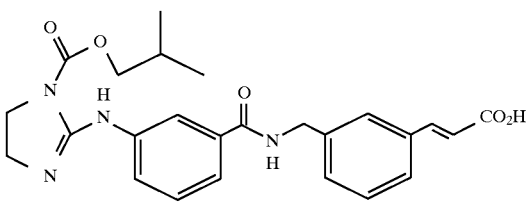

The above compound was prepared as in Example 28, Step D starting from the product of Step B.

Anal. calcd for $C_{25}H_{28}N_4O_5+1.0\ H_2O+1.0\ HCl$: C, 57.09; H, 5.79; N, 11.09; Cl, 7.02. Found: C, 56.81; H, 5.69; N, 11.00; Cl, 7.44.

EXAMPLE 66 ethyl 3-[3-[[[[3-[(4,5-dihydro-1H-imidazol-2-yl) amino]phenyl]carbonyl]amino]methyl]phenyl] propenoate, hydrate

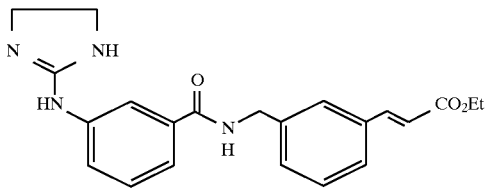

Step A

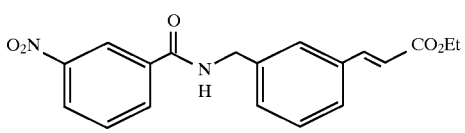

The above compound was prepared as in Example 28, Step C starting from the product of Example 1, Step C and 3-nitrobenzoic acid. $^1$H NMR was consistent with the proposed structure.

Step B

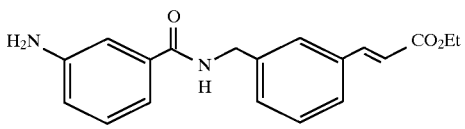

The above compound was prepared as in Example 5, Step C starting from the product of Step A. $^1$NMR was consistent with the proposed structure.

Steps C–D

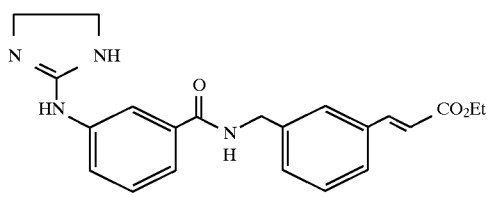

The above compound was prepared as in Example 21, Steps A–B starting from the product of Step B.

Anal. calcd for $C_{22}H_{24}N_4O_3 + 1.0\ H_2O$: C, 64.38; H, 6.38; N, 13.65. Found: C, 64.11; H, 6.21; N, 13.40.

EXAMPLE 67

3-[3-[[[[3-[(4,5-dihydro-1H-imidazol-2-yl)amino]phenyl]carbonyl]amino]methyl]phenyl]propenoic acid, monohydrochloride hydrate

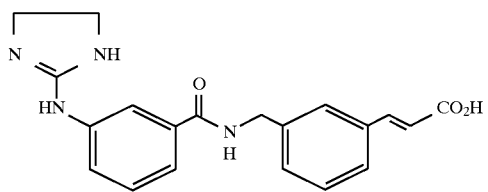

The above compound was prepared as in Example 28, Step D starting from the product of Example 66.

Anal. calcd for $C_{20}H_{20}N_4O_3 + 1.0\ HCl + 1.0\ H_2O$: C, 57.35; H, 5.53; N, 13.38. Found: C, 57.11; H, 5.29; N, 12.99.

EXAMPLE 68 ethyl 3-[3-[[[[3-[(1,4,5,6-tetrahydropyrimidin-2-yl)amino]-5-(trifluoromethyl)phenyl]carbonyl]amino]methyl]phenyl]propenoate, dihydrochloride hydrate

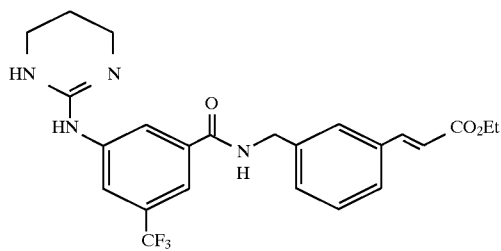

Step A

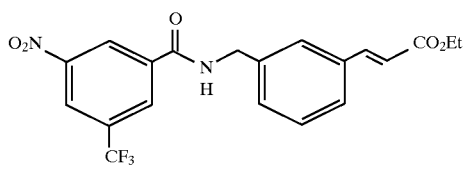

The above compound was prepared as in Example 28, Step C starting from the product of Example 1, Step C and 3-trifluoromethyl-5-nitrobenzoic acid. $^1$H NMR was consistent with the proposed structure.

Step B

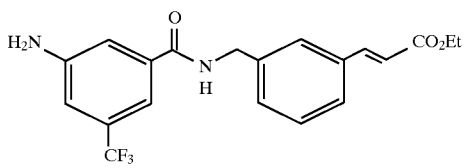

The above compound was prepared as in Example 5, Step C starting from the product of Step A. $^1$H NMR was consistent with the proposed structure.

Step C–D

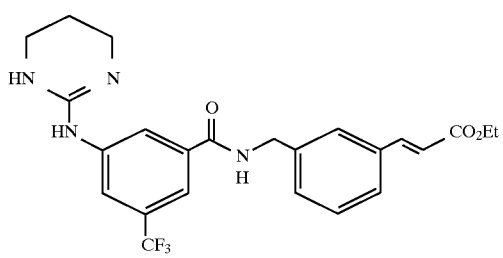

The above compound was prepared as in Example 18, Steps A–B starting from the product of Step B. $^1$H NMR was consistent with the proposed structure.

EXAMPLE 69

3-[3-[[[[3-[(1,4,5,6-tetrahydropyrimidin-2-yl)amino]-5-(trifluoromethyl)phenyl]carbonyl]amino]methyl]phenyl]propenoic acid, dihydrochloride hydrate

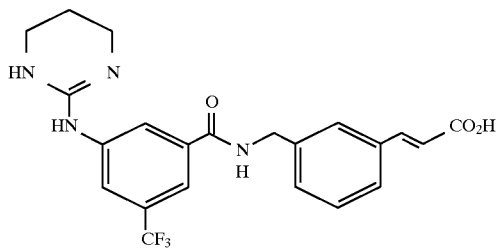

The above compound was prepared as in Example 28, Step D starting from the product of Example 68.

Anal. calcd for $C_{22}H_{21}N_4F_3O_3 + 2.0\ HCl + 1.0\ H_2O$: C, 49.17; H, 4.69; N, 10.43. Found: C, 49.48; H, 4.39; N, 10.33.

EXAMPLE 70 ethyl 3-[3-[[[[3-[(4,5-dihydro-1H-imidazol-2-yl)amino]-5-(trifluoromethyl)phenyl]carbonyl]amino]methyl]phenyl]propenoate, monohydrochloride hydrate

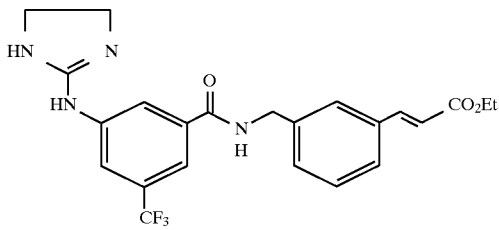

The above compound was prepared as in Example 21, Steps A–B starting from the product of Example 68, Step B. ¹H NMR was consistent with the proposed structure.

EXAMPLE 71

3-[3-[[[[3-[(4,5-dihydro-1H-imidazol-2-yl)amino]-5-(trifluoromethyl)phenyl]carbonyl]amino]methyl]phenyl]propenoic acid, monohydrochloride hydrate

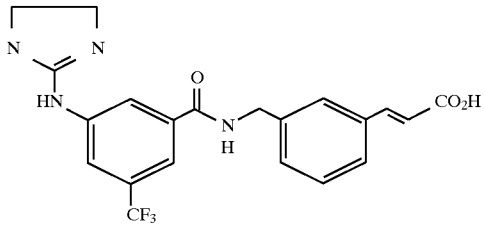

The above compound was prepared as in Example 28, Step D starting from the product of Example 70.

Anal. calcd for $C_{21}H_{19}F_3N_4O_3+1.0$ HCl+1.0 $H_2O$: C, 51.81; H, 4.55; N, 11.51; Cl, 7.28. Found: C, 51.74; H, 4.40; N, 11.31; Cl, 7.58.

EXAMPLE 72 ethyl 3-[3-[[[[3-[(2-pyrimidinyl)amino]phenyl]carbonyl]amino]methyl]phenyl]propenoate, trifluoroacetate salt

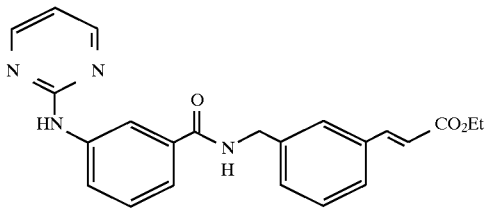

Step A

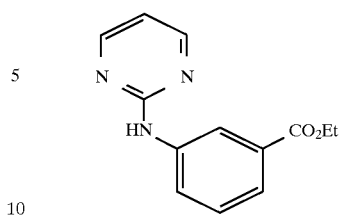

Ethyl 3-aminobenzoate (2.0 g, 12 mmol) and 2-chloropyrimidine (1.4 g, 12 mmol) were heated at 100° C. for 1 hour. The reaction mixture was cooled and diluted with MeOH (20 mL) and poured into water. The precipitate was filtered and air dried to give the desired product (2.15 g)

Anal. calcd for $C_{13}H_{13}N_3O_2$: C, 64.19; H, 5.39; N, 17.27. Found: C, 64.09; H, 5.27; N, 17.03.

Step B

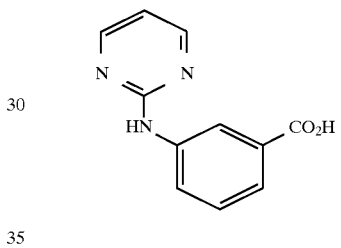

The product from Step A (2.1 g, 8.6 mmoles) was dissolved in EtOH/water (25 mL/5 mL) with warming. NaOH (1.0 g, 3 equivalents) was added and stirred at 25° C. for 3 hours. The solvent was evaporated and the residue dissolved in water (15 mL). The aqueous solution was acidified with 0.5N HCl to pH=6. The precipitate was filtered and dried in a vacuum oven to give the desired product (1.8 g). ¹H NMR was consistent with the proposed structure.

Step C

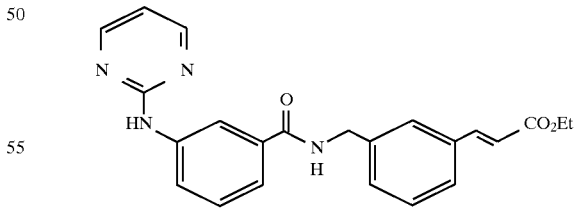

The above compound was prepared as in Example 28, Step C starting from the product of Example 1, Step C and the product of Step B.

Anal. calcd for $C_{23}H_{22}N_4O_3$: C, 68.64; H, 5.51; N. 13.92. Found: C, 68.55; H, 5.59; N, 13.78.

EXAMPLE 73

3-[3-[[[[3-[(2-pyrimidinyl)amino]phenyl]carbonyl]amino]methyl]phenyl]propenoic acid, trifluoroacetate salt

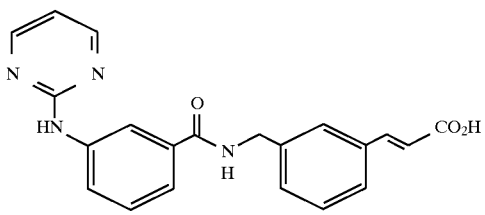

The above compound was prepared as in Example 28, Step D starting from the product of Example 72.

Anal. calcd for $C_{21}H_{18}N_4O_3 + 1.0\ HCl + 1.0\ H_2O$: C, 58.81; H, 4.94; N, 13.06. Found: C, 58.59; H, 4.60; N, 13.04.

EXAMPLE 74

3-[3-[[[[3-[(aminoiminomethyl)amino]phenyl]carbonyl]amino]methyl]phenyl]-2E-pentenoic acid, trifluoroacetate salt hydrate

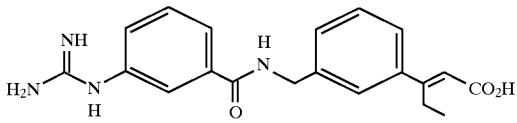

Step A

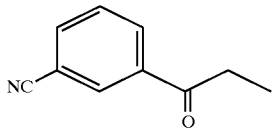

A solution of 3-acetylbenzonitrile (1.02 g, 7.0 mmol) in THF (15 mL) was cooled to 0° C. A 1M LiHMDS solution in THF (7.6 mL) was added slowly under argon to give a red/brown solution. The ice bath was immediately removed and the reaction allowed to stir at room temperature for 30 minutes. This solution was then transferred into a flask containing iodomethane (15 mL, 241 mmol) under an argon atmosphere. The reaction was monitored by TLC (20% ethyl acetate/hexane) and quenched with water after 1 hour at room temperature. The reaction was concentrated in vacuo and the residue partitioned between EtOAc (40 mL) and water (40 mL). The organic layer was collected, dried over $MgSO_4$, and concentrated in vacuo to give an orange/red oil (1.02 g). The crude mixture was purified by chromatography on silica gel (10% ethyl acetate/hexane) to give the desired product as a yellow/white solid (0.37 g). The impure fractions were collected and repurified by plate chromatography to give the desired product (0.59 g). [Total yield, 0.96 g]. $^1H$ NMR spectrum was consistent with proposed structure.

Step B

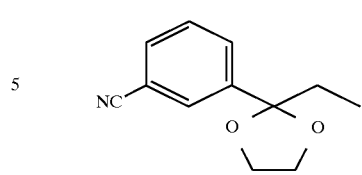

To the product of Step A (1.0 g, 6.3 mmol) in toluene (20 mL) was added ethylene glycol (0.78 g, 12.6 mmol). The reaction was heated to reflux overnight. The reaction solution was diluted with water and extracted with ethyl acetate. The organic layer was washed with brine, dried oved $MgSO_4$ and concentrated in vacuo to give the desired product (1.24 g). $^1H$ NMR was consistent with the proposed structure.

Step C

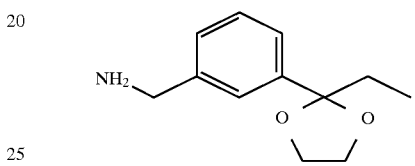

The product of Step B was dissolved in a EtOH and hydrogenated with W-2 Raney Ni in a Parr Shaker (60 psi, 25° C.) for 8 hours. The catalyst was filtered off and the purple filtrate concentrated in vacuo to give of desired product (1.18 g). $^1H$ NMR spectrum was consistent with proposed structure.

Step D

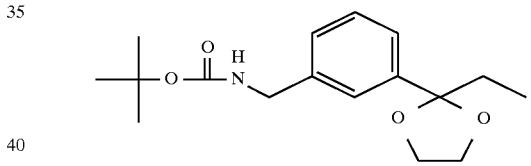

A mixture of the product of Step C (278 mg, 1.3 mmol), di-tert-butyl dicarbonate (0.3 g, 1.3 mmol) and triethylamine (0.27 g, 2.7 mmol) in dioxane/$H_2O$ (80:20, 10 mL) was stirred at room temperature overnight. The reaction mixture was concentrated in vacuo and the residue was dissolved in ethyl acetate. The solution was treated with water and extracted with ethyl ether. The combined organic layers was washed with brine, dried over $MgSO_4$ and evaporated to afford the desired product (0.44 g). $^1H$ NMR spectrum was consistent with proposed structure.

Step E

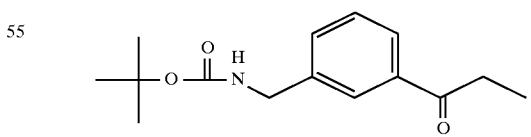

A mixture of the product of Step D (0.44 g, 1.4 mmol) and 1M HCl solution (2.9 mL) in THF (5 mL) was stirred at room temperature for 48 hours. The reaction mixture was diluted with ethyl acetate and washed with brine. The organic layer was dried over $MgSO_4$ and concentrated in vacuo to give the desired product (0.34 g). $^1H$ NMR spectrum was consistent with proposed structure.

Step F

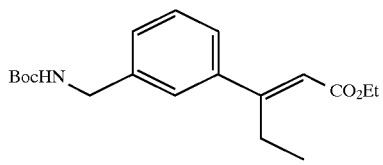

The above compound was prepared as in Example 58, Step A starting from the product of Step E. $^1$H NMR was consistent with the proposed structure.

Step G

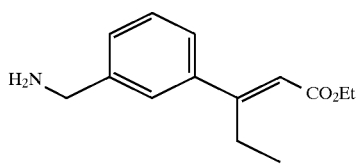

The above compound was prepared as in Example 75, Step A starting from the product of Step F. $^1$H NMR was consistent with the proposed structure.

Step H

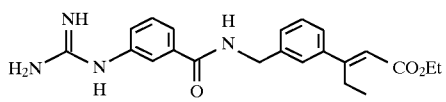

The above compound was prepared as in Example 28, Step C starting from the product of Step G. $^1$H NMR was consistent with the proposed structure.

Step I

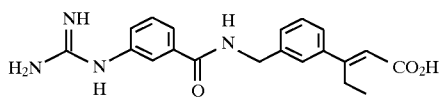

The above compound was prepared as in Example 21, Step C starting from the product of Step H.

Anal. calcd for $C_{20}H_{22}N_4O_3+1.7$ TFA+1.0 $H_2O$: C, 48.60; H, 4.48; N, 9.69. Found: C, 48.78; H, 4.16; N, 9.67.

EXAMPLE 75

3-[3-[[[[3-[(aminoiminomethyl)amino]phenyl]carbonyl]amino]methyl]phenyl]-3-(3,5-dichlorophenyl) propenoic acid, trifluoroacetate salt

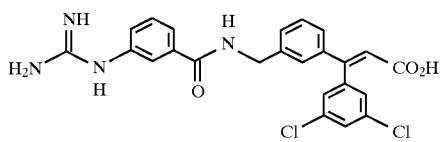

Step A

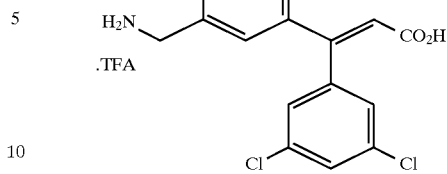

To a solution of the compound of Example C (0.272 g, 0.6 mmol) in $CH_2Cl_2$ (5 mL) was added TFA (1 mL) at 0° C. The ice bath was removed after the addition and the reaction was stirred at room temperature for 4 hours. The reaction solution was concentrated in vacuo to give a brown oil. $^1$H NMR spectrum was consistent with proposed structure.

Step B

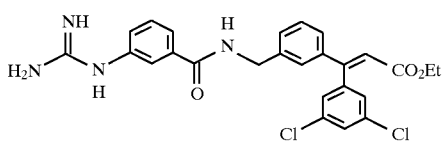

The above compound was prepared in the same manner as described in Example 1, Step D starting from the compound of Step A. $^1$H NMR was consistent with the proposed structure.

Step C

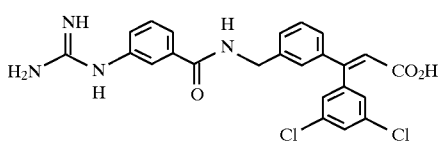

The above compound was prepared as in Example 2, starting with the product of Step B.

Anal. calcd for $C_{24}H_{20}N_4O_3Cl_2+1.1$ TFA+0.6 $H_2O$; C, 50.79; H, 3.63; N, 9.04. Found: C, 50.56; H, 3.30; N, 9.05.

EXAMPLE 76

3-[2,3-dihydro-1-[[3-[(1,4,5,6-tetrahydropyrimidin-2-yl)amino]phenyl]carbonyl]-1H-indol-5-yl] propenoic acid, trifluoroacetate salt

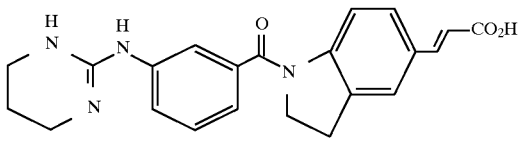

Step A

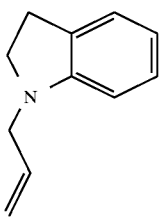

To a solution of indoline (5.0 g, 41 mmol) in ethanol (20 mL) was added K$_2$CO$_3$ (5.7 g, 41 mmol) followed by allyl bromide (3.5 ml, 41 mmol) and the reaction was allowed to stir at 60° C. for 16 hours. The reaction was cooled, suctioned filtered, and concentrated in vacuo. The crude oil was chromatographed on a 4000 μm chromatotron plate (9:1 hexane:ethyl acetate) to afford the desired product (4.7 g). $^1$H NMR was consistent with the proposed structure.

Step B

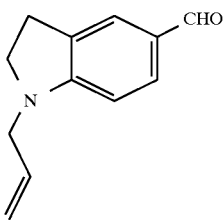

To a solution of the product of Step A (4.7 g, 29.5 mmol) in DMF (20 mL) was added dropwise at 0° C. POCl$_3$ (2.75 mL, 29.5 mmol). The reaction mixture was allowed to stir at room temperature for 16 hours. Water (10 mL) was then added and the resulting reaction mixture was stirred for another hour. The crude product was extracted with ether, the organic layer dried with magnesium sulfate and chromatographed on a 4000 m chromatotron plate (85:15 hexane:ethyl acetate) to afford the desired product (5.1 g). $^1$H NMR was consistent with the proposed structure.

Step C

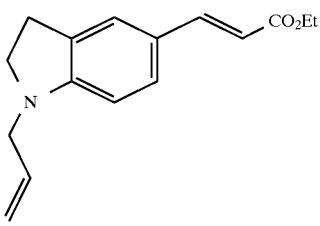

To a suspension of a 60% dispersion of NaH (1.6 g, 40.8 mmol) in THF (50 mL) was added dropwise at 0° C. triethylphosphonate (5.4 mL, 27.2 mmol). After five minutes, the product from Step B was added to the reaction mixture. The reaction was allowed to warm to room temperature and stirred for 16 hours. Water (100 mL) was added and the product was extracted with ethyl acetate (100 mL). The crude product was chromatographed on a 4000 μm chromatotron plate (9:1 hexane:ethyl acetate) to afford the desired product (5.1 g). $^1$H NMR was consistent with the proposed structure.

Step D

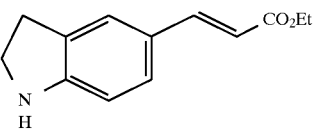

The product of Step C (5.0 g, 19.4 mmol) was dissolved in methylene chloride (30 mL) in a flame dried round bottom flask under argon. To this solution was added N,N'-dimethylbarbituric acid (9.1 g, 58.3 mmol) and tetrakis (triphenylphosphine) palladium (0.224 g, 0.194 mmol). The reaction was stirred at 35° C. for 2 hours at which time a precipitate was evident. The methylene chloride was evaporated in vacuo and replaced with ether (50 mL). The organic layer was then washed with two saturated sodium carbonate washes (25 mL each), dried over magnesium sulfate, suctioned filtered, and concentrated. The crude product was chromatographed on a 4000 μm chromatotron plate (9:1 hexane:ethyl acetate) to afford the desired product (6.2 g). $^1$H NMR was consistent with the proposed structure.

Step E

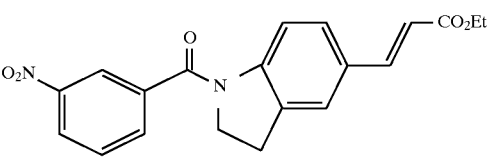

The above compound was prepared as in Example 5, Step B starting from the product of Step D. $^1$H NMR was consistent with the proposed structure.

Step F

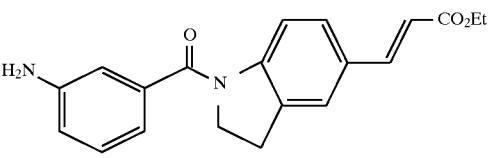

The above compound was prepared as in Example 5, Step C starting from the product of Step E. $^1$H NMR was consistent with the proposed structure.

Step G

The above compound was prepared as in Example 18, Step A starting from the product of Step F. $^1$H NMR was consistent with the proposed structure.

Step H

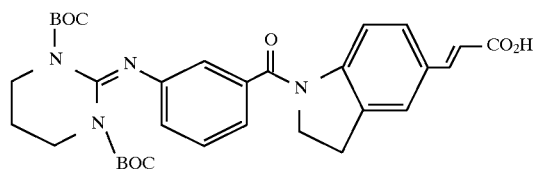

The above compound was prepared as in Example 21, Step C starting from the product of Step G. ¹H NMR was consistent with the proposed structure.

Step I

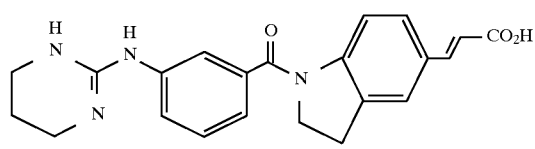

The above compound was prepared as in Example 5, Step E starting from the product of Step H.

Anal. calcd for $C_{22}H_{22}N_4O_3$ +1.2 TFA: C, 55.58; H, 4.43; N, 10.63. Found: C, 55.54; H, 4.12; N, 10.52.

EXAMPLE 77

3-[1-[[3-[(4,5-dihydro-1H-imidazol-2-yl)amino]phenyl]carbonyl]2,3-dihydro-1H-indol-5-yl]propenoic acid, trifluoroacetate salt

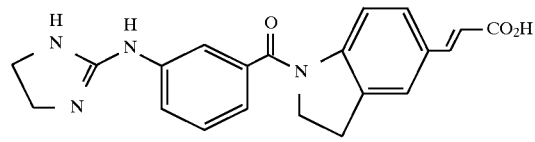

The above compound was prepared as in Example 21, Steps A–C starting from the product of Example 76, Step F.

Anal. calcd for $C_{21}H_{20}N_4O_3$+1.25 TFA: C, 54.39; H, 4.13; N, 10.80. Found: C, 54,24; H, 4.13; N, 10.94.

EXAMPLE 78

3-[1-[[3-[(1,4,5,6-tetrahydropyrimidin-2-yl)amino]phenyl]carbonyl]-1,2,3,4-tetrahydro-quinolin-6-yl]propenoic acid, trifluoroacetate salt

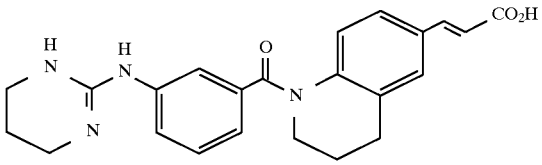

The above compound was prepared as in Example 76, Steps A–I starting from 1,2,3,4-tetrahydroquinoline.

Anal. calcd for $C_{23}H_{24}N_4O_3$+1.0 TFA+2.0 $H_2O$: C, 43.77; H, 3.73; N, 7.24. Found: C, 43.85; H, 3.46; N, 7.52.

EXAMPLE 79

3-[3-[2-[3-[(aminoimino)methyl]amino]phenyl]-2-oxoethoxy]phenyl]propenoic acid, trifluoroacetate salt

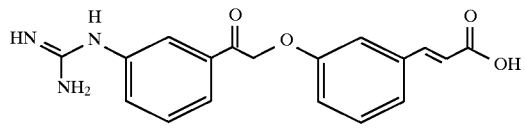

Step A

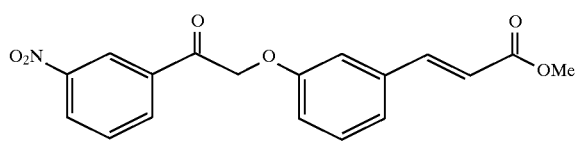

A mixture of methyl 3-hydroxycinnamate (10.7 g, 59.9 mmol), 2-bromo-3'-nitroacetophenone (16 g, 65.9 mmol), potassium carbonate (9.1 g, 65.9 mmol) in acetone (300 ml) was refluxed for 30 hours. The reaction mixture was cooled, filtered and washed with acetone. The combined organic fractions were concentrated in vacuo to remove acetone and the crude residue purified using silica gel chromatography (9:1 toluene:ethyl acetate) to give the desired product (9.72 g), as a yellow solid. ¹H NMR was consistent with the proposed structure.

Step B

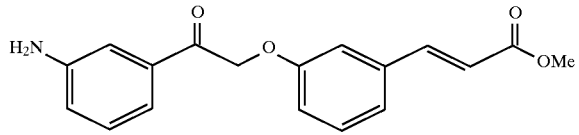

To a suspension of the product of Step A (1.0 g, 3.1 mmol) in ethanol (25 ml), $SnCl_2.2H_2O$ (2.1 g, 9.3 mmol) was added and the mixture refluxed for 4 hours. Additional $SnCl_2.2H_2O$ (0.5 g) was added and the mixture continued to reflux. After 1 hour, the reaction was cooled and the solvent removed under reduced pressure. The mixture was resuspended in ethyl acetate and washed with aqueous potassium carbonate. The organic fractions were dried ($Na_2SO_4$), filtered and concentrated. The crude mixture (0.85 g) was purified by chromatography on silica gel (1:1 hexane:ethyl acetate) to give the desired product (0.53 g). ¹H NMR was consistent with the proposed structure.

Steps C–D

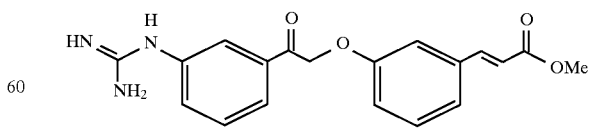

The above compound was prepared as in Example 5, Steps D–E starting from the product of Step B to give the desired product. ¹H NMR was consistent with the proposed structure.

Step E

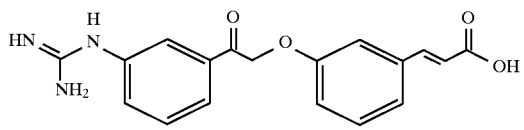

The above compound was prepared as in Example 21, Step C starting from the product of Step D to afford the desired product.

Anal. calcd for $C_{18}H_{17}N_3O_4+1.5$ TFA+0.5 $H_2O$: C, 48.52; H, 3.75; N, 8.08. Found: C, 48.33; H, 3.67; N, 7.77.

EXAMPLE 80

3-[3-[2-[3-[(4,5-dihydro-1H-imidazol-2-yl)amino]phenyl]-2-oxoethoxy]phenyl]propenoic acid, trifluoroacetate salt

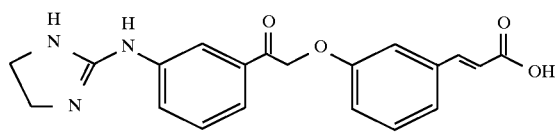

The above compound was prepared as in Example 21, Steps A–C starting from the product of Example 79, Step B.

Anal. calcd for $C_{20}H_{19}N_3O_4+1.25$ TFA: C, 53.21; H, 4.02; N, 8.27. Found: C, 52.86; H, 3.71; N, 8.45.

EXAMPLE 81

3-[3-[[2-[3-[(aminoiminomethyl)amino]phenyl]-2-hydroxyethyl]amino]phenyl]propenoic acid, (bis) trifluoroacetate salt hydrate

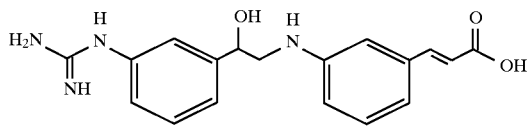

Step A

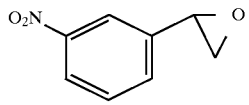

To a solution of 3-nitrostyrene (7.8 g, 52.5 mmol) in chloroform (75 mL) was added MCPBA (13.7 g, 79.4 mmol). The reaction was stirred at room temperature for 60 hours. The reaction mixture was diluted with methylene chloride and washed with a saturated sodium bicarbonate solution. The organic solution was dried and concentrated in vacuo. The residue was purified by chromatography on silica (7:3 hexane:ethyl acetate) to give the desired product (4.15 g). $^1$H NMR was consistent with the proposed structure.

Step B

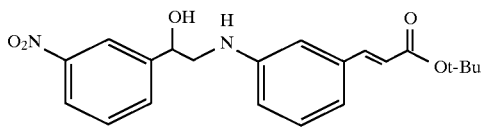

To the product from Step A (4.15 g, 25.1 mmol) and t-butyl 3-aminocinnamate (5.51 g, 25.1 mmol) in acetonitrile (100 mL) was added cobalt (II) chloride (1.14 g, 8.78 mmol). The reaction mixture was heated at reflux for 48 hours. The mixture was cooled, diluted with ethyl acetate and washed with water. The organic solution was dried and concentrated in vacuo. The residue was purified by chromatography on silica gel (7:3 hexane:ethyl acetate) to give the desired product (6.73 g). $^1$H NMR was consistent with the proposed structure.

Steps C–E

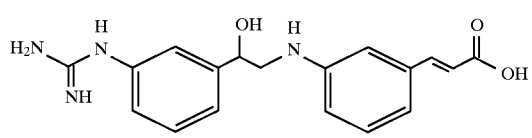

The above compound was prepared as in Example 5, Steps C–E starting from the product of Step B to give the desired product.

Anal. calcd for $C_{18}H_{20}N_4O_3+2.9$ TFA+2.0 $H_2O$: C, 40.43; H, 3.83; N, 7.92. Found: C, 40.69; H, 3.49; N, 8.23.

EXAMPLE 82 ethyl 3-[3-[2-[3-[(4,5-dihydro-1H-imidazol-2-yl)amino]phenoxy]acetyl]phenyl]propenoate, trifluoroacetate salt

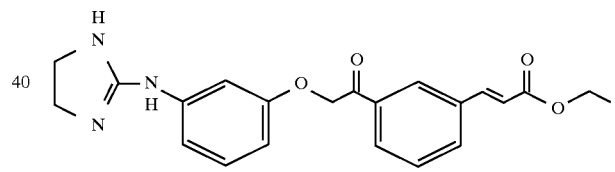

Step A

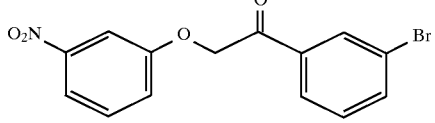

The above compound was prepared as in Example 79, Step A starting from 3-nitrophenol and 2-bromo-3'-bromoacetophenone. $^1$H NMR was consistent with the proposed structure.

Step B

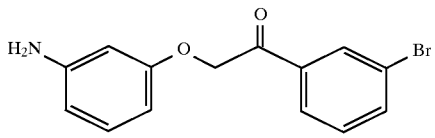

The product from Step A (5.4 g, 16.0 mmol) in ethyl acetate was hydrogenated at atmospheric pressure with 3%

Pt/C catalyst for 2 hours. The catalyst was removed by filtration and the filtrate was concentrated in vacuo to give the desired product (4.9 g). ¹H NMR was consistent with the proposed structure.

Step C

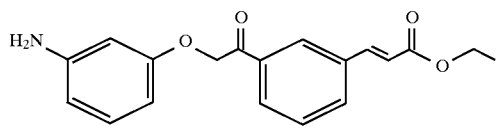

The above compound was prepared as in Example 5, Step A starting from the product of Step B and ethyl acrylate. ¹H NMR was consistent with the proposed structure.

Steps D–E

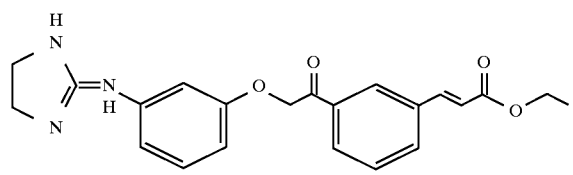

The above compound was prepared as in Example 21, Steps A–B starting from the product of Step C.

Anal. calcd for $C_{22}H_{23}N_3O_4$+1.0 TFA: C, 56.80; H, 4.77; N, 8.28. Found: C, 56.53; H, 4.64; N, 8.09.

EXAMPLE 83

3-[3-[2-[3-[(4,5-dihydro-1H-imidazol-2-yl)amino]phenoxy]acetyl]phenyl]propenoic acid, trifluoroacetate salt

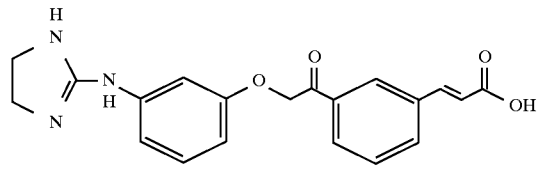

The above compound was prepared as in Example 21, Step C starting from the product of Example 82, Step D.

Anal. calcd for $C_{20}H_{19}N_3O_4$+1.1 TFA: C, 54.33; H, 4.13; N, 8.56. Found: C, 54.05; H, 4.37; N, 8.32.

EXAMPLE 84

3-[5-[3-[3-[(aminoiminomethyl)amino]phenyl]-1-oxopropenyl]-2-fluorophenyl]propenoic acid, trifluoroacetate salt

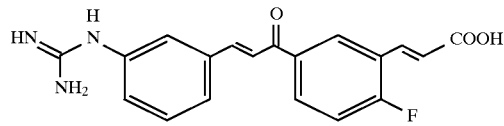

Step A

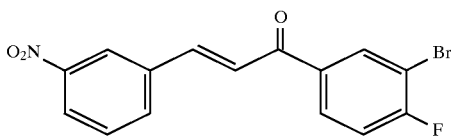

To a solution of 3-bromo-4-fluoroacetophenone (20.0 g, 92.2 mmoles) and 3-nitrobenzaldehyde (13.9 g, 92.2 mmoles) in absolute ethanol (92 mL) was added slowly a solution of potassium hydroxide (1.18 g, 21.1 mmoles) in absolute ethanol (8 mL), forming a thick paste. The mixture was diluted with ethanol (100 mL), and then stirred overnight in a stoppered flask. The solid was filtered, washed with ethanol, and then air dried to give the above compound (30.3 g), as a pale yellow solid. ¹H NMR was consistent with the proposed structure.

Step B

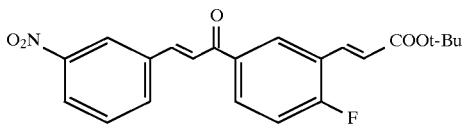

The above compound was prepared as in Example 5, Step A starting with the product of Step A. ¹H NMR was consistent with the proposed structure.

Steps C–E

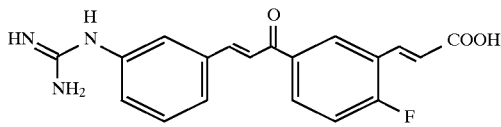

The above compound was prepared as in Example 5, Steps C–E starting using the product of Step B.

Anal. calcd. for $C_{19}H_{16}FN_3O_3$+1.0 TFA+0.25 toluene: C, 55.72; H, 3.91; N, 8.57. Found: C, 55.94; H, 4.12; N, 8.23.

EXAMPLE 85

3-[5-[3-[3-[(1,4,5,6-tetrahydrolpyrimidin-2-yl)]phenyl]-1-oxopropenyl]-2-fluorophenyl]propenoic acid, trifluoroacetate salt

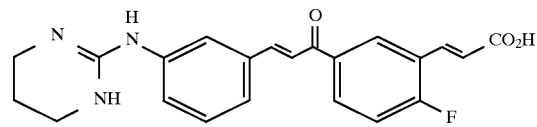

The above compound was prepared as in Example 18, Steps A–B starting from the product of Example 84, Step C.

Anal. calcd. for $C_{19}H_{16}FN_3O_3$+1.0 TFA +0.25 $H_2O$; C, 55.72; H, 3.91; N, 8.57. Found: C, 55.94; H, 4.12; N, 8.23.

EXAMPLE 86

3-[3-[3-[3-[(aminoiminomethyl)amino]phenyl]-1-oxopropenyl]-4-methoxyphenyl]propenoic acid, trifluoroacetate salt

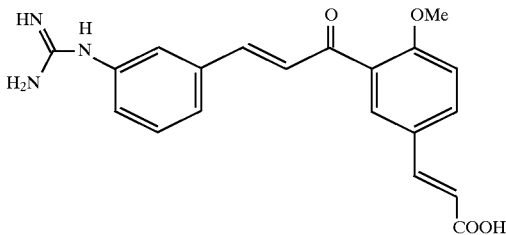

The above compound was prepared as in Example 84, Steps A–E starting from 5-bromo-2-methoxyacetophenone and 3-nitrobenzaldehyde.

Anal. calcd for $C_{20}H_{19}N_3O_4$+1.0 TFA+0.75 $H_2O$: C, 53.61; H, 4.09; N, 8.52. Found: C, 53.60; H, 4.12; N, 8.47.

EXAMPLE 87

3-[3-[3-[3-[(4,5-dihydro-1H-imidazol-2-yl)amino]phenyl]-1-oxopropenyl]-4-methoxyphenyl]propenoic acid, trifluoroacetate salt

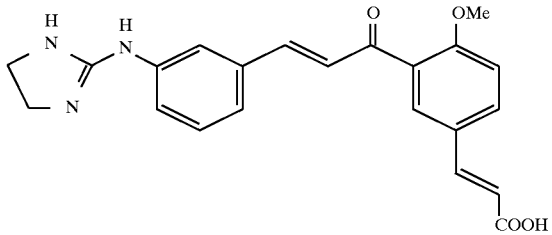

The above compound was prepared as in Example 21, Steps A–B starting from the product of Example 86, Step C.

Anal. calcd for $C_{22}H_{21}N_3O_4$+1.0 TFA+0.5 $H_2O$: C, 56.03; H, 4.31; N, 8.17. Found: C, 55.76; H, 4.48; N, 8.33.

EXAMPLE 88

3-[3-[3-[3-[(aminoiminomethyl)amino]phenyl]-1-oxopropenyl]phenyl]propenoic acid, trifluoroacetate salt

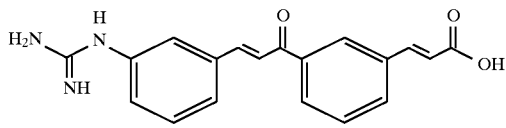

The above compound was prepared as in Example 84, Steps A–E starting from 3-bromoacetophenone and 3-nitrobenzaldehyde.

Anal. calcd for $C_{19}H_{17}N_3O_3F$+1.5 TFA: C, 52.18; H, 3.68; N, 8.30. Found: C, 52.30; H, 3.70; N, 8.68.

EXAMPLE 89

3-[3-[3-[3-[(aminoiminomethyl)amino]phenyl]-3-oxopropenyl]phenyl]propenoic acid, trifluoroacetate salt hydrate

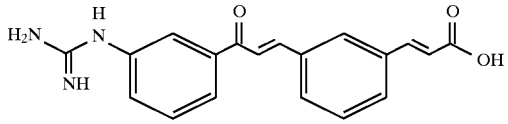

The above compound was prepared as in Example 84, Steps A–E starting from 3-nitroacetophenone and 3-bromobenzaldehyde.

Anal. calcd for $C_{19}H_{17}N_3O_3$+1.0 TFA+1.0 $H_2O$: C, 53.96; H, 4.31; N, 8.99. Found: C, 54.28; H, 4.39; N, 8.96.

EXAMPLE 90

3-[3-[1-oxo-3-[3-[(1,4,5,6-tetrahydropyrimidin-2-yl)amino]phenyl]-2-propenyl]phenyl]propenoic acid, trifluoroacetate salt

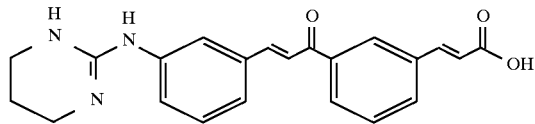

The above compound was prepared as in Example 18, Steps A–B starting from the product of Example 88, Step C.

Anal. calcd for $C_{22}H_{21}N_3O_3$+1.5 TFA: C, 54.95; H, 4.15; N, 7.69. Found: C, 55.25; H, 4.45; N, 7.87.

EXAMPLE 91

3-[3-[3-[3-[(aminoiminomethyl)amino]phenyl]-3-oxopropyl]phenyl]propenoic acid, trifluoroacetate salt hydrate

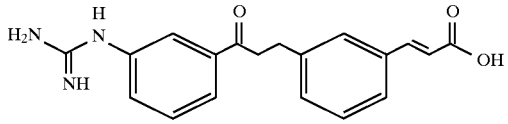

Step A

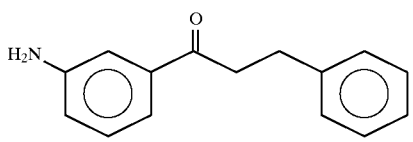

A mixture of the product from Example 89, Step A (2.0 g, 6.0 mmol) and catalytic amount of platinum (IV) oxide in ethyl acetate was hydrogenated under 60 psi at 40° C. for 1.2 hours. After filtration through Celite, the filtrate was concentrated and purified by chromatography on silica gel (ethyl acetate/hexane, 4:6) to give the desired product (1.0 g).

Anal. calcd for $C_{15}H_{14}BrNO$: C, 59.23; H, 4.64; N, 4.60. Found: C, 59.15; H, 4.78; N, 4.71.

Steps B–D

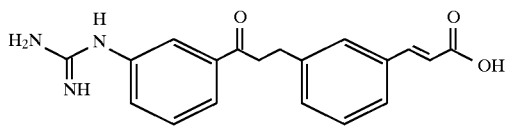

The above compound was prepared as in Example 5, Steps A, D–E starting with the product of Step A.

Anal. calcd for $C_{19}H_{19}N_3O_3+1.0\,TFA+1.0\,H_2O$: C, 53.73; H, 4.72; N, 8.95. Found: C, 53.65; H, 4.89; N, 8.79.

EXAMPLE 92

3-[3-[3-[3-[(aminoiminomethyl)amino]phenyl]-1-oxopropyl]phenyl]propenoic acid, trifluoroacetate salt

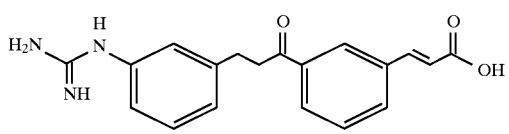

The above compound was prepared as in Example 91, Steps A–E, starting from the product of Example 88, Step A.

Anal. calcd for $C_{19}H_{19}N_3O_3+1.0\,TFA+0.75\,H_2O$: C, 54.25; H, 4.66; N, 9.04. Found: C, 54.21; H, 4.31; N, 9.08.

EXAMPLE 93

3-[3-[1-oxo-3-[3-[(1,4,5,6-tetrahydropyrimidin-2-yl)amino]phenyl]propyl]phenyl]propenoic acid, trifluoroacetate salt

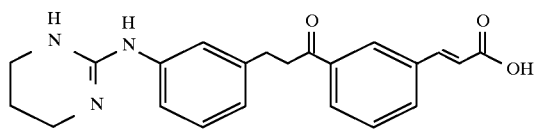

The above compound was prepared as in Example 18, Steps A–B, starting from the product of Example 92, Step C.

Anal. calcd for $C_{22}H_{23}N_3O_3+1.0\,TFA+0.5\,H_2O$: C, 57.60; H, 5.04; N, 8.40. Found: C, 57.40; H, 4.92; N, 8.83.

EXAMPLE 94

3-[3-[3-oxo-3-[3-[(1,4,5,6-tetrahydropyrimidin-2-yl)amino]phenyl]-1-propenyl]phenyl]propenoic acid, trifluoroacetate salt

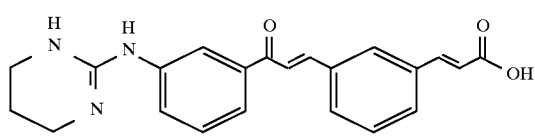

The above compound was prepared as in Example 18, Steps A–B, starting from the product of Example 89, Step C.

Anal. calcd for $C_{22}H_{23}N_3O_3+1.5\,TFA$: C, 54.95; H, 4.15; N, 7.69. Found: C, 55.40; H, 4.08; N, 7.30.

EXAMPLE 95

3-[3-[3-oxo-3-[3-[(1,4,5,6-tetrahydropyrimidin-2-yl)amino]phenyl]propyl]phenyl]propenoic acid, trifluoroacetate salt hydrate

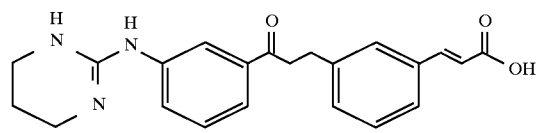

The above compound was prepared as in Example 18, Steps A–B, starting from the product of Example 91, Step C.

Anal. calcd for $C_{22}H_{23}N_3O_3+1.0\,TFA+1.0\,H_2O$: C, 56.58; H, 5.14; N, 8.25. Found: C, 56.07; H, 4.93; N, 8.31.

EXAMPLE 96

3-[3-[3-[3-[(aminoiminomethyl)amino]phenyl]-3-hydroxypropyl]phenyl]propenoic acid, trifluoroacetate salt

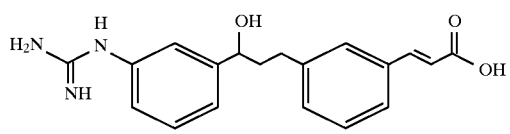

Step A

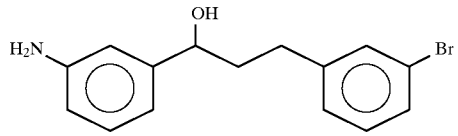

To a slurry of lithium aluminum hydride (0.40 g, 0.011 mol) in ether (20 mL) at 0° C. was added a solution of the product from Example 91, Step A (3.0 g, 0.01 mol) in ether (20 mL). The reaction mixture was stirred at room temperature for 3 hours and then quenched by adding water (0.5 mL), followed by 10% NaOH solution (1.0 mL). The resulting slurry was filtered through Celite and washed with THF (2×50 mL). The combined organic layer was dried over $MgSO_4$ and filtered. The filtrate was concentrated under vacuum and the crude product was purified by chromatography on silica gel (1:1 hexane:ethyl acetate) to give the desired product (2.68 g).

Anal. calcd for $C_{15}H_{16}BrNO$: C, 58.84; H, 5.27; N, 4.57. Found: C, 59.19; H, 5.64; N, 4.65.

Steps B–D

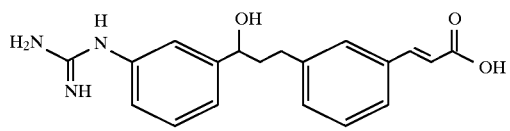

The above compound was prepared as in Example 91, Steps B–D, starting from the product of Step A.

Anal. calcd for $C_{19}H_{21}N_3O_3+1.5\,TFA$: C, 51.77; H, 4.44; N, 8.23. Found: C, 51.53; H, 4.91; N, 8.49.

EXAMPLE 97

3-[4-[2-[3-[(aminoiminomethyl)amino]phenyl]ethenyl)phenyl)propenoic acid, trifluoroacetate salt

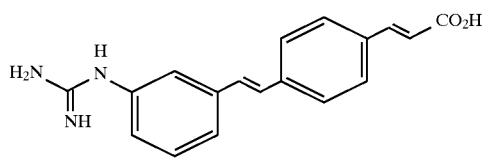

Step A

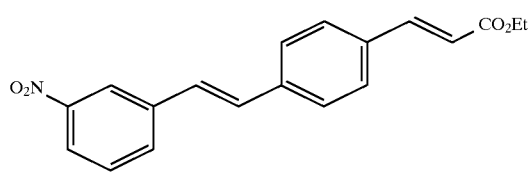

Ethyl trans-4-bromocinnamate (2.55 g, 10 mmol) and 3-nitro styrene (1.84 g, 12.3 mmol) in triethylamine (5 mL) was purged for 5 minutes with argon before adding tri-o-tolylphosphine (0.062 g, 0.2 mmol) and palladium acetate (0.022 g, 0.1 mmol). The resulting solution was purged with argon for 2 minutes and sealed. The reaction vessel was heated to 85°–90° C. for 16 hours. The reaction was diluted with $CHCl_3$ and washed with 10% HCl and brine. The organic layer was dried over NaOH and concentrated in vacuo to give a yellow solid (2.2 g). $^1$H NMR was consistent with the proposed structure.

Steps B–D

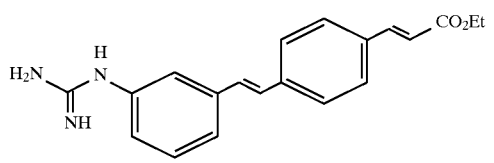

The above compound was prepared as in Example 5, Steps C–E, starting from the product of Step A. $^1$H NMR was consistent with the proposed structure.

Step E

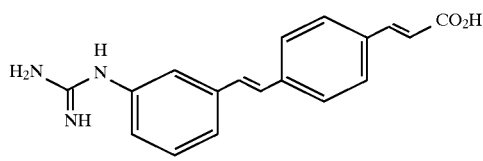

The above compound was prepared as in Example 21, Step C, starting from the product of Step D.

Anal. calcd for $C_{18}H_{17}N_3O_2$+1.1 TFA: C, 56.06; H, 4.22; N, 9.71. Found: C, 55.97; H, 4.02; N, 9.77.

EXAMPLE 98

3-[4-[2-[3-[(1,4,5,6-tetrahydropyrimidin-2-yl)amino]phenyl]ethenyl]phenyl]propenoic acid, trifluoroacetate salt

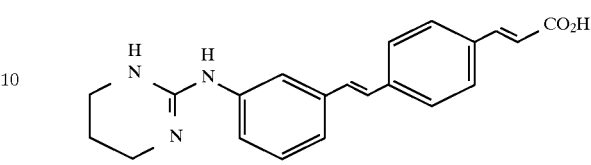

Steps A–B

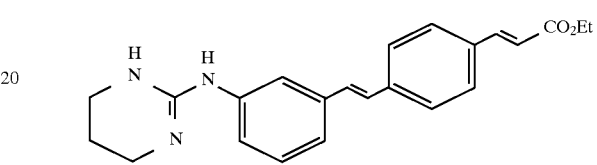

The above compound was prepared as in Example 18, Steps A–B, starting from the product of Example 97, Step B. $^1$H NMR was consistent with the proposed structure.

Step C

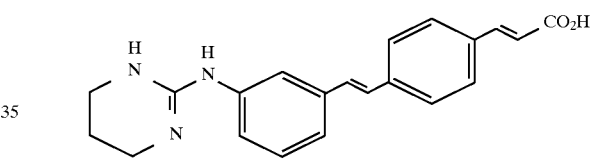

The above compound was prepared as in Example 21, Step C, starting from the product of Steps A–B.

Anal. calcd for $C_{21}H_{21}N_3O_2$+1.2 TFA: C, 58.04; H, 4.62; N, 8.68. Found: C, 58.33; H, 4.79; N, 8.78.

EXAMPLE 99

3-[4-[2-[3-[(4,5-dihydro-1H-imidazol-2-yl)amino]phenyl]ethenyl]phenyl]propenoic acid, trifluoroacetate salt Steps A–C

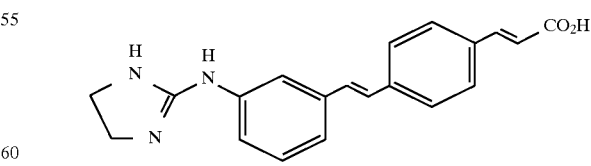

The above compound was prepared as in Example 21, Steps A–C, starting from the product of Example 97, Step B.

Anal. calcd for $C_{20}H_{19}N_3O_2$+0.9 TFA: C, 60.05; H, 4.60; N, 9.64. Found: C, 60.35; H, 4.63; N, 9.79.

EXAMPLE 100

3-[4-[2-[3-[(5,6-dihydro-4H-thiazin-2-yl)amino]phenyl]ethenyl]phenyl]propenoic acid, trifluoroacetate salt

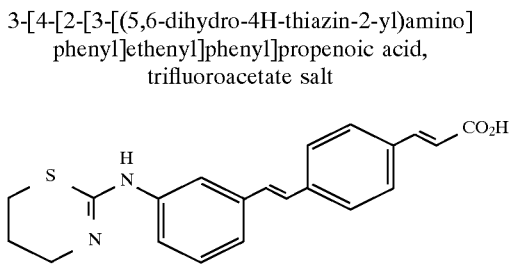

Step A

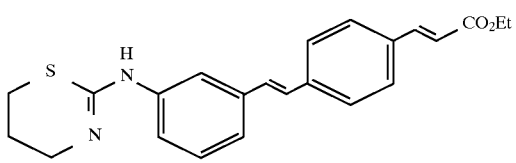

To a stirred solution of the compound from Example 97, Step B (0.8 g, 2.73 mmol) in acetonitrile (10 mL) was added acetic acid (177 mg, 2.9 mmol) and catalytic DMAP followed by 2-methylthio-5,6-dihydro-4H-1,3-thiazine (0.8 g, 2.9 mmol). The reaction mixture was heated to reflux for 5 hours. The reaction was concentrated in vacuo and the residue purified by reverse phase HPLC (water/TFA:acetonitrile) to give the desired compound (350 mg). $^1$H NMR was consistent with the proposed structure.

Step B

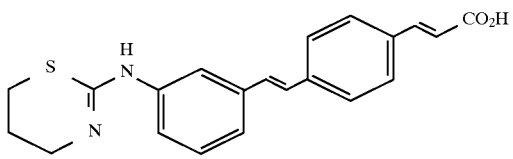

The above compound was prepared as in Example 21, Step C starting from the product of Step A.

Anal. calcd for $C_{21}H_{20}N_4O_2S+1.1$ TFA: C, 56.88; H, 4.34; N, 5.72. Found: C, 56.64; H, 4.28; N, 5.72.

EXAMPLE 101

3-[4-[[3-[(1,4,5,6-tetrahydropyrimidin-2-yl)amino]phenyl]methoxy]phenyl]propenoic acid, trifluoroacetate salt

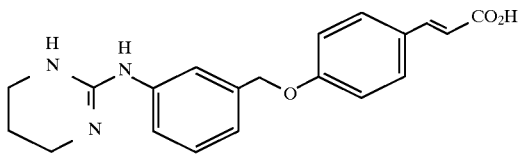

Step A

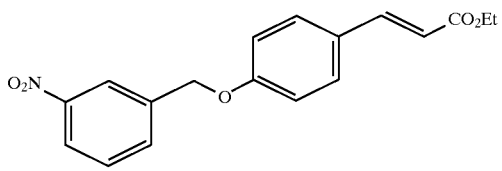

To a solution of 3-nitrobenzylbromide (2.52 g, 11.7 mmol) and potassium carbonate (5.66 g, 40.95 mmol) in DMF (100 mL) was added ethyl 4-hydroxycinnamate (2.24 g, 11.7 mmol), and the reaction mixture was stirred at room temperature under nitrogen for 2 hours. The reaction mixture was diluted with ethyl acetate and filtered. The filtrate was washed with water and brine, dried over $MgSO_4$ and concentrated in vacuo to yield the desired product (3.2 g). $^1$H NMR was consistent with the proposed structure.

Steps B–E

The title compound was prepared as in Example 76, Steps F–I starting from the product of Step A.

Anal. calcd for $C_{20}H_{21}N_3O_3+1.1$ TFA: C, 55.92; H, 4.67; N, 8.81. Found: C, 56.19; H, 4.55; N, 8.93.

EXAMPLE 102

3-[3-[2-[3-[(aminoiminomethyl)amino]phenyl]oxazol-4-yl]phenyl]propenoic acid, trifluoroacetate salt

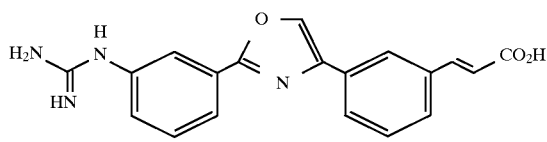

Step A

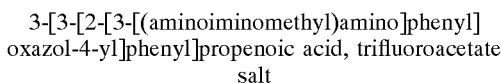

A mixture of 3-nitrobenzamide (8.51 g, 51.2 mmol) and 3-bromophenacyl bromide (8.16 g, 29.4 mmol) was heated at 140° C. for 6 hours. The mixture was cooled and partitioned between ethyl acetate and water. The organic layer was washed with brine and concentrated in vacuo to give the desired product. $^1$H NMR was consistent with the proposed structure.

Step B

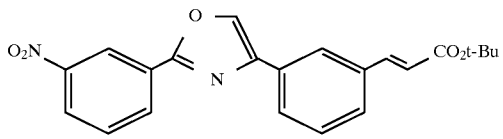

The product from Step A, (2.12 g, 6.1 mmol) in diisopropylamine (15 mL) in a heavy walled Pyrex tube was combined with tert-butyl acrylate (3.0 mL, 20.5 mmol), palladium acetate (83 mg, 0.37 mmol) and tri-o-tolylphosphine (281 mg, 0.92 mmol). The tube was purged with argon, sealed and placed in an oil bath at 120° C. for 48 hours. The mixture was cooled and concentrated in vacuo. The residue was purified by chromatography on silica gel (7:3 hexane: ethyl acetate). The product was isolated as a yellow solid. $^1$H NMR was consistent with the proposed structure.

Exact mass (M$^+$) calcd for $C_{22}H_{20}N_2O_5$: 392.1372. Found: 392.1364.

Steps C–E

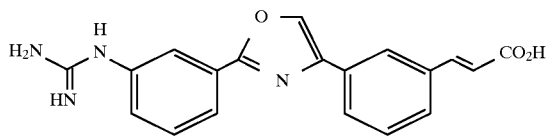

The above compound was prepared as in Example 5, Steps C–E starting from the product of Step B.

Anal. calcd for $C_{19}H_{16}N_4O_3$+1.5 TFA: C, 50.87; H, 3.40; N, 10.79. Found: C, 50.72; H, 3.46; N, 11.09.

EXAMPLE 103

3-[4-[4-[3-[(aminoiminomethyl)amino]phenyl]oxazol-2-yl]phenyl]propenoic acid

Steps A–E

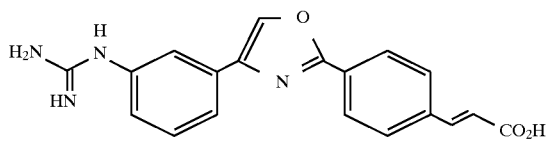

The above compound was prepared as in Example 102, Steps A–E, starting from 3-bromobenzamide and 3-nitrophenacyl bromide.

Anal. calcd for $C_{19}H_{16}N_4O_3$+1.25 TFA: C, 52.13; H, 3.61; N, 11.31. Found: C, 52.19; H, 3.45; N, 11.38.

EXAMPLE 104

3-[4-[2-[3-[(aminoiminomethyl)amino]phenyl]-1H-imidazol-5-yl]phenyl]propenoic acid, trifluoroacetate salt

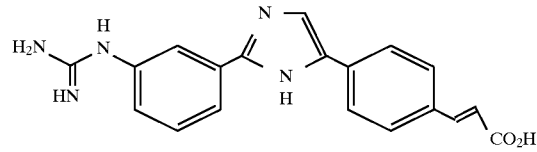

Step A

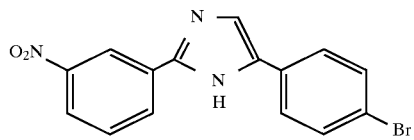

A solution of 3-nitrobenzamidine (2.11 g, 12.8 mmol) and 4-bromophenacyl bromide (2.44 g, 8.8 mmol) in chloroform (100 mL) was heated at reflux for 15 hours. The reaction mixture was cooled and the desired product collected by filtration. $^1$H NMR was consistent with the proposed structure.

Steps B–D

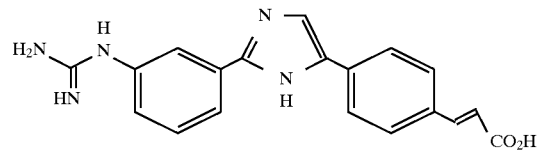

The above compound was prepared as in Example 5, Steps C–E starting from the product of Step A.

Anal calcd for $C_{19}H_{17}N_5O_2$+2.25 TFA+0.25 H$_2$O: C, 46.39; H, 3.27; N, 11.51. Found: C, 46.44; H, 3.47; N, 11.28.

The activity of the compounds of the present invention was tested in the following assays. The results of testing in the assays are tabulated in Table 1.

VITRONECTIN ADHESION ASSAY

Materials

Human vitronectin receptor ($\alpha_v\beta_3$) was purified from human placenta as previously described [Pytela et al., *Methods in Enzymology*, 144:475–489 (1987)]. Human vitronectin was purified from fresh frozen plasma as previously described [Yatohgo et al., *Cell Structure and Function*, 13:281–292 (1988)]. Biotinylated human vitronectin was prepared by coupling NHS-biotin from Pierce Chemical Company (Rockford, Ill.) to purified vitronectin as previously described [Charo et al., *J. Biol. Chem.*, 266(3):1415–1421 (1991)]. Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

Methods

Solid Phase Receptor Assays

This assay was essentially the same as previously reported [Niiya et al., *Blood*, 70:475–483 (1987)]. The purified human vitronectin receptor ($\alpha_v\beta_3$) was diluted from stock solutions to 1.0 g/mL in Tris-buffered saline containing 1.0 mM Ca$^{++}$, Mg$^{++}$, and Mn$^{++}$, pH 7.4 (TBS$^{+++}$). The diluted receptor was immediately transferred to Linbro microtiter plates at 100 μL/well (100 ng receptor/well). The plates were sealed and incubated overnight at 4° C. to allow the receptor to bind to the wells. All remaining steps were at room temperature. The assay plates were emptied and 200 μL, of 1% RIA grade BSA in TBS$^{+++}$(TBS$^{+++}$/BSA) were added to block exposed plastic surfaces. Following a 2 hour incubation, the assay plates were washed with TBS$^{+++}$ using a 96 well plate washer. Logarithmic serial dilution of the test compound and controls were made starting at a stock concentration of 2 mM and using 2 nM biotinylated vitronectin in TBS$^{+++}$/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was 1.0×10$^{-4}$M. The competition occurred for two hours after which all wells were washed with a plate washer as before. Affinity purified horseradish peroxidase labeled goat anti-biotin antibody was diluted 1:3000 in TBS$^{+++}$/BSA and 125 μL were added to each well. After 30 minutes, the plates were washed and incubated with OPD/H$_2$O$_2$ substrate in 100 mM/L Citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and % CV were determined for duplicate concentrations. The mean $A_{450}$ values were normalized to the mean of four maximum-binding controls (no competitor added) (B-MAX). The normalized values were subjected to a four parameter curve fit algorithm [Rodbard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Ser. No. 08/375,338, Example 1] which is a potent $\alpha_v\beta_3$ antagonist ($IC_{50}$ in the range 3–10 nM) was included on each plate as a positive control.

PURIFIED IIb/IIIa RECEPTOR ASSAY

Materials

Human fibrinogen receptor ($\alpha_{IIb}\beta_3$) was purified from outdated platelets. (Pytela, R., Pierschbacher, M. D., Argraves, S., Suzuki, S., and Rouslahti, E. "Arginine-Glycine-Aspartic acid adhesion receptors", *Methods in Enzymology* 144(1987):475–489.) Human vitronectin was purified from fresh frozen plasma as described in Yatohgo, T., Izumi, M., Kashiwagi, H., and Hayashi, M., "Novel purification of vitronectin from human plasma by heparin affinity chromatography," *Cell Structure and Function* 13(1988):281–292. Biotinylated human vitronectin was prepared by coupling NHS-biotin from Pierce Chemical Company (Rockford, Ill.) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", *J. Biol. Chem.* 266(3) (1991): 1415–1421.) Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

Methods
Solid Phase Receptor Assays

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", *Blood* 70 (1987):475–483. The purified human fibrinogen receptor ($\alpha_{IIb}\beta_3$) was diluted from stock solutions to 1.0 μg/mL in Tris-buffered saline containing 1.0 mM $Ca^{++}$, $Mg^{++}$, and $Mn^{++}$, pH 7.4 (TBS$^{+++}$). The diluted receptor was immediately transferred to Linbro microtiter plates at 100 μL/well (100 ng receptor/well). The plates were sealed and incubated overnight at 4° C. to allow the receptor to bind to the wells. All remaining steps were at room temperature. The assay plates were emptied and 200 μL of 1% RIA grade BSA in TBS$^{+++}$ (TBS$^{+++}$/BSA) were added to block exposed plastic surfaces. Following a 2 hour incubation, the assay plates were washed with TBS$^{+++}$ using a 96 well plate washer. Logarithmic serial dilution of the test compound and controls were made starting at a stock concentration of 2 mM and using 2 nM biotinylated vitronectin in TBS$^{+++}$/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was 1.0× $10^{-4}$M. The competition occurred for two hours after which all wells were washed with a plate washer as before. Affinity purified horseradish peroxidase labeled goat anti-biotin antibody was diluted 1:3000 in TBS$^{+++}$/BSA and 125 μL were added to each well. After 30 minutes, the plates were washed and incubated with ODD/$H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and % CV were determined for duplicate concentrations. The mean $A_{450}$ values were normalized to the mean of four maximum-binding controls (no competitor added) (B-MAX). The normalized values were subjected to a four parameter curve fit algorithm, [Robard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Ser. No. 08/375,338, Example 1] which is a potent $\alpha_v\beta_3$ antagonist ($IC_{50}$ in the range 3–10 nM) was included on each plate as a positive control.

TABLE I

| Example | AvB3 IC50 (nM) | IIb/IIIa IC50 (nM) |
|---|---|---|
| 1 | 15800 | >100000 |
| 2 | 13.0 | 657 |
| 3 | 29000 | 32200 |
| 4 | 10.6 | 7.05 |
| 5 | 4.01 | 9.58 |
| 7 | 2.95 | 15.1 |
| 9 | 3.46 | 11.0 |
| 11 | 7.07 | 14.1 |
| 12 | 155 | 670 |
| 13 | 23.1 | 2160 |
| 15 | 28.8 | 2620 |
| 16 | 50.9 | 25.4 |
| 17 | 10.3 | 37.9 |
| 18 | 0.46 | 181 |
| 19 | 0.53 | 439 |
| 21 | 0.49 | 125 |
| 22 | 0.48 | 234 |
| 23 | 0.31 | 80.3 |
| 24 | 4.93 | 8270 |
| 25 | 2.82 | 1830 |
| 27 | 204 | >100000 |
| 28 | 23.3 | 45.3 |
| 29 | 1830 | 25400 |
| 31 | 9.66 | 69.1 |
| 33 | 73.3 | 121 |
| 35 | 122 | 152 |
| 36 | 1.23 | 9.06 |
| 37 | 32.3 | 80.0 |

TABLE I-continued

| Example | AvB3 IC50 (nM) | IIb/IIIa IC50 (nM) |
|---|---|---|
| 40A | 0.45 | 97.2 |
| 40B | 5.71 | 817 |
| 40C | 176 | 20400 |
| 42 | 7.6 | 15.9 |
| 44 | 30.2 | 36.2 |
| 45 | 6.7 | 759 |
| 46 | 7.19 | 2600 |
| 49 | 2.18 | 661 |
| 50 | 0.43 | 772 |
| 51 | 3.86 | 641 |
| 52 | 72.5 | 133 |
| 53 | 7.89 | 232 |
| 54 | 12.5 | 686 |
| 55 | 3.62 | 432 |
| 56 | 4.03 | 656 |
| 57 | 25.8 | 12800 |
| 58 | 79.8 | 2270 |
| 59 | 1270 | 5140 |
| 60 | 67.3 | 440 |
| 62 | 2.04 | 23300 |
| 64 | 2180 | 16200 |
| 65 | 12.1 | 4950 |
| 67 | 2.27 | 12000 |
| 69 | 1.78 | 38900 |
| 71 | 1.33 | 18500 |
| 73 | 20400 | 66000 |
| 74 | 2690 | >100000 |
| 75 | 42700 | >100000 |
| 76 | 8.8 | 825 |
| 77 | 12.3 | 231 |
| 78 | 56.3 | 1790 |
| 79 | 12.0 | 415 |
| 80 | 1.02 | 3470 |
| 81 | 54.3 | 5020 |
| 83 | 21.7 | 10000 |
| 84 | 891 | 35200 |
| 85 | 92.0 | 20800 |
| 86 | 580 | 563 |
| 87 | 90.5 | 2640 |
| 88 | 37.3 | 2610 |
| 89 | 196 | 1260 |
| 90 | 6.98 | 2320 |
| 91 | 1270 | 8670 |
| 92 | 48.9 | 4010 |
| 93 | 6.1 | 5990 |
| 94 | 11.3 | 2710 |
| 95 | 58.5 | 11800 |
| 96 | 207 | 15600 |
| 98 | 5.08 | 222 |
| 99 | 26.5 | 722 |
| 100 | 30.6 | 664 |
| 101 | 42.6 | 118 |
| 102 | 1940 | 4480 |
| 103 | 32100 | 0.9 |
| 104 | 17300 | 24.5 |

What is claimed is:

1. A compound of the formula

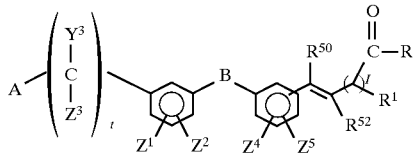

or a pharmaceutically acceptable salt thereof, wherein A is

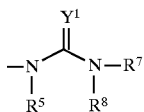

wherein $y^1$ is selected from the group consisting of $N-R^2$, O, and S;

$R^2$ is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy, carboxyl derivatives and phenyl;

or $R^2$ taken together with $R^7$ forms a 5 membered heteroaromatic ring;

or $R^2$ taken together with $R^7$ forms a 5 membered heteroaromatic ring fused with a phenyl group;

$R^7$ (when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; —SO$_2$R$^{10}$ wherein R$^{10}$ is selected from the group consisting of alkyl, aryl and monocyclic heterocycles, all optionally substituted with one or more substituent selected from the group consisting of halogen, naloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

wherein R$^{10}$ is defined above;
or NR$^7$ and R$^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;
R$^5$ is selected from the group consisting of H, alkyl, alkenyl, alkynyl, benzyl, and phenethyl; or
A is

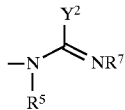

wherein y$^2$ is selected from the group consisting of alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; —S—R$^9$ and —O—R$^9$ wherein R$^9$ is selected from the group consisting of H; alkyl; aralkyl; aryl; alkenyl; and alkynyl; or R$^9$ taken together with R$^7$ forms a 4–12 membered mononitrogen containing sulfur or oxygen containing heterocyclic ring; and
R$^5$ and R$^7$ are as defined above;
or y$^2$ (when y$^2$ is carbon) taken together with R$^7$ forms a 4–12 membered mononitrogen containing ring optionally substituted with alkyl, aryl or hydroxy;
z$^1$, z$^2$, Z$^4$ and Z$^5$ are independently selected from the group consisting of H; alkyl; hydroxy; alkoxy; aryloxy; arylalkoxy; halogen; haloalkyl; haloalkoxy; nitro; amino; aminoalkyl; alkylamino; dialkylamino; cyano; alkylthio; alkylsulfonyl; carboxyl derivatives; carboxylalkenyl; alkoxycarbonylalkenyl; alkoxycarbonylamino; acetamide; aryl; fused aryl; cycloalkyl; thio; monocyclic heterocycles; fused monocyclic heterocycles; and A, wherein A is defined above;

B is selected from the group consisting of

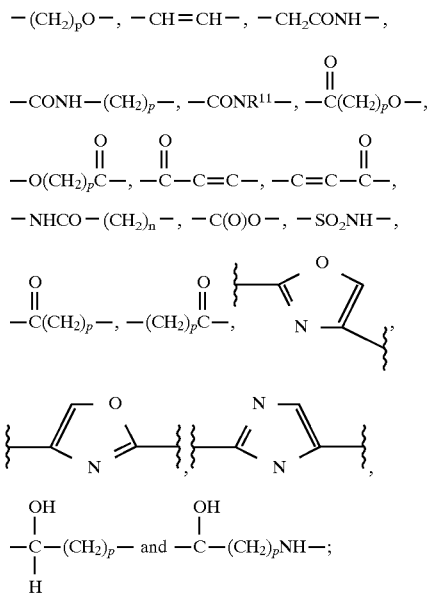

wherein p is an integer selected from the group consisting of 0, 1 and 2; wherein R$^{11}$ is selected from the group consisting of H, alkyl, alkenyl, alkynyl, benzyl and phenethyl; wherein n is an integer selected from the group consisting of 0, 1, 2 and 3;
or B is CONR" wherein R" together with Z$^4$ forms a 5 or 6-membered ring fused to the phenyl;
l is an integer 0, 1, 2, or 3;
t is an integer 0, 1 or 2;
R$^{50}$ is selected from the group consisting of H, alkyl, aryl and aryl optionally substituted with one or more substituent selected from the group consisting of halo, haloalkyl, hydroxy, alkoxy, aryloxy, aryl, nitro and alkyl;
R is X—R$^3$ wherein X is selected from the group consisting of O, S and NR$^4$, wherein R$^3$ and R$^4$ are independently selected from the group consisting of hydrogen; alkyl; alkenyl; alkynyl; haloalkyl; dialkylaminocarbonylalkoxy; aryl; arylalkyl; sugars; steroids and in the case of the free acid, all pharmaceutically acceptable salts thereof;
Y$^3$ and Z$^3$ are independently selected from the group consisting of H, alkyl, aryl, cycloalkyl and aralkyl;
R$^1$ is selected from the group consisting of hydrogen; alkyl; amino,

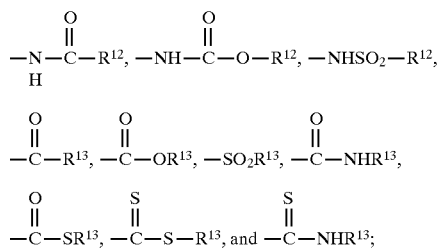

R$^{12}$ is selected from the group consisting of H, alkyl, cycloalkyl, alkylaryl and aryl;

$R^{52}$ is selected from the group consisting of

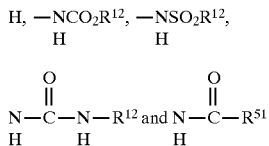

wherein $R^{12}$ is as defined above;

$R^{51}$ is selected from the group consisting of N-substituted pyrrolidinyl, piperidinyl, phenyl and morpholinyl;

$R^{13}$ is selected from the group consisting of hydrogen; alkyl; alkenyl; alkynyl; aryl; carboxyl derivatives; haloalkyl; monocyclic heterocycles; monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido;

alkyl optionally substituted with halo, haloalkyl, hydroxy, alkoxy, aryloxy, thio, alkylthio, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, haloalkyl, cyano, nitro, hydroxy, carboxyl derivatives, alkoxy, aryloxy, amino, alkylamino, dialkylamino, amido, aryl, fused aryl, monocyclic heterocycles; and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl;

aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, carboxyl derivatives, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles; and

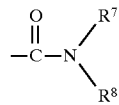

wherein $R^7$ and $R^8$ are as defined above and provided that taken together with the nitrogen, $R^7$ and $R^8$ comprise an amino acid.

2. A compound according to claim 1 wherein 1 is 0.

3. A compound according to claim 2 wherein t is 0.

4. A compound according to claim 3 wherein B is —CONH—.

5. A compound according to claim 4 wherein the compound is selected from the group consisting of ethyl 3-[4-[[[3-[(aminoiminomethyl)amino]phenyl] phenyl]carbonyl]amino]phenyl]-2-propenoate;

3-[4-[[[3-[(aminoiminomethyl)amino]phenyl]-carbonyl] amino]phenyl]-2-propenoic acid;

3-[4-[[[3-[(aminoiminomethyl)amino]phenyl]carbonyl] amino]-3-methylphenyl]propenoic acid;

ethyl 3-[4-[[[3-[(aminoiminomethyl)amino]phenyl] carbonyl]amino]-3-methylphenyl]-2E-propenoate;

3-[4-[[[3-[(aminoiminomethyl)amino]phenyl]carbonyl] amino]-3-ethylphenyl]propenoic acid;

ethyl 3-[4-[[[3-[(aminoiminomethyl)amino]phenyl]-carbonyl]amino]-3-ethylphenyl]propenoate;

3-[4-[[[3-[(aminoiminomethyl)amino]phenyl]carbonyl] amino]-3-chlorophenyl]propenoic acid;

ethyl 3-[4-[[[3-[(aminoiminomethyl)amino]phenyl]-carbonyl]amino]-3-chlorophenyl]-2E-propenoate;

3-[4-[[[3-[(aminoiminomethyl)amino]phenyl]carbonyl] amino]-3-fluorophenyl]-2E-propenoic acid;

3-[4-[[[3-[(aminoiminomethyl)amino]phenyl-carbonyl] amino]-3-(trifluoromethyl)phenyl]-2E-propenoic acid;

3-[4-[[[3-[(aminoiminomethyl)amino]phenyl]carbonyl] amino]-3,5-dimethylphenyl]-2E-propenoic acid;

ethyl 3-[4-[[[3-[(aminoiminomethyl)amino]phenyl]-carbonyl]amino]-3,5-dimethylphenyl]-2E-propenoate;

3-[4-[[[3-[(aminoiminomethyl)amino]phenyl]carbonyl] amino]-3-chloro-5-methylphenyl]-2E-propenoic acid;

3-[4-[[[3-[(aminoiminomethyl)amino]phenyl]carbonyl] amino]naphthalen-1-yl]-2E-propenoic acid;

3-[4-[[[3-[(aminoiminomethyl)amino]phenyl]carbonyl] amino]-3-methoxyphenyl]propenoic acid;

3-[3-methyl-4-[[[3-[(1,4,5,6-tetrahydropyrimidin-2-yl) amino]phenyl]carbonyl]amino]phenyl]propenoic acid;

3-[3-ethyl-4-[[[3-[(1,4,5,6-tetrahydropyrimidin-2-yl) amino]phenyl]carbonyl]amino]phenyl]propenoic acid;

ethyl 3-[3-ethyl-4-[[[3-[(1,4,5,6-tetrahydropyrimidin-2-yl)amino]phenyl]carbonyl]amino]phenyl]propenoate;

3-[4-[[[3-[(4,5-dihydro-1H-imidazol-2-yl)amino]phenyl] carbonyl]amino]-3-ethylphenyl]propenoic acid;

3-[3-chloro-4-[[[3-[(1,4,5,6-tetrahydropyrimidin-2-yl) amino]phenyl]carbonyl]amino]phenyl]propenoic acid;

3-[3-chloro-4-[[[3-[(4,5-dihydro-1H-imidazol-2-yl)-amino]phenyl]carbonyl]amino]phenyl]-2E-propenoic acid;

3-[3,5-dimethyl-4-[[[3-[(1,4,5,6-tetrahydropyrimidin-2-yl)amino)phenyl]carbonyl]amino]phenyl]-2E-propenoic acid;

3-[4-[[[3-[(4,5-dihydroimidazol-2-yl)amino]phenyl] carbonyl]amino]-3,5-dimethylphenyl]-2E-propenoic acid;

ethyl 4-[[[3-[3-[(4,5-dihydroimidazol-2-yl)amino] phenyl]carbonyl]amino]-3,5-dimethylphenyl] propenoate;

3-[4-[[[3-[(aminocarbonyl)amino]phenyl]carbonyl] amino]-3,5-dimethylphenyl]propenoic acid;

3-[4-[[[3-[(aminoiminomethyl)amino]phenyl]carbonyl] amino]-2-chlorophenyl]propenoic acid;

3-[4-[[[3-[(aminoiminomethyl)amino]phenyl]carbonyl] amino]-2,6-dichlorophenyl]propenoic acid;

ethyl 3-[4-[[[3-(aminoiminomethyl)amino]phenyl]-carbonyl]amino]-2-methoxyphenyl]propenoate;

ethyl 3-[4-[[[3-(aminoiminomethyl)amino]phenyl]-carbonyl]amino]-2-methoxyphenyl]propenoic acid;

ethyl 3-[4-[[[3-[(aminoiminomethyl)amino]phenyl]-carbonyl]amino]-2-methylphenyl]propenoate;

3-[4-[[[3-[(aminoiminomethyl)amino]phenyl]-carbonyl] amino]-2-methylphenyl]propenoic acid;

ethyl 3-[4-[[[3-[(aminoiminomethyl)amino]phenyl]-carbonyl]amino]-2-(trifluoromethyl)phenyl] propenoate;

3-[4-[[[3-[(aminoiminomethyl)amino]phenyl]carbonyl]
amino]-2-(trifluoromethyl)phenyl]propenoic acid;

5-[[[3-[(aminoiminomethyl)amino]phenyl]carbonyl]
amino]-2-(2-carboxyethenyl)benzoic acid;

methyl 5-[[[3-[(aminoiminomethyl)amino]phenyl]-
carbonyl]amino]-2-(2-carboxyethenyl)benzoate;

methyl 5-[[[3-[(1,4,5,6-tetrahydropyrimidine-2-yl]amino]
phenyl]carbonyl]amino]-2-(2-carboxyethenyl)
benzoate;

2-(2-carboxyethenyl)-5-[[[3-[(1,4,5,6-
tetrahydropyrimidin-2-yl)amino]phenyl]carbonyl]
amino]benzoic acid;

methyl 2-(2-carboxyethenyl)-5-[[[3-[(1,4,5,6-
tetrahydropyrimidin-2-yl)amino]phenyl]carbonyl]
amino]benzoate;

2-[2-(methoxycarbonyl)ethenyl]-5-[[[3-[(1,4,5,6-
tetrahydropyrimidin-2-yl)amino]phenyl]-carbonyl]
amino]benzoic acid;

methyl 3-[4-[[[3-[(aminoiminomethyl)amino]phenyl]-
carbonyl]amino]-2-(2-methoxycarbonyl-ethenyl)
phenyl]propenoate;

3-[4-[[[3-[(aminoiminomethyl)amino]phenyl]carbonyl]
amino]-2-(2-carboxyethenyl)phenyl]propenoic acid;

ethyl 3-[4-[[[3-[(aminoiminomethyl)amino]phenyl]-
carbonyl]amino]-2-cyanophenyl]propenoate;

3-[4-[[[3-[(aminoiminomethyl)amino]phenyl]carbonyl]
amino]-2-cyanophenyl]propenoic acid;

3-[2-[(methylamino)carbonyl]-4-[[[3-[(1,4,5,6-
tetrahydropyrimidin-2-yl)amino]phenyl]-carbonyl]
amino]phenyl]propenoic acid;

3-[2-[(ethoxycarbonyl)amino]-4-[[[3-[(1,4,5,6-
tetrahydropyrimidin-2-yl)amino]phenyl]-carbonyl]
amino]phenyl]propenoic acid;

2-(dimethylamino)-2-oxoethyl 3-[4-[[[3-[
(aminoiminomethyl)amino]phenyl]carbonyl]amino]
phenyl]propenoate;

2-(dimethylamino)-2-oxoethyl 3-[4-[[[3-[(1,4,5,6-
tetrahydropyrimidin-2-yl)amino]phenyl]-carbonyl]
amino]phenyl]propenoate;

3-[4-[[[3-[(1,4,5,6-tetrahydropyrimidin-2-yl)-amino]
phenyl]carbonyl]amino]phenyl]propenoic acid;

3-[2-methoxy-4-[[[3-[(1,4,5,6-tetrahydropyrimidin-2-yl)
amino]phenyl]carbonyl]amino]phenyl]propenoic acid;

3-[2-chloro-4-[[[3-[(1,4,5,6-tetrahydropyrimidin-2-yl)
amino]phenyl]carbonyl]amino]phenyl]propenoic acid;

3-[4-[[[3-[[amino[(aminocarbonyl)imino)methyl]amino]
phenyl]carbonyl]amino]phenyl]propenoic acid;

3-[4-[[[3-[(aminoiminomethyl)amino]-5-
(trifluoromethyl)-phenyl]carbonyl]amino]phenyl]
propenoic acid;

3-[4-[[[3-[(aminoiminomethyl)amino]-5-
(trifluoromethyl)phenyl]carbonyl]amino]-2-
chlorophenyl]propenoic acid;

3-[4-[[[3-[(aminoiminomethyl)amino]-5-
(trifluoromethyl)phenyl]carbonyl]amino]-2-
methoxyphenyl]propenoic acid;

3-[4-[[[3-[(5,6-dihydro-4H-1,3-thiazin-2-yl)amino]
phenyl]carbonyl]amino]phenyl]propenoic acid;

3-[4-[[[3-[(5,6-dihydro-4H-1,3-thiazin-2-yl)amino]
phenyl]carbonyl]amino]3,5-dimethylphenyl]propenoic
acid;

3-[4-[[[3-[(aminoiminomethyl)amino]phenyl]-carbonyl]
amino]phenyl]-3-phenylpropenoic acid;

3-[4-[[[3-[(aminoiminomethyl)amino]phenyl]-carbonyl]
amino]phenyl]-2-butenoic acid; and 3-[4-[[[3-[(aminoiminomethyl)amino]phenyl]carbonyl]
amino]phenyl]-2-[(phenylcarbonyl)amino]propenoic
acid.

6. A compound according to claim 3 wherein B is
—CONHCH$_2$—.

7. A compound according to claim 6 wherein the compound is selected from the group consisting of methyl 3-[3-[[[[3-[(aminoiminomethyl)amino]phenyl]-
carbonyl]amino]methyl]phenyl]-2-propenoate;

3-[3-[[[[3-[(aminoiminomethyl)amino]phenyl]-carbonyl]
amino]methyl]phenyl]-2-propenoic acid;

ethyl 3-[3-[[[[3-[(1,4,5,6-tetrahydropyrimidin-2-yl)
amino]phenyl]carbonyl]amino]methyl]phenyl]
propenoate;

3-[3-[[[[3-[(1,4,5,6-tetrahydropyrimidin-2-yl)amino]
phenyl]carbonyl]amino]methyl]phenyl]propenoic
acid;

ethyl 3-[3-[[[[3-[[[(phenylmethyl)amino]carbonyl]
amino]phenyl]carbonyl]amino]methyl]phenyl]
propenoate;

3-[3-[[[[3-[[[(phenylmethyl)amino]carbonyl]amino]
phenyl]carbonyl]amino]methyl]phenyl]propenoic
acid;

3-[3-[[[[3-[[4,5-dihydro-1-[(2-methylpropoxy)carbonyl]-
1H-imidazol-2-yl]amino]phenyl]carbonyl]amino]-
methyl]phenyl]propenoic acid;

ethyl 3-[3-[[[[3-[(4,5-dihydro-1H-imidazol-2-yl)amino]
phenyl]carbonyl]amino]methyl]phenyl]propenoate;

3-[3-[[[[3-[(4,5-dihydro-1H-imidazol-2-yl)amino]
phenyl]carbonyl]amino]methyl]phenyl]propenoic
acid;

ethyl 3-[3-[[[[3-[(1,4,5,6-tetrahydropyrimidin-2-yl)-
amino]-5-(trifluoromethyl)phenyl]carbonyl]amino]
methyl]phenyl]propenoate;

3-[3-[[[[3-[(1,4,5,6-tetrahydropyrimidin-2-yl)-amino]-5-
(trifluoromethyl)phenyl]carbonyl]amino]methyl]
phenyl]propenoic acid;

ethyl 3-[3-[[[[3-[(4,5-dihydro-1H-imidazol-2-yl)amino]-
5-(trifluoromethyl)phenyl]carbonyl]amino]-methyl]
phenyl]propenoate;

3-[3-[[[[3-[(4,5-dihydro-1H-imidazol-2-yl)amino]-5-
(trifluoromethyl)phenyl]carbonyl]amino]-methyl]
phenyl]propenoic acid;

ethyl 3-[3-[[[[3-[(2-pyrimidinyl)amino]phenyl]-carbonyl]
amino]methyl]phenyl]propenoate;

3-[3-[[[[3-[(2-pyrimidinyl)amino]phenyl]carbonyl]
amino]methyl]phenyl]propenoic acid;

3-[3-[[[[3-[(aminoiminomethyl)amino]phenyl]carbonyl]
amino]methyl]phenyl]-2E-pentenoic acid; and 3-[3-[[[[3-[(aminoiminomethyl)amino]phenyl]-carbonyl]
amino]methyl]phenyl]-3-(3,5-dichlorophenyl)
propenoic acid.

8. A compound according to claim 3 wherein the compound is selected from the group consisting of 3-[2,3-dihydro-1-[[3-[(1,4,5,6-tetrahydropyrimidin-2-yl)amino]
phenyl]carbonyl]-1H-indol-5-yl]propenoic acid;

3-[1-[[3-[(4,5-dihydro-1H-imidazol-2-yl)amino]phenyl]
carbonyl]2,3-dihydro-1H-indol-5-yl]propenoic acid;

3-[1-[[3-[(1,4,5,6-tetrahydropyrimidin-2-yl)-amino]
phenyl]carbonyl]-1,2,3,4-tetrahydro-quinolin-6-yl]
propenoic acid;

3-[3-[2-[3-[(aminoimino)methyl]amino]phenyl]-2-oxoethoxy]phenyl]propenoic acid;

3-[3-[2-[3-[(4,5-dihydro-1H-imidazol-2-yl)amino]phenoyl]-2-oxoethoxy]phenyl]propenoic acid;

3-[3-[[2-[3-[(aminoiminomethyl)amino]phenyl]-2-hydroxyethyl]amino]phenyl]propenoic acid;

ethyl 3-[3-[2-[3-[(4,5-dihydro-1H-imidazol-2-yl)arnino]-phenoxy]acetyl]phenyl]propenoate;

3-[3-[2-[3-[(4,5-dihydro-1H-imidazol-2-yl)amino]-phenoxy]acetyl]phenyl]propenoic acid;

3-[5-[3-[3-[(aminoiminomethyl)amino]phenyl]-1-oxopropenyl]-2-fluorophenyl]propenoic acid;

3-[5-[3-[3-[(1,4,5,6-tetrahydropyrimidin-2-yl)]phenyl]-1-oxopropenyl]-2-fluorophenyl]propenoic acid;

3-[3-[3-[3-[(aminoiminomethyl)amino]phenyl]-1-oxopropenyl]-4-methoxyphenyl]propenoic acid;

3-[3-[3-[3-[(4,5-dihydro-1H-imidazol-2-yl)amino]phenyl]-1-oxopropenyl]-4-methoxyphenyl]propenoic acid;

3-[3-[3-[3-[(aminoiminomethyl)amino]phenyl]-1-oxopropenyl]phenyl]propenoic acid;

3-[3-[3-[3-[(aminoiminomethyl)amino]phenyl]-3-oxopropenyl]phenyl]propenoic acid;

3-[3-[1-oxo-3-[3-[(1,4,5,6-tetrahydropyrimidin-2-yl)amino]phenyl]-2-propenyl]phenyl]propenoic acid;

3-[3-[3-[3-[(aminoiminomethyl)amino]phenyl]-3-oxopropyl]phenyl]propenoic acid;

3-[3-[3-[3-[(aminoiminomethyl)amino]phenyl]-1-oxopropyl]phenyl]propenoic acid;

3-[3-[1-oxo-3-[3-[(1,4,5,6-tetrahydropyrimidin-2-yl)amino]phenyl]propyl]phenyl]propenoic acid;

3-[3-[3-oxo-3-[3-[(1,4,5,6-tetrahydropyrimidin-2-yl)amino]phenyl]-1-propenyl]phenyl]propenoic acid;

3-[3-[3-oxo-3-[3-[(1,4,5,6-tetrahydropyrimidin-2-yl)amino]phenyl]propyl]phenyl]propenoic acid;

3-[3-[3-[3-[(aminoiminomethyl)amino]phenyl]-3-hydroxypropyl]phenyl]propenoic acid;

3-[4-[2-[3-[(aminoiminomethyl)amino]phenyl]-ethenyl]phenyl]propenoic acid;

3-[4-[2-[3-[(1,4,5,6-tetrahydropyrimidin-2-yl)amino]phenyl]ethenyl]phenyl]propenoic acid;

3-[4-[2-[3-[(4,5-dihydro-1H-imidazol-2-yl)amino]phenyl]ethenyl]phenyl]propenoic acid;

3-[4-[2-[3-[(5,6-dihydro-4H-thiazin-2-yl)amino]phenyl]ethenyl]phenyl]propenoic acid;

3-[4-[[3-[(1,4,5,6-tetrahydropyrimidin-2-yl)amino]phenyl]methoxy]phenyl]propenoic acid;

3-[3-[2-[3-[(aminoiminomethyl)amino]phenyl]-oxazol-4-yl]phenyl]propenoic acid;

3-[4-[2-[3-[(aminoiminomethyl)amino]phenyl]-1H-imidazol-5-yl]phenyl]propenoic acid; and 3-[4-[4-[3-[(aminoiminomethyl)amino]phenyl]-oxazol-2-yl]phenyl]propenoic acid.

9. A pharmaceutical composition comprising a therapeutically effective amount of a compound of the formula

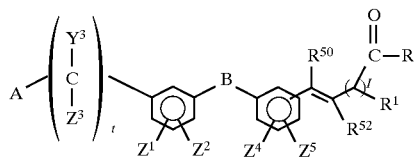

or a pharmaceutically acceptable salt thereof, wherein A is

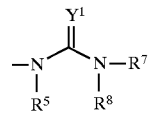

wherein $Y^1$ is selected from the group consisting of N—$R^2$, O, and S;

$R^2$ is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy, carboxyl derivatives and phenyl;

or $R^2$ taken together with $R^7$ forms a 5 membered heteroaromatic ring;

or $R^2$ taken together with $R^7$ forms a 5 membered heteroaromatic ring fused with a phenyl group;

$R^7$ (when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; —SO$_2$R$^{10}$ wherein R$^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

wherein R$^{10}$ is defined above;

or NR$^7$ and R$^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

R$^5$ is selected from the group consisting of H, alkyl, alkenyl, alkynyl, benzyl, and phenethyl; or

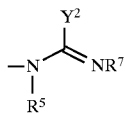

A is wherein y$^2$ is selected from the group consisting of alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; —S—R$^9$ and —O—R$^9$ wherein R$^9$ is selected from the group consisting of H; alkyl; aralkyl; aryl; alkenyl; and alkynyl; or R$^9$ taken together with R$^7$ forms a 4–12 membered mononitrogen containing sulfur or oxygen containing heterocyclic ring; and R$^5$ and R$^7$ are as defined above;

or y$^2$ (when y$^2$ is carbon) taken together with R$^7$ forms a 4–12 membered mononitrogen containing ring optionally substituted with alkyl, aryl or hydroxy;

Z$^1$, Z$^2$, Z$^4$ and Z$^5$ are independently selected from the group consisting of H; alkyl; hydroxy; alkoxy; aryloxy; arylalkoxy; halogen; haloalkyl; haloalkoxy; nitro; amino; aminoalkyl; alkylamino; dialkylamino; cyano; alkylthio; alkylsulfonyl; carboxyl derivatives; carboxylalkenyl; alkoxycarbonylalkenyl; alkoxycarbonylamino; acetamide; aryl; fused aryl; cycloalkyl; thio; monocyclic heterocycles; fused monocyclic heterocycles; and A, wherein A is defined above;

B is selected from the group consisting of

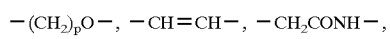

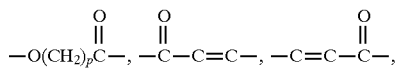

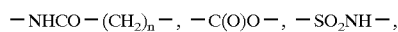

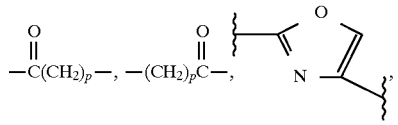

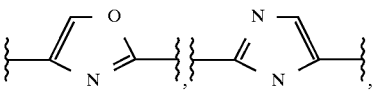

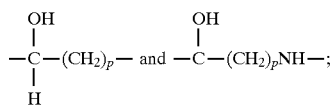

wherein p is an integer selected from the group consisting of 0, 1 and 2; wherein R$^{11}$ is selected from the group consisting of H, alkyl, alkenyl, alkynyl, benzyl and phenethyl; wherein n is an integer selected from the group consisting of 0, 1, 2 and 3;

or B is CONR" wherein R" together with Z$^4$ forms a 5 or 6-membered ring fused to the phenyl;

l is an integer 0, 1, 2, or 3;

t is an integer 0, 1 or 2;

R$^{50}$ is selected from the group consisting of H, alkyl, aryl and aryl optionally substituted with one or more substituent selected from the group consisting of halo, haloalkyl, hydroxy, alkoxy, aryloxy, aryl, nitro and alkyl;

R is X–R$^3$ wherein X is selected from the group consisting of O, S and NR$^4$, wherein R$^3$ and R$^4$ are independently selected from the group consisting of hydrogen; alkyl; alkenyl; alkynyl; haloalkyl; dialkylaminocarbonylalkoxy; aryl; arylalkyl; sugars; steroids and in the case of the free acid, all pharmaceutically acceptable salts thereof;

y$^3$ and Z$^3$ are independently selected from the group consisting of H, alkyl, aryl, cycloalkyl and aralkyl;

R$^1$ is selected from the group consisting of hydrogen; alkyl; amino,

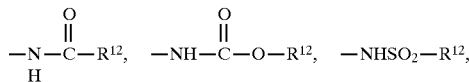

-continued

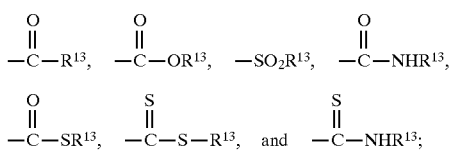

$R^{12}$ is selected from the group consisting of H, alkyl, cycloalkyl, alkylaryl and aryl;
$R^{52}$ is selected from the group consisting of

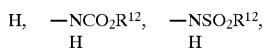

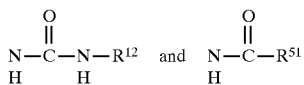

wherein $R^{12}$ is as defined above;
$R^{51}$ is selected from the group consisting of N-substituted pyrrolidinyl, piperidinyl, phenyl and morpholinyl;
$R^{13}$ is selected from the group consisting of hydrogen; alkyl; alkenyl; alkynyl; aryl; carboxyl derivatives; haloalkyl; monocyclic heterocycles; monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido;
alkyl optionally substituted with halo, haloalkyl, hydroxy, alkoxy, aryloxy, thio, alkylthio, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, haloalkyl, cyano, nitro, hydroxy, carboxyl derivatives, alkoxy, aryloxy, amino, alkylamino, dialkylamino, amido, aryl, fused aryl, monocyclic heterocycles; and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl;
aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, carboxyl derivatives, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles; and

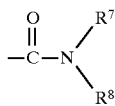

wherein $R^7$ and $R^7$ are as defined above and provided that taken together with the nitrogen, $R^7$ and $R^8$ comprise an amino acid; and a pharmaceutically acceptable carrier.
10. A pharmaceutical composition according to claim 9 wherein 1 is 0.
11. A pharmaceutical composition according to claim 10 wherein t is 0.
12. A pharmaceutical composition according to claim 11 wherein B is —CONH—.
13. A pharmaceutical composition according to claim 12 wherein the compound is selected from the group consisting of
ethyl 3-[4-[[[3-[(aminoiminomethyl)amino]phenyl]phenyl]carbonyl]amino]phenyl]-2-propenoate;
3-[4-[[[3-[(aminoiminomethyl)amino]phenyl]-carbonyl]amino]phenyl]-2-propenoic acid;
3-[4-[[[3-[(aminoiminomethyl)amino]phenyl]carbonyl]amino]-3-methylphenyl]propenoic acid;
ethyl 3-[4-[[[3-[(aminoiminomethyl)amino]phenyl]carbonyl]amino]-3-methylphenyl]-2E-propenoate;
3-[4-[[[3-[(aminoiminomethyl)amino]phenyl]carbonyl]amino]-3-ethylphenyl]propenoic acid;
ethyl 3-[4-[[[3-[(aminoiminomethyl)amino]phenyl]-carbonyl]amino]-3-ethylphenyl]propenoate;
3-[4-[[[3-[(aminoiminomethyl)amino]phenyl]carbonyl]amino]-3-chlorophenyl]propenoic acid;
ethyl 3-[4-[[[3-[(aminoiminomethyl)amino]phenyl]-carbonyl]amino]-3-chlorophenyl]-2E-propenoate;
3-[4-[[[3-[(aminoiminomethyl)amino]phenyl]carbonyl]amino]-3-fluorophenyl]-2E-propenoic acid;
3-[4-[[[3-[(aminoiminomethyl)amino]phenyl]-carbonyl]amino]-3-(trifluoromethyl)phenyl]-2E-propenoic acid;
3-[4-[[[3-[(aminoiminomethyl)amino]phenyl]carbonyl]amino]-3,5-dimethylphenyl]-2E-propenoic acid;
ethyl 3-[4-[[[3-[(aminoiminomethyl)amino]phenyl]-carbonyl]amino]-3,5-dimethylphenyl]-2E-propenoate;
3-[4-[[[3-[(aminoiminomethyl)amino]phenyl]carbonyl]amino]-3-chloro-5-methylphenyl]-2E-propenoic acid;
3-[4-[[[3-[(aminoiminomethyl)amino]phenyl]carbonyl]amino]naphthalen-1-yl]-2E-propenoic acid;
3-[4-[[[3-[(aminoiminomethyl)amino]phenyl]carbonyl]amino]-3-methoxyphenyl]propenoic acid;
3-[3-methyl-4-[[[3-[(1,4,5,6-tetrahydropyrimidin-2-yl)amino]phenyl]carbonyl]amino]phenyl]propenoic acid;
3-[3-ethyl-4-[[[3-[(1,4,5,6-tetrahydropyrimidin-2-yl)amino]phenyl]carbonyl]amino]phenyl]propenoic acid;
ethyl 3-[3-ethyl-4-[[[3-[(1,4,5,6-tetrahydropyrimidin-2-yl)amino]phenyl]carbonyl]amino]phenyl]propenoate;
3-[4-[[[3-[(4,5-dihydro-1H-imidazol-2-yl)amino]phenyl]carbonyl]amino]-3-ethylphenyl]propenoic acid;
3-[3-chloro-4-[[[3-[(1,4,5,6-tetrahydropyrimidin-2-yl)amino]phenyl]carbonyl]amino]phenyl]propenoic acid;
3-[3-chloro-4-[[[3-[(4,5-dihydro-1H-imidazol-2-yl)-amino]phenyl]carbonyl]amino]phenyl]-2E-propenoic acid;
3-[3,5-dimethyl-4-[[[3-[(1,4,5,6-tetrahydropyrimidin-2-yl)amino]phenyl]carbonyl]amino]phenyl]-2E-propenoic acid;
3-[4-[[[3-[(4,5-dihydroimidazol-2-yl)amino]phenyl]carbonyl]amino-3,5-dimethylphenyl]-2E-propenoic acid;
ethyl 4-[[[3-[3-[(4,5-dihydroimidazol-2-yl)amino]phenyl]carbonyl]amino]-3,5-dimethylphenyl]propenoate;
3-[4-[[[3-[(aminocarbonyl)amino]phenyl]carbonyl]amino]-3,5-dimethylphenyl]propenoic acid;

3-[4-[[[3-[(aminoiminomethyl)amino]phenyl]carbonyl]amino]-2-chlorophenyl]propenoic acid;

3-[4-[[[3-[(aminoiminomethyl)amino]phenyl]carbonyl]amino]-2,6-dichlorophenyl]propenoic acid;

ethyl 3-[4-[[[3-[(aminoiminomethyl)amino]phenyl]carbonyl]amino]-2-methoxyphenyl]propenoate;

3-[4-[[[3-(aminoiminomethyl)amino]phenyl-carbonyl]amino]-2-methoxyphenyl]propenoic acid;

ethyl 3-[4-[[[3-[(aminoiminomethyl)amino]phenyl]carbonyl]amino]-2-methylphenyl]propenoate;

3-[4-[[[3-[(aminoiminomethyl)amino]phenyl]carbonyl]amino]-2-methylphenyl]propenoic acid;

ethyl 3-[4-[[[3-[(aminoiminomethyl)amino]phenyl]carbonyl]amino]-2-(trifluoromethyl)phenyl]propenoate;

3-[4-[[[3-[(aminoiminomethyl)amino]phenyl]carbonyl]amino]-2-(trifluoromethyl)phenyl]propenoic acid;

5-[[[3-[(aminoiminomethyl)amino]phenyl]carbonyl]amino]-2-(2-carboxyethenyl)benzoic acid;

methyl 5-[[[3-[(aminoiminomethyl)amino]phenyl]carbonyl]amino]-2-(2-carboxyethenyl)benzoate;

methyl 5-[[[3-[(1,4,5,6-tetrahydropyrimidine-2-yl]amino]phenyl]carbonyl]amino]-2-(2-carboxyethenyl)benzoate;

2-(2-carboxyethenyl)-5-[[[3-[(1,4,5,6-tetrahydropyrimidin-2-yl)amino]phenyl]carbonyl]amino]benzoic acid;

methyl 2-(2-carboxyethenyl)-5-[[[3-[(1,4,5,6-tetrahydropyrimidin-2-yl)amino]phenyl]carbonyl]amino]benzoate;

2-[2-(methoxycarbonyl)ethenyl]-5-[[[3-[(1,4,5,6-tetrahydropyrimidin-2-yl)amino]phenyl]-carbonyl]amino]benzoic acid;

methyl 3-[4-[[[3-[(aminoiminomethyl)amino]phenyl]carbonyl]amino]-2-(2-methoxycarbonyl-ethenyl)phenyl]propenoate;

3-[4-[[[3-[(aminoiminomethyl)amino]phenyl]carbonyl]amino]-2-(2-carboxyethenyl)phenyl]propenoic acid;

ethyl 3-[4-[[[3-[(aminoiminomethyl)amino]phenyl]carbonyl]amino]-2-cyanophenyl]propenoate;

3-[4-[[[3-[(aminoiminomethyl)amino]phenyl]carbonyl]amino]-2-cyanophenyl]propenoic acid;

3-[2-[(methylamino)carbonyl]-4-[[[3-[(1,4,5,6-tetrahydropyrimidin-2-yl)amino]phenyl]-carbonyl]amino]phenyl]propenoic acid;

3-[2-[(ethoxycarbonyl)amino]-4-[[[3-[(1,4,5,6-tetrahydropyrimidin-2-yl)amino]phenyl]-carbonyl]amino]phenyl]propenoic acid;

2-(dimethylamino)-2-oxoethyl 3-[4-[[[3-[(aminoiminomethyl)amino]phenyl]carbonyl]amino]phenyl]propenoate;

2-(dimethylamino)-2-oxoethyl 3-[4-[[[3-[(1,4,5,6-tetrahydropyrimidin-2-yl)amino]phenyl]-carbonyl]amino]phenyl]propenoate;

3-[4-[[[3-[(1,4,5,6-tetrahydropyrimidin-2-yl)-amino]phenyl]carbonyl]amino]phenyl]propenoic acid;

3-[2-methoxy-4-[[[3-[(1,4,5,6-tetrahydropyrimidin-2-yl)amino]phenyl]carbonyl]amino]phenyl]propenoic acid;

3-[2-chloro-4-[[[3-[(1,4,5,6-tetrahydropyrimidin-2-yl)amino]phenyl]carbonyl]amino]phenyl]propenoic acid;

3-[4-[[[3-[[amino[(aminocarbonyl)imino)methyl]amino]phenyl]carbonyl]amino]phenyl]propenoic acid;

3-[4-[[[3-[(aminoiminomethyl)amino]-5-(trifluoromethyl)-phenyl]carbonyl]amino]phenyl]propenoic acid;

3-[4-[[[3-[(aminoiminomethyl)amino]-5-(trifluoromethyl)phenyl]carbonyl]amino]-2-chlorophenyl]propenoic acid;

3-[4-[[[3-[(aminoiminomethyl)amino]-5-(trifluoromethyl)phenyl]carbonyl]amino]-2-methoxyphenyl]propenoic acid;

3-[4-[[[3-[(5,6-dihydro-4H-1,3-thiazin-2-yl)amino]phenyl]carbonyl]amino]phenyl]propenoic acid;

3-[4-[[[3-[(5,6-dihydro-4H-1,3-thiazin-2-yl)amino]phenyl]carbonyl]amino]3,5-dimethylphenyl]propenoic acid;

3-[4-[[[3-[(aminoiminomethyl)amino]phenyl]-carbonyl]amino]phenyl]-3-phenylpropenoic acid;

3-[4-[[[3-[(aminoiminomethyl)amino]phenyl]-carbonyl]amino]phenyl]-2-butenoic acid; and 3-[4-[[[3-[(aminoiminomethyl)amino]phenyl]carbonyl]amino]phenyl]-2-[(phenylcarbonyl)amino]propenoic acid.

14. A pharmaceutical composition according to claim 11 wherein B is —CONHCH$_2$—.

15. A pharmaceutical composition according to claim 14 wherein the compound is selected from the group consisting of methyl 3-[3-[[[[3-[(aminoiminomethyl)amino]phenyl]-carbonyl]amino]methyl]phenyl]-2-propenoate;

3-[3-[[[[3-[(aminoiminomethyl)amino]phenyl]-carbonyl]amino]methyl]phenyl]-2-propenoic acid;

ethyl 3-[3-[[[[3-[(1,4,5,6-tetrahydropyrimidin-2-yl)amino]phenyl]carbonyl]amino]methyl]phenyl]propenoate;

3-[3-[[[[3-[(1,4,5,6-tetrahydropyrimidin-2-yl)amino]phenyl]carbonyl]amino]methyl]phenyl]propenoic acid;

ethyl 3-[3-[[[[3-[[[(phenylmethyl)amino]carbonyl]amino]phenyl]carbonyl]amino]methyl]phenyl]propenoate;

3-[3-[[[[3-[([ (phenylmethyl)amino]carbonyl]amino]phenyl]carbonyl]amino]methyl]phenyl]propenoic acid;

3-[3-[[[[3-[[4,5-dihydro-1-[(2-methylpropoxy)carbonyl]-1H-imidazol-2-yl]amino]phenyl]carbonyl]amino]-methyl]phenyl]propenoic acid;

ethyl 3-[3-[[[[3-[(4,5-dihydro-1H-imidazol-2-yl)amino]phenyl]carbonyl]amino]methyl]phenyl]propenoate;

3-[3-[[[[3-[(4,5-dihydro-1H-imidazol-2-yl)amino]phenyl]carbonyl]amino]methyl]phenyl]propenoic acid;

ethyl 3-[3-[[[[3-[(1,4,5,6-tetrahydropyrimidin-2-yl)-amino]-5-(trifluoromethyl)phenyl]carbonyl]amino]methyl]phenyl]propenoate;

3-[3-[[[[3-[(1,4,5,6-tetrahydropyrimidin-2-yl)-amino]-5-(trifluoromethyl)phenyl]carbonyl]amino]methyl]phenyl]propenoic acid;

ethyl 3-[3-[[[[3-[(4,5-dihydro-1H-imidazol-2-yl)amino]-5-(trifluoromethyl)phenyl]carbonyl]amino]-methyl]phenyl]propenoate;

3-[3-[[[[3-[(4,5-dihydro-1H-imidazol-2-yl)amino]-5-(trifluoromethyl)phenyl]carbonyl]amino]-methyl]phenyl]propenoic acid;

ethyl 3-[3-[[[[3-[(2-pyrimidinyl)amino]phenyl]-carbonyl]amino]methyl]phenyl]propenoate;

3-[3-[[[[3-[(2-pyrimidinyl)amino]phenyl]carbonyl]
   amino]methyl]phenyl]propenoic acid;
3-[3-[[[[3-[(aminoiminomethyl)amino]phenyl]carbonyl]
   amino]methyl]phenyl]-2E-pentenoic acid; and
3-[3-[[[[3-[(aminoiminomethyl)amino]phenyl]-carbonyl]
   amino]methyl]phenyl]-3-(3,5-dichlorophenyl)
   propenoic acid.

16. A pharmaceutical composition according to claim 9 wherein the compound is selected from the group consisting of 3-[2,3-dihydro-1-[[3-[(1,4,5,6-tetrahydropyrimidin-2-yl)
   amino]phenyl]carbonyl]-1H-indol-5-yl]propenoic
   acid;
3-[1-[[3-[(4,5-dihydro-1H-imidazol-2-yl)amino]phenyl]
   carbonyl]2,3-dihydro-1H-indol-5-yl]propenoic acid;
3-[1-[[3-[(1,4,5,6-tetrahydropyrimidin-2-yl)-amino]
   phenyl]carbonyl]-1,2,3,4-tetrahydro-quinolin-6-yl]
   propenoic acid;
3-[3-[2-[3-[(aminoimino)methyl]amino]phenyl]-2-
   oxoethoxy]phenyl]propenoic acid;
3-[3-[2-[3-[(4,5-dihydro-1H-imidazol-2-yl)amino]
   phenoyl]-2-oxoethoxy]phenyl]propenoic acid;
3-[3-[[2-[3-[(aminoiminomethyl)amino]phenyl]-2-
   hydroxyethyl]amino]phenyl]propenoic acid;
ethyl 3-[3-[2-[3-[(4,5-dihydro-1H-imidazol-2-yl)amino]-
   phenoxy]acetyl]phenyl]propenoate;
3-[3-[2-[3-[(4,5-dihydro-1H-imidazol-2-yl)amino]-
   phenoxy]acetyl]phenyl]propenoic acid;
3-[5-[3-[3-[(aminoiminomethyl)amino]phenyl]-1-
   oxopropenyl]-2-fluorophenyl]propenoic acid;
3-[5-[3-[3-[(1,4,5,6-tetrahydropyrimidin-2-yl)]phenyl]-1-
   oxopropenyl]-2-fluorophenyl]propenoic acid;
3-[3-[3-[3-[(aminoiminomethyl)amino]phenyl]-1-
   oxopropenyl]-4-methoxyphenyl]propenoic acid;
3-[3-[3-[3-[(4,5-dihydro-1H-imidazol-2-yl)amino]
   phenyl]-1-oxopropenyl]-4-methoxyphenyl]propenoic
   acid;
3-[3-[3-[3-[(aminoiminomethyl)amino]phenyl]-1-
   oxopropenyl]phenyl]propenoic acid;
3-[3-[3-[3-[(aminoiminomethyl)amino]phenyl]-3-
   oxopropenyl]phenyl]propenoic acid;
3-[3-[1-oxo-3-[3-[(1,4,5,6-tetrahydropyrimidin-2-yl)
   amino]phenyl]-2-propenyl]phenyl]propenoic acid;
3-[3-[3-[3-[(aminoiminomethyl)amino]phenyl]-3-
   oxopropyl]phenyl]propenoic acid;
3-[3-[3-[3-[(aminoiminomethyl)amino]phenyl]-1-
   oxopropyl]phenyl]propenoic acid;
3-[3-[1-oxo-3-[3-[(1,4,5,6-tetrahydropyrimidin-2-yl)
   amino]phenyl]propyl]phenyl]propenoic acid;
3-[3-[3-oxo-3-[3-[(1,4,5,6-tetrahydropyrimidin-2-yl)
   amino]phenyl]-1-propenyl]phenyl]propenoic acid;
3-[3-[3-oxo-3-[3-[(1,4,5,6-tetrahydropyrimidin-2-yl)
   amino]phenyl]propyl]phenyl]propenoic acid;
3-[3-[3-[3-[(aminoiminomethyl)amino]phenyl]-3-
   hydroxypropyl]phenyl propenoic acid;
3-[4-[2-[3-[(aminoiminomethyl)amino]phenyl]-ethenyl]
   phenyl]propenoic acid;
3-[4-[2-[3-[(1,4,5,6-tetrahydropyrimidin-2-yl)amino]
   phenyl]ethenyl]phenyl]propenoic acid;
3-[4-[2-[3-[(4,5-dihydro-1H-imidazol-2-yl)amino]
   phenyl]ethenyl]phenyl]propenoic acid;
3-[4-[2-[3-[(5,6-dihydro-4H-thiazin-2-yl)amino]phenyl]
   ethenyl]phenyl]propenoic acid;
3-[4-[[3-[(1,4,5,6-tetrahydropyrimidin-2-yl)amino]
   phenyl]methoxy]phenyl]propenoic acid;
3-[3-(2-[3-[(aminoiminomethyl)amino]phenyl]-oxazol-4-
   yl]phenyl]propenoic acid;
3-[4-[2-[3-[(aminoiminomethyl)amino]phenyl]-1H-
   imidazol-5-yl]phenyl]propenoic acid; and
3-[4-[4-[3-[(aminoiminomethyl)amino]phenyl]-oxazol-2-
   yl]phenyl]propenoic acid.

17. A method for treating conditions mediated by the $\alpha_v\beta_3$ integrin in a mammal in need of such treatment comprising administering a therapeutically effective $\alpha_v\beta_3$ inhibiting amount of a compound of the formula

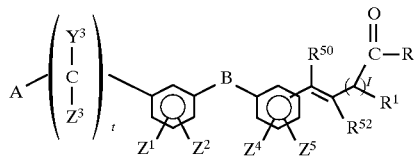

or a pharmaceutically acceptable salt thereof, wherein
A is

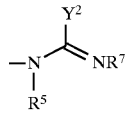

wherein $Y^1$ is selected from the group consisting of N—$R^2$, O, and S;

$R^2$ is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy, carboxyl derivatives and phenyl;

or $R^2$ taken together with $R^7$ forms a 5 membered heteroaromatic ring;

or $R^2$ taken together with $R^7$ forms a 5 membered heteroaromatic ring fused with a phenyl group;

$R^7$ (when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; $-SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and $$-\overset{O}{\underset{\|}{C}}-R^{10}$$

wherein $R^{10}$ is defined above;
or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;
$R^5$ is selected from the group consisting of H, alkyl, alkenyl, alkynyl, benzyl, and phenethyl; or

A is
wherein $y^2$ is selected from the group consisting of alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; $-S-R^9$ and $-O-R^9$ wherein $R^9$ is selected from the group consisting of H; alkyl; aralkyl; aryl; alkenyl; and alkynyl; or $R^9$ taken together with $R^7$ forms a 4–12 membered mononitrogen containing sulfur or oxygen containing heterocyclic ring; and
$R^5$ and $R^7$ are as defined above;
or $y^2$ (when $y^2$ is carbon) taken together with $R^7$ forms a 4–12 membered mononitrogen containing ring optionally substituted with alkyl, aryl or hydroxy;

$Z^1$, $Z^2$, $Z^4$ and Z5 are independently selected from the group consisting of H; alkyl; hydroxy; alkoxy; aryloxy; arylalkoxy; halogen; haloalkyl; haloalkoxy; nitro; amino; aminoalkyl; alkylamino; dialkylamino; cyano; alkylthio; alkylsulfonyl; carboxyl derivatives; carboxylalkenyl; alkoxycarbonylalkenyl; alkoxycarbonylamino; acetamide; aryl; fused aryl; cycloalkyl; thio; monocyclic heterocycles; fused monocyclic heterocycles; and A, wherein A is defined above;

B is selected from the group consisting of $-(CH_2)_pO-$, $-CH=CH-$, $-CH_2CONH-$, $-CONH-(CH_2)_p-$, $-CONR^{11}-$, $-\overset{O}{\underset{\|}{C}}(CH_2)_pO-$, $-O(CH_2)_pC-$, $-\overset{O}{\underset{\|}{C}}-C\equiv C-$, $-C\equiv C-\overset{O}{\underset{\|}{C}}-$, $-NHCO-(CH_2)_n-$, $-C(O)O-$, $-SO_2NH-$, $-\overset{O}{\underset{\|}{C}}(CH_2)_p-$, $-(CH_2)_p\overset{O}{\underset{\|}{C}}-$,

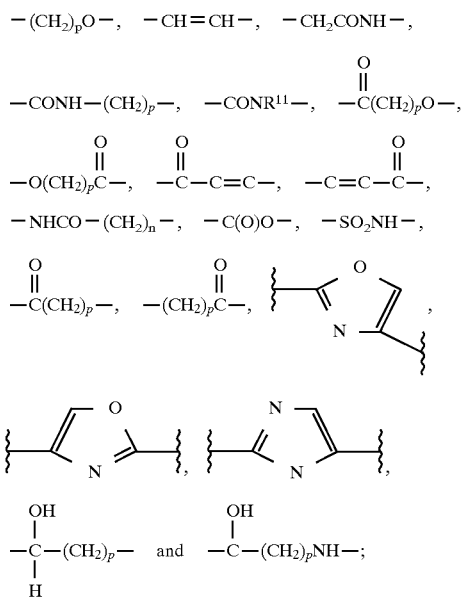

$-\overset{OH}{\underset{H}{\underset{|}{C}}}-(CH_2)_p-$ and $-\overset{OH}{\underset{|}{C}}-(CH_2)_pNH-$;

wherein p is an integer selected from the group consisting of 0, 1 and 2; wherein $R^{11}$ is selected from the group consisting of H, alkyl, alkenyl, alkynyl, benzyl and phenethyl; wherein n is an integer selected from the group consisting of 0, 1, 2 and 3;
or B is CONR" wherein R" together with $Z^4$ forms a 5 or 6-membered ring fused to the phenyl;
l is an integer 0, 1, 2, or 3;
t is an integer 0, 1 or 2;
$R^{50}$ is selected from the group consisting of H, alkyl, aryl and aryl optionally substituted with one or more substituent selected from the group consisting of halo, haloalkyl, hydroxy, alkoxy, aryloxy, aryl, nitro and alkyl;
R is $X-R^3$ wherein X is selected from the group consisting of O, S and $NR^4$, wherein $R^3$ and $R^4$ are independently selected from the group consisting of hydrogen; alkyl; alkenyl; alkynyl; haloalkyl; dialkylaminocarbonylalkoxy; aryl; arylalkyl; sugars; steroids and in the case of the free acid, all pharmaceutically acceptable salts thereof;

$Y^3$ and $Z^3$ are independently selected from the group consisting of H, alkyl, aryl, cycloalkyl and aralkyl;

$R^1$ is selected from the group consisting of hydrogen; alkyl; amino,

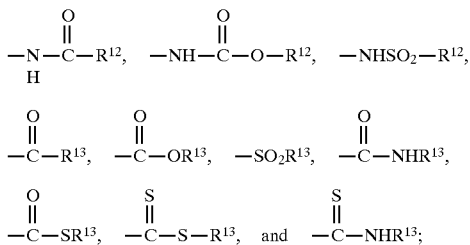

$R^{12}$ is selected from the group consisting of H, alkyl, cycloalkyl, alkylaryl and aryl;

$R^{52}$ is selected from the group consisting of

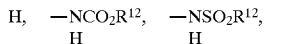

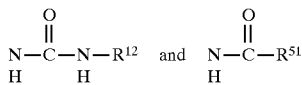

wherein $R^{12}$ is as defined above;

$R^{51}$ is selected from the group consisting of N-substituted pyrrolidinyl, piperidinyl, phenyl and morpholinyl;

$R^{13}$ is selected from the group consisting of hydrogen; alkyl; alkenyl; alkynyl; aryl; carboxyl derivatives; haloalkyl; monocyclic heterocycles; monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido;

alkyl optionally substituted with halo, haloalkyl, hydroxy, alkoxy, aryloxy, thio, alkylthio, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, haloalkyl, cyano, nitro, hydroxy, carboxyl derivatives, alkoxy, aryloxy, amino, alkylamino, dialkylamino, amido, aryl, fused aryl, monocyclic heterocycles; and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl;

aryl optionally substituted in one or more positions with halo, haloalkyl, alkyl, alkoxy, aryloxy, methylenedioxy, ethylenedioxy, alkylthio, aloalkylthio, thio, hydroxy, cyano, nitro, carboxyl derivatives, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles; and

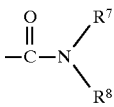

wherein $R^7$ and $R^8$ are as defined above and provided that taken together with the nitrogen, $R^7$ and $R^8$ comprise an amino acid.

18. A method according to claim 17 wherein the compound is selected from the group consisting of ethyl 3-[4-[[[3-[(aminoiminomethyl)amino]phenyl]phenyl]carbonyl]amino]phenyl]-2-propenoate;

3-[4-[[[3-[(aminoiminomethyl)amino]phenyl]-carbonyl]amino]phenyl]-2-propenoic acid;

methyl 3-[3-[[[[3-[(aminoiminomethyl)amino]phenyl]-carbonyl]amino]methyl]phenyl]-2-propenoate;

3-[3-[[[[3-[(aminoiminomethyl)amino]phenyl]-carbonyl]amino]methyl]phenyl]-2-propenoic acid;

ethyl 3-[4-[[[3-[(aminoiminomethyl)amino]phenyl]phenyl]carbonyl]amino]phenyl]-2-propenoate;

3-[4-[[[3-[(aminoiminomethyl)amino]phenyl]-carbonyl]amino]phenyl]-2-propenoic acid;

3-[4-[[[3-[(aminoiminomethyl)amino]phenyl]carbonyl]amino]-3-methylphenyl]propenoic acid;

ethyl 3-[4-[[[3-[(aminoiminomethyl)amino]phenyl]carbonyl]amino]-3-methylphenyl]-2E-propenoate;

3-[4-[[[3-[(aminoiminomethyl)amino]phenyl]carbonyl]amino]-3-ethylphenyl]propenoic acid;

ethyl 3-[4-[[[3-[(aminoiminomethyl)amino]phenyl]-carbonyl]amino]-3-ethylphenyl]propenoate;

3-[4-[[[3-[(aminoiminomethyl)amino]phenyl]carbonyl]amino]-3-chlorophenyl]propenoic acid;

ethyl 3-[4-[[[3-[(aminoiminomethyl)amino]phenyl]-carbonyl]amino]-3-chlorophenyl]-2E-propenoate;

3-[4-[[[3-[(aminoiminomethyl)amino]phenyl]carbonyl]amino]-3-fluorophenyl]-2E-propenoic acid;

3-[4-[[[3-[(aminoiminomethyl)amino]phenyl]carbonyl]amino]-3-(trifluoromethyl)phenyl]-2E-propenoic acid;

3-[4-[[[3-[(aminoiminomethyl)amino]phenyl]carbonyl]amino]-3,5-dimethylphenyl]-2E-propenoic acid;

ethyl 3-[4-[[[3-[(aminoiminomethyl)amino]phenyl]-carbonyl]amino]-3,5-dimethylphenyl]-2E-propenoate;

3-[4-[[[3-[(aminoiminomethyl)amino]phenyl]carbonyl]amino]-3-chloro-5-methylphenyl]-2E-propenoic acid;

3-[4-[[[3-[(aminoiminomethyl)amino]phenyl]carbonyl]amino]naphthalen-1-yl]-2E-propenoic acid;

3-[4-[[[3-[(aminoiminomethyl)amino]phenyl]carbonyl]amino]-3-methoxyphenyl]propenoic acid;

3-[3-methyl-4-[[[3-[(1,4,5,6-tetrahydropyrimidin-2-yl)amino]phenyl]carbonyl]amino]phenyl]propenoic acid;

3-[3-ethyl-4-[[[3-[(1,4,5,6-tetrahydropyrimidin-2-yl)amino]phenyl]carbonyl]amino]phenyl]propenoic acid;

ethyl 3-[3-ethyl-4-[[[3-[(1,4,5,6-tetrahydropyrimidin-2-yl)amino]phenyl]carbonyl]amino]phenyl]propenoate;

3-[4-[[[3-[(4,5-dihydro-1H-imidazol-2-yl)amino]phenyl]carbonyl]amino]-3-ethylphenyl]propenoic acid;

3-[3-chloro-4-[[[3-[(1,4,5,6-tetrahydropyrimidin-2-yl)amino]phenyl]carbonyl]amino]phenyl]propenoic acid;

3-[3-chloro-4-[[[3-[(4,5-dihydro-1H-imidazol-2-yl)-amino]phenyl]carbonyl]amino]phenyl]-2E-propenoic acid;

3-[3,5-dimethyl-4-[[[3-[(1,4,5,6-tetrahydropyrimidin-2-yl)amino]phenyl]carbonyl]amino]phenyl]-2E-propenoic acid;

3-[4-[[[3-[(4,5-dihydroimidazol-2-yl)amino]phenyl]carbonyl]amino]-3,5-dimethylphenyl]-2E-propenoic acid;

ethyl 4-[[[3-[3-[(4,5-dihydroimidazol-2-yl)amino]phenyl]carbonyl]amino]-3,5-dimethylphenyl]propenoate;

3-[4-[[[3-[(aminocarbonyl)amino]phenyl]carbonyl]amino]-3,5-dimethylphenyl]propenoic acid;

3-[4-[[[3-[(aminoiminomethyl)amino]phenyl]carbonyl]amino]-2-chlorophenyl]propenoic acid;

3-[4-[[[3-[(aminoiminomethyl)amino]phenyl]carbonyl]amino]-2,6-dichlorophenyl]propenoic acid;

ethyl 3-[4-[[[3-(aminoiminomethyl)amino]phenyl]-carbonyl]amino]-2-methoxyphenyl]propenoate;

ethyl 3-[4-[[[3-(aminoiminomethyl)amino]phenyl]-carbonyl]amino]-2-methoxyphenyl]propenoic acid;

ethyl 3-[4-[[[3-[(aminoiminomethyl)amino]phenyl]carbonyl]amino]-2-methylphenyl]propenoate;

3-[4-[[[3-[(aminoiminomethyl)amino]phenyl]carbonyl]amino]-2-methylphenyl]propenoic acid;

ethyl 3-[4-[[[3-[(aminoiminomethyl)amino]phenyl]-carbonyl]amino]-2-(trifluoromethyl)phenyl]propenoate;

3-[4-[[[3-[(aminoiminomethyl)amino]phenyl]carbonyl]amino]-2-(trifluoromethyl)phenyl]propenoic acid;

5-[[[3-[(aminoiminomethyl)amino]phenyl]carbonyl]amino]-2-(2-carboxyethenyl)benzoic acid;

methyl 5-[[[3-[(aminoiminomethyl)amino]phenyl]-carbonyl]amino]-2-(2-carboxyethenyl)benzoate;

methyl 5-[[[3-[(1,4,5,6-tetrahydropyrimidine-2-yl]amino]phenyl]carbonyl]amino]-2-(2-carboxyethenyl)benzoate;

2-(2-carboxyethenyl)-5-[[[3-[(1,4,5,6-tetrahydropyrimidin-2-yl)amino]phenyl]carbonyl]amino]benzoic acid;

methyl 2-(2-carboxyethenyl)-5-[[[3-[(1,4,5,6-tetrahydropyrimidin-2-yl)amino]phenyl]carbonyl]amino]benzoate;

2-[2-(methoxycarbonyl)ethenyl]-5-[[[3-[(1,4,5,6-tetrahydropyrimidin-2-yl)amino]phenyl]-carbonyl]amino]benzoic acid;

methyl 3-[4-[[[3-[(aminoiminomethyl)amino]phenyl]-carbonyl]amino]-2-(2-methoxycarbonyl-ethenyl)phenyl]propenoate;

3-[4-[[[3-[(aminoiminomethyl)amino]phenyl]carbonyl]amino]-2-(2-carboxyethenyl)phenyl]propenoic acid;

ethyl 3-[4-[[[3-[(aminoiminomethyl)amino]phenyl]carbonyl]amino]-2-cyanophenyl]propenoate;

3-[4-[[[3-[(aminoiminomethyl)amino]phenyl]carbonyl]amino]-2-cyanophenyl]propenoic acid;

3-[2-[(methylamino)carbonyl]-4-[[[3-[(1,4,5,6-tetrahydropyrimidin-2-yl)amino]phenyl]-carbonyl]amino]phenyl]propenoic acid;

3-[2-[(ethoxycarbonyl)amino]-4-[[[3-[(1,4,5,6-tetrahydropyrimidin-2-yl)amino]phenyl]-carbonyl]amino]phenyl]propenoic acid;

2-(dimethylamino)-2-oxoethyl 3-[4-[[[3-[(aminoiminomethyl)amino]phenyl]carbonyl]amino]phenyl]propenoate;

2-(dimethylamino)-2-oxoethyl 3-[4-[[[3-[(1,4,5,6-tetrahydropyrimidin-2-yl)amino]phenyl]-carbonyl]amino]phenyl]propenoate;

3-[4-[[[3-[(1,4,5,6-tetrahydropyrimidin-2-yl)-amino]phenyl]carbonyl]amino]phenyl]propenoic acid;

3-[2-methoxy-4-[[[3-[(1,4,5,6-tetrahydropyrimidin-2-yl)amino]phenyl]carbonyl]amino]phenyl]propenoic acid;

3-[2-chloro-4-[[[3-[(1,4,5,6-tetrahydropyrimidin-2-yl)amino]phenyl]carbonyl]amino]phenyl]propenoic acid;

3-[4-[[[3-[[amino[(aminocarbonyl)imino)methyl]amino]phenyl]carbonyl]amino]phenyl]propenoic acid;

3-[4-[[[3-[(aminoiminomethyl)amino]-5-(trifluoromethyl)-phenyl]carbonyl]amino]phenyl]propenoic acid;

3-[4-[[[3-[(aminoiminomethyl)amino]-5-(trifluoromethyl)phenyl]carbonyl]amino]-2-chlorophenyl]propenoic acid;

3-[4-[[[3-[(aminoiminomethyl)amino]-5-(trifluoromethyl)phenyl]carbonyl]amino]-2-methoxyphenyl]propenoic acid;

3-[4-[[[3-[(5,6-dihydro-4H-1,3-thiazin-2-yl)amino]phenyl]carbonyl]amino]phenyl]propenoic acid;

3-[4-[[[3-[(5,6-dihydro-4H-1,3-thiazin-2-yl)amino]phenyl]carbonyl]amino]3,5-dimethylphenyl]propenoic acid;

3-[4-[[[3-[(aminoiminomethyl)amino]phenyl]-carbonyl]amino]phenyl]-3-phenylpropenoic acid;

3-[4-[[[3-[(aminoiminomethyl)amino]phenyl]-carbonyl]amino]phenyl]-2-butenoic acid;

3-[4-[[[3-[(aminoiminomethyl)amino]phenyl]carbonyl]amino]phenyl]-2-[(phenylcarbonyl)amino]propenoic acid ethyl 3-[3-[[[[3-[(1,4,5,6-tetrahydropyrimidin-2-yl)amino]phenyl]carbonyl]amino]methyl]phenyl]propenoate;

3-[3-[[[[3-[(1,4,5,6-tetrahydropyrimidin-2-yl)amino]phenyl]carbonyl]amino]methyl]phenyl]propenoic acid;

ethyl 3-[3-[[[[3-[[[(phenylmethyl)amino]carbonyl]amino]phenyl]carbonyl]amino]methyl]phenyl]propenoate;

3-[3-[[[[3-[[[(phenylmethyl)amino]carbonyl]amino]phenyl]carbonyl]amino]methyl]phenyl]propenoic acid;

3-[3-[[[[3-[[4,5-dihydro-1-[(2-methylpropoxy)carbonyl]-1H-imidazol-2-yl]amino]phenyl]carbonyl]amino]-methyl]phenyl]propenoic acid;

ethyl 3-[3-[[[[3-[(4,5-dihydro-1H-imidazol-2-yl)amino]phenyl]carbonyl]amino]methyl]phenyl]propenoate;

3-[3-[[[[3-[(4,5-dihydro-1H-imidazol-2-yl)amino]phenyl]carbonyl]amino]methyl]phenyl]propenoic acid;

ethyl 3-[3-[[[[3-[(1,4,5,6-tetrahydropyrimidin-2-yl)-amino]-5-(trifluoromethyl)phenyl]carbonyl]amino]methyl]phenyl]propenoate;

3-[3-[[[[3-[(1,4,5,6-tetrahydropyrimidin-2-yl)-amino]-5-(trifluoromethyl)phenyl]carbonyl]amino]methyl]phenyl]propenoic acid;

ethyl 3-[3-[[[[3-[(4,5-dihydro-1H-imidazol-2-yl)amino]-5-(trifluoromethyl)phenyl]carbonyl]amino]-methyl]phenyl]propenoate;

3-[3-[[[[(3-[(4,5-dihydro-1H-imidazol-2-yl)amino]-5-(trifluoromethyl)phenyl]carbonyl]amino]-methyl]phenyl]propenoic acid;

ethyl 3-[3-[[[[3-[(2-pyrimidinyl)amino]phenyl]-carbonyl]amino]methyl]phenyl]propenoate;

3-[3-[[[[3-[(2-pyrimidinyl)amino]phenyl]carbonyl]
amino]methyl]phenyl]propenoic acid;

3-[3-[[[[3-[(aminoiminomethyl)amino]phenyl]carbonyl]
amino]methyl]phenyl]-2E-pentenoic acid;

3-[3-[[[[3-[(aminoiminomethyl)amino]phenyl]-carbonyl]
amino]methyl]phenyl]-3-(3,5-dichlorophenyl)
propenoic acid;

3-[2,3-dihydro-1-[[3-[(1,4,5,6-tetrahydropyrimidin-2-yl)
amino]phenyl]carbonyl]-1H-indol-5-yl]propenoic
acid;

3-[1-[[3-[(4,5-dihydro-1H-imidazol-2-yl)amino]phenyl]
carbonyl]2,3-dihydro-1H-indol-5-yl]propenoic acid;

3-[1-[[3-[(1,4,5,6-tetrahydropyrimidin-2-yl)-amino]
phenyl]carbonyl]-1,2,3,4-tetrahydro-quinolin-6-yl]
propenoic acid;

3-[3-[2-[3-[(aminoimino)methyl]amino]phenyl]-2-
oxoethoxy]phenyl]propenoic acid;

3-[3-[2-[3-[(4,5-dihydro-1H-imidazol-2-yl)amino]
phenoyl]-2-oxoethoxy]phenyl]propenoic acid;

3-[3-[[2-[3-[(aminoiminomethyl)amino]phenyl]-2-
hydroxyethyl]amino]phenyl]propenoic acid;

ethyl 3-[3-[2-[3-[(4,5-dihydro-1H-imidazol-2-yl)amino]-
phenoxy]acetyl]phenyl]propenoate;

3-[3-[2-[3-[(4,5-dihydro-1H-imidazol-2-yl)amino]-
phenoxy]acetyl]phenyl]propenoic acid;

3-[5-[3-[3-[(aminoiminomethyl)amino]phenyl]-1-
oxopropenyl]-2-fluorophenyl]propenoic acid;

3-[5-[3-[3-[(1,4,5,6-tetrahydropyrimidin-2-yl)]phenyl]-1-
oxopropenyl]-2-fluorophenyl]propenoic acid;

3-[3-[3-[3-[(aminoiminomethyl)amino]phenyl]-1-
oxopropenyl]-4-methoxyphenyl]propenoic acid;

3-[3-[3-[3-[(4,5-dihydro-1H-imidazol-2-yl)amino]
phenyl]-1-oxopropenyl]-4-methoxyphenyl]propenoic
acid;

3-[3-[3-[3-[(aminoiminomethyl)amino]phenyl]-1-
oxopropenyl]phenyl]propenoic acid;

3-[3-[3-[3-[(aminoiminomethyl)amino]phenyl]-3-
oxopropenyl]phenyl]propenoic acid;

3-[3-[1-oxo-3-[3-[(1,4,5,6-tetrahydropyrimidin-2-yl)
amino]phenyl]-2-propenyl]phenyl]propenoic acid;

3-[3-[3-[3-[(aminoiminomethyl)amino]phenyl]-3-
oxopropyl]phenyl]propenoic acid;

3-[3-[3-[3-[(aminoiminomethyl)amino]phenyl]-1-
oxopropyl]phenyl]propenoic acid;

3-[3-[1-oxo-3-[3-[(1,4,5,6-tetrahydropyrimidin-2-yl)
amino]phenyl]propyl]phenyl]propenoic acid;

3-[3-[3-oxo-3-[3-[(1,4,5,6-tetrahydropyrimidin-2-yl)
amino]phenyl]-1-propenyl]phenyl]propenoic acid;

3-[3-[3-oxo-3-[3-[(1,4,5,6-tetrahydropyrimidin-2-yl)
amino]phenyl]propyl]phenyl]propenoic acid;

3-[3-[3-[3-[(aminoiminomethyl)amino]phenyl]-3-
hydroxypropyl]phenyl]propenoic acid;

3-[4-[2-[3-[(aminoiminomethyl)amino]phenyl]-ethenyl]
phenyl]propenoic acid;

3-[4-[2-[3-[(1,4,5,6-tetrahydropyrimidin-2-yl)amino]
phenyl]ethenyl]phenyl]propenoic acid;

3-[4-[2-[3-[(4,5-dihydro-1H-imidazol-2-yl)amino]
phenyl]ethenyl]phenyl]propenoic acid;

3-[4-[2-[3-[(5,6-dihydro-4H-thiazin-2-yl)amino]phenyl]
ethenyl]phenyl]propenoic acid;

3-[4-[[3-[(1,4,5,6-tetrahydropyrimidin-2-yl)amino]
phenyl]methoxy]phenyl]propenoic acid;

3-[3-[2-[3-[(aminoiminomethyl)amino]phenyl]-oxazol-4-
yl]phenyl]propenoic acid;

3-[4-[2-[3-[(aminoiminomethyl)amino]phenyl]-1H-
imidazol-5-yl]phenyl]propenoic acid; and 3-[4-[4-[3-[(aminoiminomethyl)amino]phenyl]-oxazol-2-
yl]phenyl]propenoic acid.

19. A method according to claim 17 wherein the condition treated is tumor metastasis.

20. A method according to claim 18 wherein the condition treated is tumor metastasis.

21. A method according to claim 17 wherein the condition treated is solid tumor growth.

22. A method according to claim 18 wherein the condition treated is solid tumor growth.

23. A method according to claim 17 wherein the condition treated is angiogenesis.

24. A method according to claim 18 wherein the condition treated is angiogenesis.

25. A method according to claim 17 wherein the condition treated is osteoporosis.

26. A method according to claim 18 wherein the condition treated is osteoporosis.

27. A method according to claim 17 wherein the condition treated is humoral hypercalcemia of malignancy.

28. A method according to claim 18 wherein the condition treated is humoral hypercalcemia of malignancy.

29. A method according to claim 17 wherein the condition treated is smooth muscle cell migration.

30. A method according to claim 18 wherein the condition treated is smooth muscle cell migration.

31. A method according to claim 17 wherein restenosis is inhibited.

32. A method according to claim 18 wherein restenosis is inhibited.

* * * * *